(12) United States Patent
Johnson et al.

(10) Patent No.: US 12,195,880 B2
(45) Date of Patent: *Jan. 14, 2025

(54) SYSTEMS AND METHODS FOR MASSIVELY PARALLEL COMBINATORIAL ANALYSIS OF SINGLE CELLS

(71) Applicant: GigaGen, Inc., South San Francisco, CA (US)

(72) Inventors: David Scott Johnson, South San Francisco, CA (US); Adam Shultz Adler, Belmont, CA (US); Matthew James Spindler, San Francisco, CA (US); Rena Aviva Mizrahi, Pacifica, CA (US)

(73) Assignee: GigaGen, Inc., San Carlos, CA (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/872,042

(22) Filed: Jul. 25, 2022

(65) Prior Publication Data

US 2023/0124998 A1   Apr. 20, 2023

Related U.S. Application Data

(60) Continuation of application No. 17/392,892, filed on Aug. 3, 2021, now Pat. No. 11,427,933, which is a
(Continued)

(51) Int. Cl.
*C40B 50/06* (2006.01)
*C07K 14/725* (2006.01)
(Continued)

(52) U.S. Cl.
CPC .......... *C40B 40/08* (2013.01); *C07K 14/7051* (2013.01); *C07K 14/70539* (2013.01);
(Continued)

(58) Field of Classification Search
None
See application file for complete search history.

(56) References Cited

U.S. PATENT DOCUMENTS

| 2015/0141261 A1 | 5/2015 | Hunicke-Smith et al. |
| 2015/0298091 A1 | 10/2015 | Weitz et al. |
| 2016/0201129 A1 | 7/2016 | Weitz et al. |

FOREIGN PATENT DOCUMENTS

| CA | 3026773 | 1/2018 |
| EP | 2186827 A1 | 5/2010 |

(Continued)

OTHER PUBLICATIONS

Extended European Search Report and Written Opinion, European Patent Application No. 21214030.5, Apr. 4, 2022, 9 pages.
(Continued)

*Primary Examiner* — Christian C Boesen
(74) *Attorney, Agent, or Firm* — Fenwick & West LLP

(57) ABSTRACT

Provided herein are methods that enable parallel evaluation of multiple functional nucleic acids in individual cells or subpopulations of cells, in the context of incubation with other types of single cells. The key insight is concurrent measurement of polynucleic acids derived from small populations of at least two different cell types, such that function in one cell type is linked to the clonal identity of another cell. These methods simultaneously process thousands, millions, or more single cells or small populations of cells. The method integrates molecular, algorithmic, and engineering approaches. This invention has broad and useful application in a number of biological and medical fields, including immunology and drug discovery.

16 Claims, 7 Drawing Sheets

Specification includes a Sequence Listing.

Related U.S. Application Data continuation of application No. 16/443,381, filed on Jun. 17, 2019, now Pat. No. 11,111,490, which is a division of application No. 15/920,092, filed on Mar. 13, 2018, now Pat. No. 10,329,557.

(60) Provisional application No. 62/470,836, filed on Mar. 13, 2017.

(51) Int. Cl.
| | |
|---|---|
| *C07K 14/74* | (2006.01) |
| *C07K 16/00* | (2006.01) |
| *C12N 15/10* | (2006.01) |
| *C12Q 1/6806* | (2018.01) |
| *C12Q 1/6869* | (2018.01) |
| *C12Q 1/6888* | (2018.01) |
| *C40B 40/08* | (2006.01) |

(52) U.S. Cl.
CPC .......... *C07K 16/00* (2013.01); *C07K 16/005* (2013.01); *C12N 15/1065* (2013.01); *C12N 15/1075* (2013.01); *C12Q 1/6806* (2013.01); *C12Q 1/6869* (2013.01); *C12Q 1/6888* (2013.01); *C40B 50/06* (2013.01)

(56) References Cited

FOREIGN PATENT DOCUMENTS

| | | |
|---|---|---|
| WO | WO 2012/083225 A2 | 6/2012 |
| WO | WO 2012/148497 A2 | 11/2012 |
| WO | WO 2013/188872 A1 | 12/2013 |
| WO | WO 2014/004124 A2 | 2/2014 |
| WO | WO 2014/182197 A1 | 11/2014 |
| WO | WO 2015/031190 A1 | 3/2015 |
| WO | WO 2015/121434 A1 | 8/2015 |
| WO | WO 2015/164212 A1 | 10/2015 |
| WO | WO 2017/121832 A1 | 7/2017 |

OTHER PUBLICATIONS

International Search Report and Written Opinion, PCT Application No. PCT/US2018/022256, Jun. 22, 2018, 15 pages.
Keating, S.M. et al., "Capturing and Recreating Diverse Antibody Repertoires as Multivalent Recombinant Polyclonal Antibody Drugs," bioRxiv, preprint, Aug. 6, 2020, 78 pages.

Partition single target cells and inducer cells

Amplify and link identifyingtranscripts from inducer cells and activated transcripts from target cells Bulk sequence to identify inducer cell clones that activate target cells Readout of phenotype/function in target cells, linked to inducer single cell clonal identity.

SYSTEMS AND METHODS FOR MASSIVELY PARALLEL COMBINATORIAL ANALYSIS OF SINGLE CELLS

CROSS-REFERENCE TO RELATED APPLICATIONS

This application is a continuation of U.S. application Ser. No. 17/392,892, filed Aug. 3, 2021, which is a continuation of U.S. application Ser. No. 16/443,381, filed Jun. 17, 2019, which is a divisional of U.S. application Ser. No. 15/920,092, filed Mar. 13, 2018, which claims the benefit of U.S. Provisional Application No. 62/470,836, filed Mar. 13, 2017, each of which is hereby incorporated in its entirety by reference.

SEQUENCE LISTING

The instant application contains a Sequence Listing which has been submitted via Patent Center and is hereby incorporated by reference in its entirety. Said XML copy, created on Nov. 15, 2022, is named 53077US_XML_SequenceListing, and is 59,388 bytes in size.

BACKGROUND OF THE INVENTION

Biological cells are extremely diverse and have an enormous variety of biological functions. Functional analysis of cells is therefore a fundamental requirement in nearly any biological experiment. Because even genetically homogeneous populations of single cells have heterogeneous biological functions, biological experiments are best performed at the single cell level. However, single cell functional analysis is difficult, or impossible, using conventional methods.

Conventionally, functional analysis of "target cells" in response to exposure to "inducer cells" is carried out in tissue culture plates, for example, 6-well or 96-well plates. Target cells of interest are incubated with an inducer cell type, and then responses of the target cell are measured by assessing proteins, transcripts, or other kinds of biomarkers. Such methods are always carried out on bulk populations, i.e., hundreds, thousands, or millions of target cells are incubated with hundreds, thousands, or millions of inducer cells in order to determine target cell responses to the inducer cells. However, the target and inducer cell populations are inherently diverse genetically and phenotypically. Even cells with indistinguishable genome sequences may react differently to inducer cells, because of epigenetic differences, environmental differences, or reasons currently unknown to science.

Furthermore, methods that are sufficiently sensitive to do functional assays of a single target or inducer cell have not been available. Typically, quantitative differences in transcript counts between induced and non-induced cells is only 2-, 5-, or 10-fold, so highly sensitive methods are required. Similarly, methods that are sufficiently high-throughput to assay millions of single target or inducer cells in parallel have not been available. Additionally, functional analysis often requires concurrent measurement of transcripts in both the target and the inducer cells, for example, by concurrently measuring and sequencing transcripts in two cell types. Without such sensitive, high-throughput and combinatorial screening methods, it has been very difficult to understand functional responses of single target cells exposed to inducer cells, much less millions of single target or inducer cells in parallel.

SUMMARY OF THE INVENTION

The present invention relates to a high-throughput technology that can isolate single target cells with single inducer cells or populations of inducer cells, combined with a methodology for detecting the response of target cells to inducer cells (FIG. 1). In some embodiments, target cells and inducer cells are additionally incubated with "intermediary" cells, which are a type of induced cell. The present invention provides a highly sensitive method for detecting quantitative differences in transcript counts between induced and non-induced cells that are only 2-, 5-, or 10-fold. The present invention further enables a combinatorial measurement, such that diverse populations of target and inducer cells can be analyzed in millions of possible pairwise combinations. Some methods of the present invention involve quantification of polynucleic acids generated by tethering or linking polynucleic acids from more than one cell type. The methods provide a novel way of single cell functional screens that have not been possible in well-plate methods. The methods further provide the capability to trace functional readout to genetic differences in single target, intermediary, or inducer cells.

One aspect of the present invention relates to a method for functional analysis of biological cells, comprising the steps of (1) isolating into a monodisperse emulsion microdroplet a single target cell from a plurality of target cell clones of a first cell type and one or more inducer cells from a plurality of inducer cell clones of a second cell type; (2) incubating islolated cells in the monodisperse emulsion microdroplet, wherein the isolated cells comprise the single target cell and the one or more inducer cells; (3) introducing an aqueous solution containing a lysis reagent into said monodisperse emulsion microdroplets, thereby inducing lysis of the isolated cells; (4) capturing RNA released from the isolated cells on a solid surface; and (5) generating a library of hybridized polynucleic acids that comprise a transcript from the isolated cells, wherein the hybridized polynucleic acids are indicative of transcriptional change in the single target cell after the step of incubating the isolated cells.

In some embodiments, said hybridized polynucleic acids are further indicative of transcriptional change in the one or more inducer cells after the step of incubating the isolated cells. In some embodiments, said transcriptional change in the one or more inducer cells comprises increase of transcripts of a gene by less than tenfold.

In some embodiments, the plurality of target cell clones comprise more than 10,000 unique cell clones, wherein each target cell clone of the plurality of target cell clones is genetically distinct from each other. In some embodiments, the plurality of inducer cell clones comprise more than 10,000 unique cell clones, wherein each inducer cell clone of the plurality of inducer cell clones is genetically distinct from each other. In some embodiments, genetic diversity of the target cell clones is created by introducing a library of nucleic acid sequences into a population of at least 100,000 cells. In some embodiments, genetic diversity of the inducer cell clones is created by introducing a library of nucleic acid sequences into a population of at least 100,000 cells.

In some embodiments, RNA capturing is performed using oligonucleotides affixed to bead, each bead has a diameter less than 10 μm.

In some embodiments, the hybridized polynucleic acids are generated by overlap extension polymerase chain reaction. In some embodiments, the hybridized polynucleic acids are generated by first strand synthesis.

In some embodiments, the first cell type is a library of cells that express T cell receptors. In some embodiments, the first cell type is a library of cells that express antibodies. In some embodiments, the first cell type is a library of cells that express peptide:MHC. In some embodiments, the first cell type is a library of cells that express polynucleic acid barcodes.

In some embodiments, cells are isolated into emulsions using microfluidics.

Another aspect of the present invention relates to a composition comprising the library of hybridized polynucleic acids. In some embodiments, the composition comprises hybridized polynucleic acids of at least 10,000 unique sequences. In some embodiments, the composition comprises hybridized polynucleic acids of at least 1,000,000 unique sequences.

Another aspect of the present invention relates to a method for functional analysis of a population of cells comprising deep sequencing of the library of hybridized polynucleic acids.

Another aspect of the present invention relates to a composition comprising a library of recombinant proteins, generated from the composition comprising the library of hybridized polynucleic acids. In some embodiments, the library of recombinant proteins comprises T cell receptors. In some embodiments, the library of recombinant proteins comprises peptide:MHC. In some embodiments, the library of recombinant proteins comprises antibodies.

Another aspect of the present invention relates to a composition comprising a first probe and a second probe, wherein (1) the first probe comprises a first subsequence that is complementary to a transcript of an inducer cell of a first cell type and a second subsequence that is complementary to at least a part of the second probe, wherein the transcript is unique to the first cell type, and (2) the second probe comprises a third subsequence that is complementary to a different transcript of a target cell of a second cell type and a fourth subsequence that is complementary to at least a part of the first probe, wherein the amount of the different transcript changes when the target cell is incubated with the inducer cell.

In some embodiments, the transcript unique to said first cell type encodes a T cell receptor. In some embodiments, the transcript unique to said first cell type encodes an antibody. In some embodiments, the transcript unique to said first cell type encodes a peptide:MHC. In some embodiments, the transcript unique to said first cell type encodes a polynucleic acid barcode. In some embodiments, the transcript unique to said first cell type encodes a recombinant protein.

Another aspect of the present invention relates to a method for functional analysis of biological cells, comprising the steps of: (1) isolating into a monodisperse emulsion microdroplet a target cell from a plurality of target cell clones of a first cell type and one or more inducer cells from a plurality of inducer cell clones of a second cell type; (2) incubating isolated cells in the monodisperse emulsion microdroplet, wherein the isolated cells comprise the single target cell and the one or more inducer cells; (3) isolating RNA from the isolated cells; (4) generating a library of hybridized polynucleic acids using the composition comprising the first probe and the second probe, and (5) deep sequencing the library of hybridized polynucleic acids.

Another aspect of the present invention relates to a method for functional analysis of biological cells, comprising the steps of (1) isolating into a monodisperse emulsion microdroplet a single target cell from a plurality of target cell clones of a first cell type, one or more inducer cells from a plurality of inducer cell clones of a second cell type, and one or more intermediary cells from a plurality of intermediary cell clones of a third cell type; (2) incubating islolated cells in the monodisperse emulsion microdroplet, wherein the isolated cells comprise the single target cell, the one or more inducer cells, and the one or more intermediary cells; (3) introducing an aqueous solution containing a lysis reagent into said monodisperse emulsion microdroplets, thereby inducing lysis of the isolated cells; (4) capturing RNA released from the isolated cells on a solid surface; and (5) generating a library of hybridized polynucleic acids that comprise a transcript from the isolated cells, wherein the hybridized polynucleic acids are indicative of transcriptional change in the intermediary cells after the step of incubating the isolated cells.

In some embodiments, said hybridized polynucleic acids are indicative of transcriptional change in the one or more intermediary cells, after the step of incubating the isolated cells. In some embodiments, said transcriptional change in the one or more intermediary cells comprises increase of transcripts of a gene by less than tenfold.

In some embodiments, the plurality of target cell clones comprises more than 10,000 unique cell clones, wherein each target cell clone of the plurality of target cell clones is genetically distinct from the other cell clone of the plurality of cell clones. In some embodiments, the plurality of inducer cell clones comprises more than 10,000 unique cell clones, wherein each inducer cell clone of the plurality of inducer cell clones is genetically distinct from the other cell clone of the plurality of cell clones.

In some embodiments, genetic diversity of the target cell clones is created by introducing a library of nucleic acid sequences into a population of at least 100,000 cells. In some embodiments, genetic diversity of the inducer cell clones is created by introducing a library of nucleic acid sequences into a population of at least 100,000 cells.

In some embodiments, RNA capturing is performed using oligonucleotides affixed to beads, wherein each bead has a diameter less than 10 μm.

In some embodiments, the lysis reagent is a surfactant.

In some embodiments, the hybridized polynucleic acids are generated by overlap extension polymerase chain reaction. In some embodiments, the hybridized polynucleic acids are generated by first strand synthesis.

In some embodiments, the first cell type is a library of cells that express T cell receptors. In some embodiments, the first cell type is a library of cells that express antibodies. In some embodiments, the first cell type is a library of cells that express peptide:MHC. In some embodiments, the first cell type is a library of cells that transcriptionally express polynucleic acid barcodes.

In some embodiments, cells are isolated into emulsions using microfluidics.

Another aspect of the present invention relates to a composition comprising the library of hybridized polynucleic acids generated by the method described herein. In some embodiments, the composition comprises hybridized polynucleic acids of at least 1,000, 10,000, 100,000, or 1,000,000 unique sequences.

Another aspect of the present invention relates to a method for functional analysis of a population of cells by deep sequencing the library of hybridized polynucleic acids generated by the method described herein.

Another aspect of the present invention relates to a composition comprising a library of recombinant proteins, generated from the composition comprising the library of hybridized polynucleic acids generated by the method described herein. In some embodiments, the library of recombinant proteins comprises T cell receptors. In some embodiments, the library of recombinant proteins comprises peptide:MHC. In some embodiments, the library of recombinant proteins comprises antibodies.

Another aspect of the present invention relates to a composition comprising a first probe and a second probe, wherein (1) the first probe comprises a first subsequence that is complementary to a transcript of an inducer cell of a first cell type and a second subsequence that is complementary to at least a part of the second probe, wherein the transcript is unique to the first cell type; and (2) the second probe comprises a third subsequence that is complementary to a different transcript of an intermediary cell of a second cell type and a fourth subsequence that is complementary to at least a part of the first probe, wherein the amount of the different transcript changes when the intermediary cell is incubated with the inducer cell and a target cell.

In some embodiments, the transcript unique to said first cell type encodes a T cell receptor, an antibody, a peptide:MHC, a polynucleic acid barcode, or a recombinant protein.

Another aspect of the present invention relates to a method for functional analysis of biological cells, comprising the steps of (1) isolating into a monodisperse emulsion microdroplet a target cell from a plurality of target cell clones of a first cell type, one or more inducer cells from a plurality of inducer cell clones of a second cell type and one or more intermediary cells from a plurality of intermediary cell clones of a third cell type; (2) incubating isolated cells in the monodisperse emulsion microdroplet, wherein the isolated cells comprise the single target cell, the one or more inducer cells, and the one or more intermediary cells; (3) isolating RNA from the isolated cells; (4) generating a library of hybridized polynucleic acids using the composition comprising the first probe and the second probe; and (5) deep sequencing the library of hybridized polynucleic acids.

DETAILED DESCRIPTION OF THE INVENTION

Definitions

Figure 1:
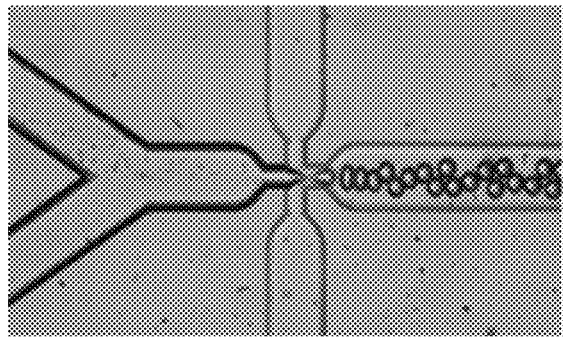
FIG. 1 is a diagrammatic workflow illustrating methods of the present invention for parallel functional analysis of single cells.
Figure 1:
Figure 1:
Figure 1:
Figure 1:

"Comprises." Consists at least of a list of components, i.e., encompasses all the elements listed, but may also include additional, unnamed elements.

"Cell." The cell is the basic structural, functional, and biological unit of all known living organisms. A cell is the smallest unit of life that can replicate independently.

"Transcriptome." Transcription is the first step of gene expression, in which a particular segment of DNA is copied into RNA (especially mRNA) by the enzyme RNA polymerase, to produce "transcripts". These transcripts have a variety of functions, comprising in particular providing the basis for translation of proteins inside cells. The "transcriptome" is the complete set of RNA transcripts present in a single cell or population of cells, or a sampling of transcripts that essentially comprises the complete set of RNA transcripts present in a single cell or population of cells.

"Transcriptional change." A change in the makeup of the transcriptome of a single cell or population of cells. Said transcriptional change may comprise a change in 1, 10, 100, 1,000, 10,000, or 100,000 transcripts. In some embodiments of this invention, a transcriptional change leads to changes in the function of the single cell or population of cells. In some embodiments of this invention, transcriptional change is induced in response to an external stimulus. For example, a T cell binding to its peptide:MHC antigen target may undergo transcriptional changes that produce proteins that lead to adaptive immune functions by the induced cell. In some embodiments of the invention, transcripts of interest are either up-regulated or down-regulated.

"Cell phenotype." A phenotype, or "cell type", is the composite of a cell's observable characteristics or traits, such as its morphology, development, biochemical or physiological properties, behavior, and products of behavior. In complex multicellular organisms, cells specialize into different cell types that are adapted to particular phenotypes. For avoidance of doubt, phenotype is often synonymous with cell "function", though changes in cell function do not necessarily require a change in phenotype. In mammals, major cell phenotypes include skin cells, muscle cells, neurons, T cells, B cells, plasma cells, plasmablasts, fibroblasts, stem cells, and others. Cell types may differ both in appearance and function, yet may be genetically identical. Cells are able to be of the same genotype (i.e., they are "clonal") but of different cell type due to the differential expression of the genes they contain. Cellular phenotype is the conglomerate of multiple cellular processes involving gene and protein expression that result in the elaboration of a cell's particular morphology and function. Many kinds of cells, such as immune cells, undergo phenotypic (i.e., functional) changes in response to external or internal stimuli. For example, memory B cells mature into plasmablasts upon stimulation with an antigen that binds to a B cell receptor on the B cell surface. In certain embodiments, RNA or protein expressed by a cell are used as biomarkers to identify a cell's phenotype.

"Cell clone." A cell with a unique genetic sequence. For example, two T cells that share a T cell receptor comprise a cell clone. In other embodiments, two cells that share an exogenous polynucleic acid barcode comprise a cell clone. Cell clones may or may not share a cell phenotype. For example, a CD4+ T cell may share a T cell receptor sequence with a CD8+ T cell. In certain embodiments, cell clones comprise the same cell type.

"Cell population." A group of cells or cell clones, comprising either multiple or single cell phenotypes. In certain embodiments, a cell population comprises 10,000 cell clones of one cell phenotype. In certain embodiments, a cell population comprises at least 10,000 single cells of one cell phenotype, wherein thousands of cell clones are present. In certain embodiments, a cell population comprises 10,000 single cells of 10, 20, 50, or 100 different cell types. For example, a tumor comprises millions of cells and dozens of cell types. Cell populations may comprise recombinant cells or primary cells.

"Functional analysis." Functional analysis involves determination or classification of a cell's function (i.e., phenotype) classically through experimental methods such as transcript expression analysis (e.g., quantitative PCR, DNA microarrays, RNA-sequencing), genome sequencing or genotyping (e.g., immune repertoire sequencing, quantitative PCR, whole genome shotgun sequencing), protein expression analysis (e.g., flow cytometry, ELISA), measurement of glycans (e.g., mass spectrometry), or measurement of any molecule that is a hallmark of the function of the cell. Because cellular function can be plastic, i.e., cellular phenotype can change in response to external stimuli, measurement of cellular function is particularly useful in screening for drugs or molecules that induce a specific biological function via cell functional changes. For avoidance of doubt, functional analysis is generally synonymous with phenotype analysis, although changes in cell function do not necessarily require a change in phenotype.

"Library." A pool of at least two polynucleic acids, cell clones, molecules, or proteins. In certain embodiments, a library is used to screen for biologically active proteins. In other embodiments, a library of cell clones is mixed with a drug, and then a biological assay is used to discern which cell clones are responsive to the drug. In other embodiments, a library of drugs is mixed with a single cell clone, and then a biological assay is used to discern which drugs cause a response in the cell clone. A library may comprise 100, 1,000, 10,000, 100,000, or 1 million different peptide:MHC targets, either as a polynucleotide library that codes for the peptide:MHC targets, or as cells engineered to express the peptide:MHC. In other embodiments, a library comprises 100, 1,000, 10,000, 100,000, or 1 million polynucleic acid barcodes, or cells engineered to express the polynucleic acid barcodes as RNA.

"Combinatorial." Relating to combinations of libraries of cells, proteins, polynucleic acids, or other types of molecules. A combinatorial functional analysis involves determining the function of random combinatorial pairs of components from such libraries. Because the components of the libraries are paired randomly, the number of possible combinations is the size of the first library multiplied by the size of the second library. For example, a library of 100 clones screened combinatorially against a library of 1,000 clones results in 100,000 theoretical combinations. Combinatorial functional analysis is useful for discovery of novel molecules or cellular interactions that induce cell functions of interest. In certain embodiments of the present invention, a genetically diverse library of cell clones is combinatorially screened against another diverse (for example, 100, 1,000, 10,000, 100,000, or 1 million clones) library of cell clones. In certain embodiments of the invention, a diverse library of cell clones is combinatorially screened against an oligoclonal (for example, fewer than 10) library of cell clones.

"Polynucleic acid." A polynucleic acid is a double or single stranded molecule of RNA or DNA, typically comprising 5, 10, 20, 50, 100, 1,000, 10,000, or more base pairs. Polynucleic acids may be synthetic, i.e., manufactured chemically from individual nucleotides, amplified, i.e., generated enzymatically from template nucleic acids using a polymerase, or purified from biological systems, i.e., extracted from cells or other biological materials. Polynucleic acids derived from, or detected in, biological cells, often serve as "biomarkers" that indicate functional differences between cells or populations of cells. Polynucleic acids have many sub-categories familiar to those skilled in the art. Complementary DNA, or cDNA, is DNA synthesized by using an enzyme such as reverse transcriptase to make cDNA from an RNA template. An "oligonucleotide" is a short (6-100 nucleotides) single stranded DNA or RNA sequence, typically manufactured synthetically by a commercial provider such as IDT DNA or ThermoFisher.

"Variable immune receptor." A variable immune receptor is any glycoprotein or glycoprotein complex that varies from cell to cell, or person to person. Variable immune receptors comprise critical innate and adaptive immune diversity required to identify invasive (or pathogenic) cells, viruses, bacteria, or other biologic material. In certain embodiments, an immune receptor that comprises the adaptive immune system, for example, an antibody or a T cell receptor. Most adult humans express billions of such variable receptors, in billions of different T cells or B cells. In other embodiments, an immune receptor that comprises immune system components that vary from individual to individual, for example, MEW or killer cell immunoglobulin-like (KIR) receptors.

"T cell receptor." The T cell receptor, or TCR, is a molecule found on the surface of T cells, or T lymphocytes, that are responsible for recognizing fragments of antigen as peptides bound to major histocompatibility complex (MEW) molecules. The TCR is a disulfide-linked membrane-anchored heterodimeric protein normally consisting of the highly variable alpha ($\alpha$) and beta ($\beta$) chains expressed as part of a complex with the invariant CD3 chain molecules. T cells expressing this receptor are referred to as $\alpha/\beta$ (or $\alpha\beta$) T cells, though a minority of T cells express an alternate receptor, formed by variable gamma ($\gamma$) and delta ($\delta$) chains, referred as $\gamma\delta$ T cells. Each chain is composed of two extracellular domains: Variable (V) region and a Constant (C) region, both of Immunoglobulin superfamily domain forming antiparallel beta-sheets. The Constant region is proximal to the cell membrane, followed by a transmembrane region and a short cytoplasmic tail, while the Variable region binds to the peptide:MHC complex. The variable domain of both the TCR $\alpha$-chain and $\beta$-chain each have three hypervariable or complementarity determining regions (CDRs), whereas the variable region of the $\beta$-chain has an additional area of hypervariability (HV4) that does not normally contact antigen and, therefore, is not considered a CDR. The residues are located in two regions of the TCR, at the interface of the $\alpha$- and $\beta$-chains and in the $\beta$-chain framework region that is thought to be in proximity to the CD3 signal-transduction complex. CDR3 is the main CDR responsible for recognizing processed antigen, although CDR1 of the alpha chain has also been shown to interact with the N-terminal part of the antigenic peptide, whereas CDR1 of the $\beta$-chain interacts with the C-terminal part of the peptide. CDR2 is thought to recognize the MHC. CDR4 of the $\beta$-chain is not thought to participate in antigen recognition, but has been shown to interact with superantigens. The constant domain of the TCR domain consists of short connecting sequences in which a cysteine residue forms disulfide bonds, which forms a link between the two chains. Each recombined TCR possess unique antigen specificity, determined by the structure of the antigen-binding site formed by the $\alpha$ and $\beta$ chains in case of $\alpha\beta$ T cells or $\gamma$ and $\delta$ chains on case of $\gamma\delta$ T cells. It is based mainly on genetic recombination of the DNA encoded segments in individual somatic T cells—either somatic V(D)J recombination using RAG1 and RAG2 recombinases or gene conversion using cytidine deaminases. The intersection of these specific regions (V and J for the alpha or gamma chain; V, D, and J for the beta or delta chain) corresponds to the CDR3 region that is important for peptide:MHC recognition. For avoidance of doubt, the term "TCR" throughout this disclosure embodies the full variety of possible recombinant derivative formats, and could be derived from any animal with an adaptive immune system, such as a human, mouse, camel, cow, bird, or fish. TCRs can be engineered into soluble form, for example by engineering chimeras with CD3 or Fc protein domains. These soluble TCRs then act as drugs by activating or antagonizing molecular targets of relevance to disease, for example, cancer.

"T cell." A T cell is a lymphocyte of a type produced or processed by the thymus gland and actively participating in the immune response. T cells play a central role in cell-mediated immunity. T cells can be distinguished from other lymphocytes, such as B cells and natural killer cells, by the presence of a T-cell receptor on the cell surface. The several subsets of T cells each have a distinct function. T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MEW class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, TH9, or TFH, which secrete different cytokines to facilitate different types of immune responses. Signaling from the APC directs T cells into particular subtypes. Cytotoxic T cells ($T_C$ cells, CTLs, T-killer cells, killer T cells) destroy virus-infected cells and tumor cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases. Memory T cells are a subset of antigen-specific T cells that persist long-term after an infection has resolved. They quickly expand to large numbers of effector T cells upon re-exposure to their cognate antigen, thus providing the immune system with "memory" against past infections. Regulatory T cells (suppressor T cells) are crucial for the maintenance of immunological tolerance. Their major role is to shut down T cell-mediated immunity toward the end of an immune reaction and to suppress autoreactive T cells that escaped the process of negative selection in the thymus. Suppressor T cells along with Helper T cells can collectively be called Regulatory T cells due to their regulatory functions. Two major classes of CD4+ Treg cells have been described—FOXP3+ Treg cells and FOXP3—Treg cells. The majority of human T cells rearrange their alpha and beta chains on the cell receptor and are termed alpha beta T cells (ab T cells) and are part of the adaptive immune system. Specialized gamma delta T cells, (a small minority of T cells in the human body, more frequent in ruminants), have invariant T cell receptors with limited diversity, that can effectively present antigens to other T cells and are considered to be part of the innate immune system. The genetic rearrangements and mutations that lead to TCR expression produces a T cell "clone". When the TCR engages with antigenic peptide and MHC (peptide:MHC), the T lymphocyte is activated through signal transduction, that is, a series of biochemical events mediated by associated enzymes, co-receptors, specialized adaptor molecules, and activated or released transcription factors. Immortal cell lines are often used experimentally to study T cell function, for example, the Jurkat cell line. In some embodiments of the invention, the TCRab expressed by Jurkat is knocked out, or deactivated, and a recombinant TCRab is introduced into the genome or transiently expressed through an expression construct. T cells are engineered into "cellular therapeutics" by introducing recombinant TCR constructs, for example through lentivirus transduction. T cell therapeutics are allogeneic or autologous, and are used to treat cancer and other kinds of serious disease. The engineered TCR is therefore a kind of drug that acts via a T cell.

"Antigen." The other member of a cognate pair for an antibody or T cell receptor. In certain embodiments, antibodies or T cell receptors specifically bind to a single antigen. In other embodiments, antibodies or T cell receptors bind to multiple antigens. Antibodies typically bind to proteins or glycoproteins in their native conformation, whereas T cell receptors require processed peptide antigens presented on the surface of an antigen presenting cell by an MHC. In certain embodiments, antigens are soluble, whereas in other embodiments, antigens are tethered to the surface of a cell.

"Antigen presenting cell." An antigen presenting cell (APC) displays an antigen peptide on its cell membrane. Antigen peptides are the product of proteolytic processing inside the APC. The antigenic peptides are then bound to a major histocompatibility complex (MHC) protein on the cell membrane of the APC. The bound complex is known as the peptide:MHC complex. T cell receptors do not bind antigen peptides directly, but instead require a peptide:MHC complex. In some embodiments, the peptide is derived from full proteins expressed by the APC. In other embodiments, the peptide is derived from viral proteins, and display of the viral-derived peptide is a hallmark of a cell infected by a virus. In certain embodiments, at least one plasmid encoding a full protein, partial protein, or polypeptide is introduced into a cell, and the plasmid drives expression of a recombinant peptide:MHC on the surface of the APC. In certain embodiments, APCs are incubated with peptides, peptide mixes, or proteins, resulting in a peptide:MHC on the APC membrane surface. In certain embodiments, cellular assays are performed with APCs. In certain embodiments, cellular assays are performed with APCs that are immortal cell lines (e.g., T2 cells), or primary cells (e.g., B cells).

"Antibody." An antibody (Ab), also known as an immunoglobulin (Ig), is a large, Y-shaped protein produced mainly by plasma cells that is used by the immune system to neutralize pathogens such as bacteria and viruses. The antibody recognizes a unique molecule of the harmful agent, called an antigen, via the Fab's variable region. Each tip of the "Y" of an antibody contains a paratope (analogous to a lock) that is specific for one particular epitope (similarly analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). Depending on the antigen, the binding may impede the biological process causing the disease or may activate macrophages to destroy the foreign substance. The ability of an antibody to communicate with the other components of the immune system is mediated via its Fc region (located at the base of the "Y"), which contains a conserved glycosylation site involved in these interactions. The production of antibodies is the main function of the humoral immune system. Antibodies can occur in two physical forms, a soluble form that is secreted from the cell to be free in the blood plasma, and a membrane-bound form that is attached to the surface of a B cell and is referred to as the B-cell receptor (BCR). The BCR is found only on the surface of B cells and facilitates the activation of these cells and their subsequent differentiation into either antibody factories called plasma cells or memory B cells that will survive in the body and remember that same antigen so the B cells can respond faster upon future exposure. In most cases, interaction of the B cell with a T helper cell is necessary to produce full activation of the B cell and, therefore, antibody generation following antigen binding. Soluble antibodies are released into the blood and tissue fluids, as well as many secretions to continue to survey for invading microorganisms. They are typically made of basic structural units—each with two large heavy chains and two small light chains. There are several different types of antibody heavy chains that define the five different types of crystallisable fragments (Fc) that may be attached to the antigen-binding fragments. The five different types of Fc regions allow antibodies to be grouped into five isotypes. Each Fc region of a particular antibody isotype is able to bind to its specific Fc Receptor (except for IgD, which is essentially the BCR), thus allowing the antigen-antibody complex to mediate different roles depending on which FcR it binds. The ability of an antibody to bind to its corresponding FcR is further modulated by the structure of the glycan(s) present at conserved sites within its Fc region. The ability of antibodies to bind to FcRs helps to direct the appropriate immune response for each different type of foreign object they encounter. Though the general structure of all antibodies is very similar, a small region at the tip of the protein is extremely variable, allowing millions of antibodies with slightly different tip structures, or antigen-binding sites, to exist. This region is known as the hypervariable region. Each of these variants can bind to a different antigen. This enormous diversity of antibody paratopes on the antigen-binding fragments allows the immune system to recognize an equally wide variety of antigens. The large and diverse population of antibody paratope is generated by random recombination events of a set of gene segments that encode different antigen-binding sites (or paratopes), followed by random mutations in this area of the antibody gene, which create further diversity. This recombinatorial process that produces clonal antibody paratope diversity is called V(D)J or VJ recombination. Basically, the antibody paratope is polygenic, made up of three genes, V, D, and J. Each paratope locus is also polymorphic, such that during antibody production, one allele of V, one of D, and one of J is chosen. These gene segments are then joined together using random genetic recombination to produce the paratope. The regions where the genes are randomly recombined together is the hypervariable region used to recognize different antigens on a clonal basis. Soluble antibodies are commonly used as therapeutic drugs, for example, rituximab, adalimumab, pembrolizumab, or trastuzumab. Antibodies are sometimes reformatted as Single Chain Fragment Variable (scFv), comprising a heavy and light chain fused together as a single protein, via a peptide linker. In some scenarios, scFv are reformatted as Chimeric Antigen Receptors (CARs), which are then engineered into T cells to create cellular therapeutics called CAR-Ts. For avoidance of doubt, the term "antibodies" throughout this disclosure embodies the full variety of possible recombinant derivative formats, and could be derived from any animal with an adaptive immune system, such as a human, mouse, camel, cow, bird, or fish.

"Natural killer cell." Natural killer cells (also known as NK cells, K cells, and killer cells) are a type of lymphocyte (a white blood cell) and a component of innate immune system. NK cells play a major role in the host-rejection of both tumors and virally infected cells. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation to kill cells that are missing "self" markers of MHC class 1. This role is especially important because harmful cells that are missing MHC I markers cannot be detected and destroyed by other immune cells, such as T lymphocyte cells. NK cells also kill cells by a mechanism called Antibody-Dependent Cell-mediated Cytotoxicity (ADCC), which starts with soluble antibodies binding to antigens on a target cell's surface. Antibodies that bind to antigens can be recognized by FcgRIII (CD16) receptors expressed on NK cells, resulting in NK activation, release of cytolytic granules and consequent cell apoptosis. This is a major cell killing mechanism of some monoclonal antibodies like rituximab, ofatumumab, and others. In certain embodiments, a cell line such as the NK-92 cell line is used in place of primary NK cells.

"Target." A biological molecule to which a drug binds in order to induce a pharmacological function. In certain embodiments, the target is a protein produced by a cell and expressed on the cell membrane. Targets also comprise nucleic acids, lipids, glycans, and glycoproteins. In certain embodiments, the target is an antigen, for example, a protein recognized by an antibody or a peptide:MHC recognized by a TCR.

"Target cell." A biological cell that expresses an antigen or target. In certain embodiments of the invention, the target or antigen is bound to the cell membrane of the target cell, and therefore exposed to the extracellular space. In certain embodiments of this invention, the target cell undergoes quantifiable changes in 1, 10, 100, or 10,000 mRNA transcripts as a result of the inducer cell interacting with the antigen or target on the surface of the target cell. In some embodiments of the invention, the quantifiable changes in the target cell are endogenous transcripts. In some embodiments of the invention, the quantifiable changes in the target cell are transcripts arising from recombinantly engineered "reporter" constructs that have been introduced into the target cell. In some embodiments of the invention, the reporter constructs contain promoters, enhancers, or other regulatory elements that induce transcription upon contact with signals resulting from the inducer cell contacting the target cell. In some embodiments of the invention, transcripts of interest are either up-regulated or down-regulated.

"Inducer cell." A biological cell that expresses a ligand or inducer molecule that binds to an antigen or target on the target cell. In certain embodiments of the present invention, the inducer cell secretes proteins or molecules that then bind to the target cell to induce quantifiable transcriptional changes. In other embodiments of the invention, proteins or molecules on the inducer cell surface bind to the target cell to induce quantifiable transcriptional changes. In certain embodiments, the inducing proteins or molecules comprise a single species, whereas in other embodiments of the invention, the inducing proteins or molecules comprise 2, 5, 10, 100, or 1,000 individual species. In certain embodiments of this invention, the inducer cell undergoes quantifiable changes in 1, 10, 100, or 10,000 mRNA transcripts as a result of the inducer cell interacting with the antigen or target on the surface of the target cell.

"Intermediary cell." A biological cell that responds functionally to the interaction between an inducer and a target cell, or to the interaction between a protein secreted by an inducer cell and proteins expressed by a target cell. In certain embodiments of this invention, the intermediary cell undergoes quantifiable changes in 1, 10, 100, or 10,000 mRNA transcripts as a result of the inducer cell interacting with the antigen or target on the surface of the target cell. In other embodiments of the invention, proteins or molecules secreted by the inducer cell surface bind to the target cell to induce quantifiable transcriptional changes in the intermediary cells. In some embodiments of the invention, the quantifiable changes in the intermediary cell are transcripts arising from recombinantly engineered "reporter" constructs that have been introduced into the intermediary cell.

"Synthetic polynucleic acid." Chemically or enzymatically synthesized RNA or DNA. To synthesize single-stranded RNA or DNA, or "oligonucleotides", the chemical synthesis process can be implemented as solid-phase synthesis using phosphoramidite method and phosphoramidite building blocks derived from protected 2'-deoxynucleosides (dA, dC, dG, and dT), ribonucleosides (A, C, G, and U), or chemically modified nucleosides, e.g. LNA or BNA. To obtain the desired oligonucleotide, the chemical building blocks can be sequentially coupled to the growing oligonucleotide chain in the order required by the sequence of the product. Typically, synthetic oligonucleotides are single-stranded DNA or RNA molecules around 15-25 bases in length. Synthetic polynucleic acids can be also generated by enzymatic methods, such as reverse transcription (RT), polymerase chain reaction (PCR), Gibson assembly, overlap extension PCR (OE-PCR), overlap extension RT-PCR (OE-RT-PCR), emulsion PCR, emulsion RT-PCR, emulsion OE-RT-PCR, emulsion OE-PCR, ligase chain reaction (LCR), hybridization, in vitro transcription, or any other cell-free molecular biological method that makes use of purified enzymes.

"Polynucleic acid barcode." A polynucleic acid barcode comprises a synthetic polynucleic acid that enables an experimentalist to identify a cell clone, i.e., a unique identifier. In some embodiments, barcodes are engineered into the genome of a cell, contained within an expression plasmid, or encoded into a recombinant or synthetic RNA sequence. In some embodiments, a barcode is attached to a solid surface, such as a one micron diameter magnetic bead. In some embodiments, populations of clones contain 10, 100, 1,000, 10,000, 100,000, or 1 million different barcodes. The barcodes can be sequenced through bulk sequencing, enabling high throughput combinatorial analysis of cell function.

"Reverse transcription." The process by which a reverse transcriptase (RT) enzyme is used to generate complementary DNA (cDNA) from an RNA template. Reverse transcriptase is commonly used in research to apply the polymerase chain reaction technique to RNA in a technique called reverse transcription polymerase chain reaction (RT-PCR). The classical PCR technique can be applied only to DNA strands, but, with the help of reverse transcriptase, RNA can be reverse transcribed into DNA, thus making PCR analysis of RNA molecules possible. Reverse transcriptase is used also to create cDNA libraries from mRNA.

"Polymerase chain reaction." Polymerase chain reaction (PCR) is a technique used in molecular biology to amplify a single copy or a few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target region along with a DNA polymerase, which the method is named after, are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations. PCR is not generally considered to be a recombinant DNA method, as it does not involve cutting and pasting DNA, only amplification of existing sequences. Almost all PCR applications employ a heat-stable DNA polymerase, such as Taq polymerase (an enzyme originally isolated from the bacterium Thermus aquaticus). This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the two DNA strands become templates for DNA polymerase to selectively amplify the target DNA. The selectivity of PCR results from the use of primers that are complementary to the DNA region targeted for amplification under specific thermal cycling conditions.

"Hybridization." Any process whereby two polynucleic acids are fused to form a single polynucleic acid molecule. Hybridization can occur by any process, natural or artificial, that results in two single-stranded polynucleic acids forming base pairing that result in a molecule that is at least partially double stranded. Base pairings conventionally occur through reverse complementarity, for example, guanine-cytosine, adenine-thymine, or adenine-uracil. In some embodiments, the hybridized base pairs are adjacent, for example, two single-stranded polynucleic acids that are each 100 nucleotides comprise 20 nucleotide subsequences that are reverse complements. Under the proper conditions, the two polynucleic acids would hybridize across these complementary nucleotide subsequences, forming a hybridized molecule. The amplification process called "overlap extension PCR" generates a plurality of fused, double stranded DNA products that result from the initial hybridization step between two polynucleotides that comprise complementary nucleotide subsequences.

"Microfluidics." Microfluidics is the science and technology of manipulating and controlling fluids, usually in the range of microliters ($10^{-6}$) to picoliters ($10^{-12}$), in networks of channels with lowest dimensions from tens to hundreds micrometers. Typically, fluids are moved, mixed, separated or otherwise processed. Numerous applications employ passive fluid control techniques like capillary forces. In some applications, external actuation means are additionally used for a directed transport of the media. Examples are rotary drives applying centrifugal forces for the fluid transport on the passive chips. Active microfluidics refers to the defined manipulation of the working fluid by active (micro) components such as micropumps or microvalves. Micropumps supply fluids in a continuous manner can be used for dosing. Microvalves can determine the flow direction or the mode of movement of pumped liquids. Processes which are normally carried out in a lab can be miniaturized on a single chip in order to enhance efficiency and mobility as well as to reduce sample and reagent volumes. Droplet-based microfluidics as a subcategory of microfluidics in contrast with continuous microfluidics has the distinction of manipulating discrete volumes of fluids in immiscible phases with low Reynolds number and laminar flow regimes. Two immiscible phases used for the droplet generation are termed as the continuous phase (medium in which droplets are generated) and dispersed phase (the droplet phase). The size of the generated droplets is mainly controlled by the flow rates of the continuous phase and dispersed phase, interfacial tension between two phases and the geometry used for the droplet generation.

"Microdroplet." A spherical, small volume of liquid, typically with volume less than one microliter. Microdroplets comprise aqueous-in-oil microdroplets and oil-in-aqueous microdroplets. A population of aqueous-in-oil microdroplets or oil-in-aqueous microdroplets comprise an "emulsion". Emulsions can be monodisperse, e.g., comprising microdroplets substantially the same volume, for example, varying by no more than 25% in diameter, or polydisperse, e.g., comprising microdroplets of a variety of volumes, for example, varying by >25% in diameter. Microdroplets are a means for performing high-throughput molecular, cellular, or biochemical experiments. Microdroplets serve to partition liquid reactions and therefore serve a similar function as a physical container. Millions or billions of microdroplets can be deposited in a small (for example, one milliliter) physical container, enabling very large combinatorial screening on single cells. In some embodiments of the present invention, monodisperse microdroplets are generated using microfluidics, i.e., "droplet microfluidics". In other embodiments of the invention, polydisperse microdroplets are generated using a shaking or mixing apparatus.

"Physical container." Physical containers used in molecular biology, cell biology, or biochemistry refer to tubes, plates, dishes, vials, or other formats comprising solid plastic, glass, polymer, or other solid material. In some embodiments, the physical container is inert, i.e., the container serves only to physically contain liquids for a molecular, cellular, or biochemical experiment. In some embodiments, reactive cells, molecules, proteins, drugs, or biochemical container are affixed to the physical container. Physical containers are a means for performing molecular, cellular, or biochemical experiments. To increase processing throughput, physical containers can be used together with robotic systems. In some embodiments, throughput is increased by using microfluidic chips that comprise physical containers, for example, nanoliter chambers on a glass, plastic, or PDMS microfluidic chip.

"Solid support." Solid supports used in molecular biology, cell biology, or biochemistry refer to beads or other geometric formats comprising solid plastic, glass, polymer, or other solid material. In some embodiments of the invention, reactive cells, polynucleic acids, proteins, or other molecules are affixed to solid supports. The solid supports are then introduced into a physical container or microdroplet, such that a biochemical, cellular, or molecular function is enabled. The solid supports can then be washed, or removed, simplifying multi-step laboratory processes. In some embodiments, the solid supports are magnetic beads of one, ten, or one hundred microns. In some embodiments, synthetic polynucleic acids are affixed to the magnetic beads, enabling purification of endogenous cellular polynucleic acids that are complementary to the synthetic polynucleic acids, also called "probes". In some embodiments, solid supports are beads coated with antibodies, which are then used to purify cells that express antigens with affinity for the antibodies.

"Bulk sequencing." Synonymous with deep sequencing, ultra-high throughput sequencing, massively parallel sequencing, and next-generation sequencing. Bulk sequencing comprises obtaining hundreds of thousands, millions, hundreds of millions, or billions of DNA sequence reads in parallel. In many embodiments, a diverse library of DNA is generated using methods such as PCR, RT-PCR, or hybridization and then a plurality of the library is sequenced using bulk sequencing. Methods can comprise sequencing by synthesis, nanopore sequencing, and pyrosequencing. As of 2017, commercial providers of bulk sequencing comprise Illumina, Pacific Biosciences, Oxford Nanopore, and Roche.

Overview of the Invention

One aspect of the present invention relates to concurrent measurement of polynucleic acids derived from at least two different cell types. The measurement can be performed in a massively parallel fashion on a small number of cells, or combinatorial screens can be performed on millions of different cell type combinations. In some embodiments, cells are combinatorially isolated into reaction containers, incubated to induce a biological response, and lysed to isolate RNA while retaining the combinatorial context. Transcripts from at least two different cell types can be physically linked by hybridization, and then the linked clones can be subject to deep sequencing on a massively parallel scale (FIG. 1).

Figure 2:
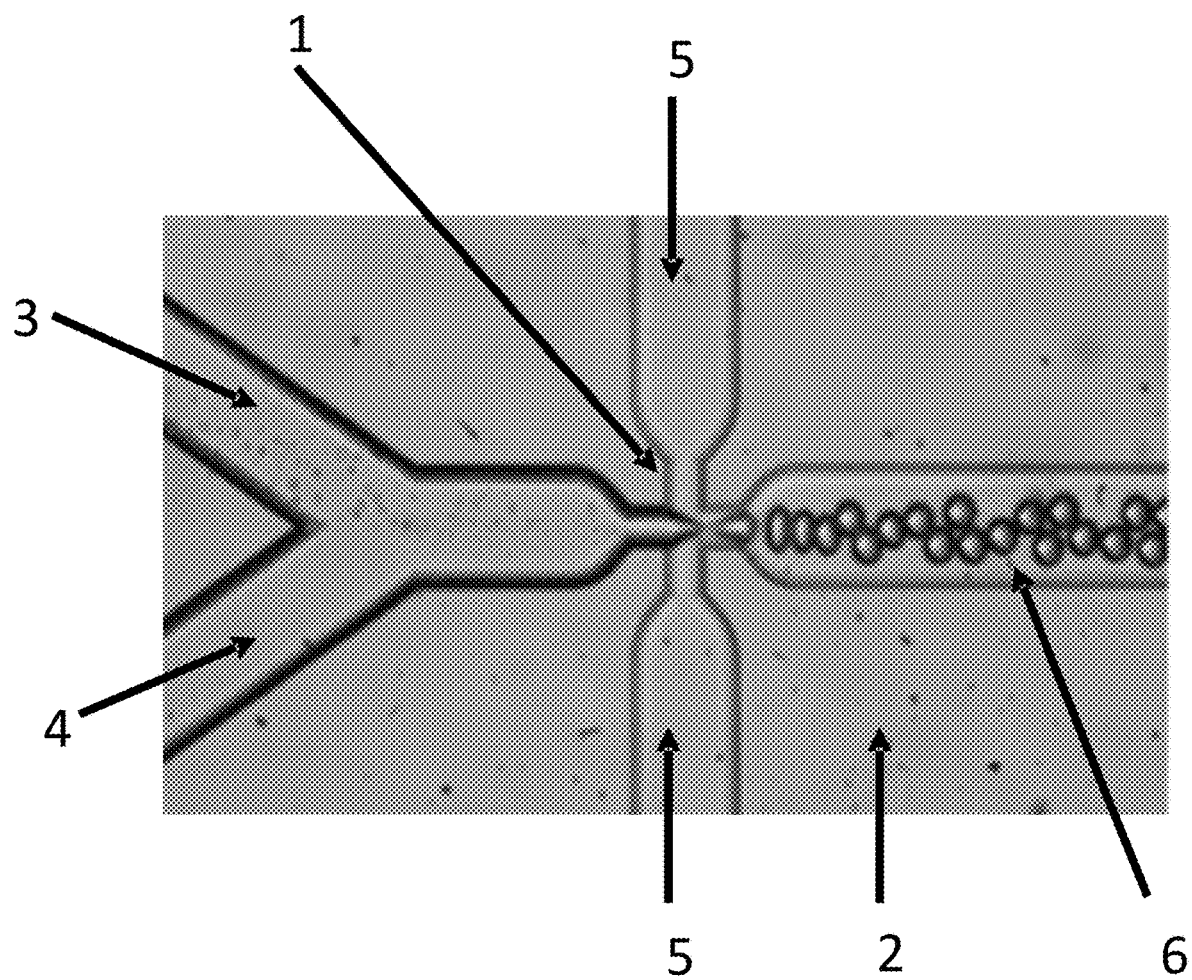
FIG. 2 shows cell encapsulation in emulsion microdroplets. 1. Channel constriction. 2. Glass into which microchannels are etched. 3. Cell input. 4. Lysis/RNA capture bead mix input. 5. Oil input. 6. Emulsion microdroplets.

The methods can involve isolation of single cells or subpopulations of cells into microemulsion droplets, gels, or microfluidic reaction containers. Millions of cells can be isolated or compartmentalized in a massively parallel manner to generate cell mixtures that represent genetically distinct pairwise combinations (FIG. 2).

The cell mixtures can comprise one or more target cells, one or more inducer cells, and/or one or more intermediary cells. The target cells can comprise populations of homogeneous cells or genetically distinct clones (for example, B cells, T cells, cells engineered with barcodes, cells engineered to express peptide antigens, primary cancer cells in single cell suspension). The inducer cells can comprise populations of homogenous cells or genetically distinct clones (for example, B cells, T cells, cells engineered with barcodes, cells engineered to express peptide antigens, NK cells). In some embodiments, intermediary cells are used, and the intermediary cells can comprise populations of homogeneous cells or genetically distinct clones (for example, NK cells).

In some embodiments, the target cells and inducer cells are mixed with a library of polynucleic acid barcodes affixed to a solid support (for example, beads, or a protein). In some embodiments, the cell mixtures are additionally incubated in the same microemulsion droplets, gels, or reaction containers with a stimulus, for example, a homogeneous population of cells, a library of reagents, or a single reagent.

Figure 3:
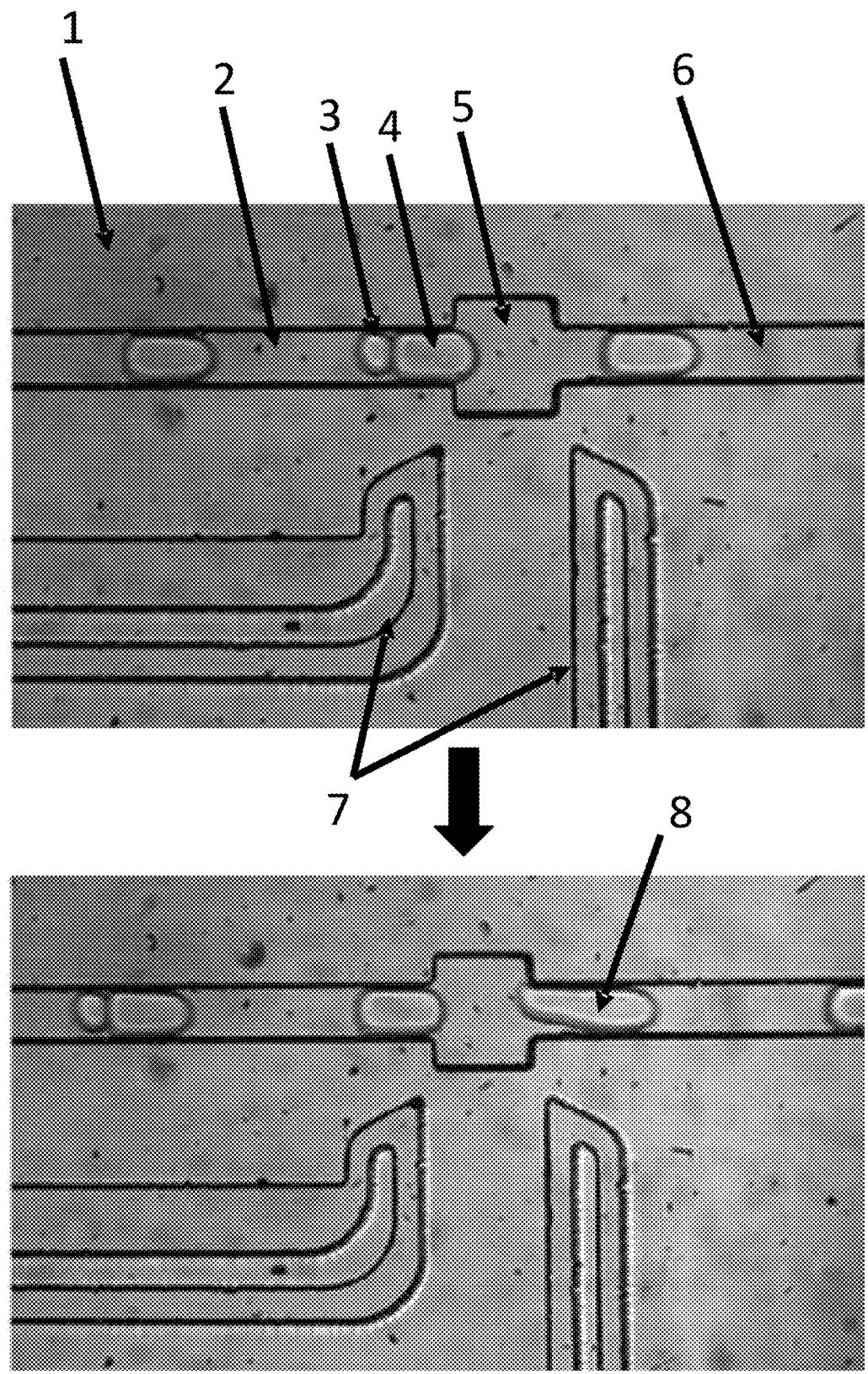
FIG. 3 shows droplet merging for cell lysis. 1. PDMS chip material. 2. Input channel. 3. Cell mixture input. 4. Lysis/bead mixture droplet. 5. Widened channel for droplet fusion. 6. Outlet channel. 7. Electrodes. 8. Fused microdroplet.

The mixtures of cells can be then lysed by introducing a reagent into the microemulsion droplets, gels, or microfluidic reaction containers. In some embodiments, this step comprises fusing microemulsion droplets containing the cells with microemulsion droplets containing the lysis reagent, thus preserving the compartmentalization of the cell mixtures (FIG. 3). After lysis, transcripts from the cell mixtures can be purified, for example, using beads coated with oligo-dT oligonucleotides.

Figure 4:
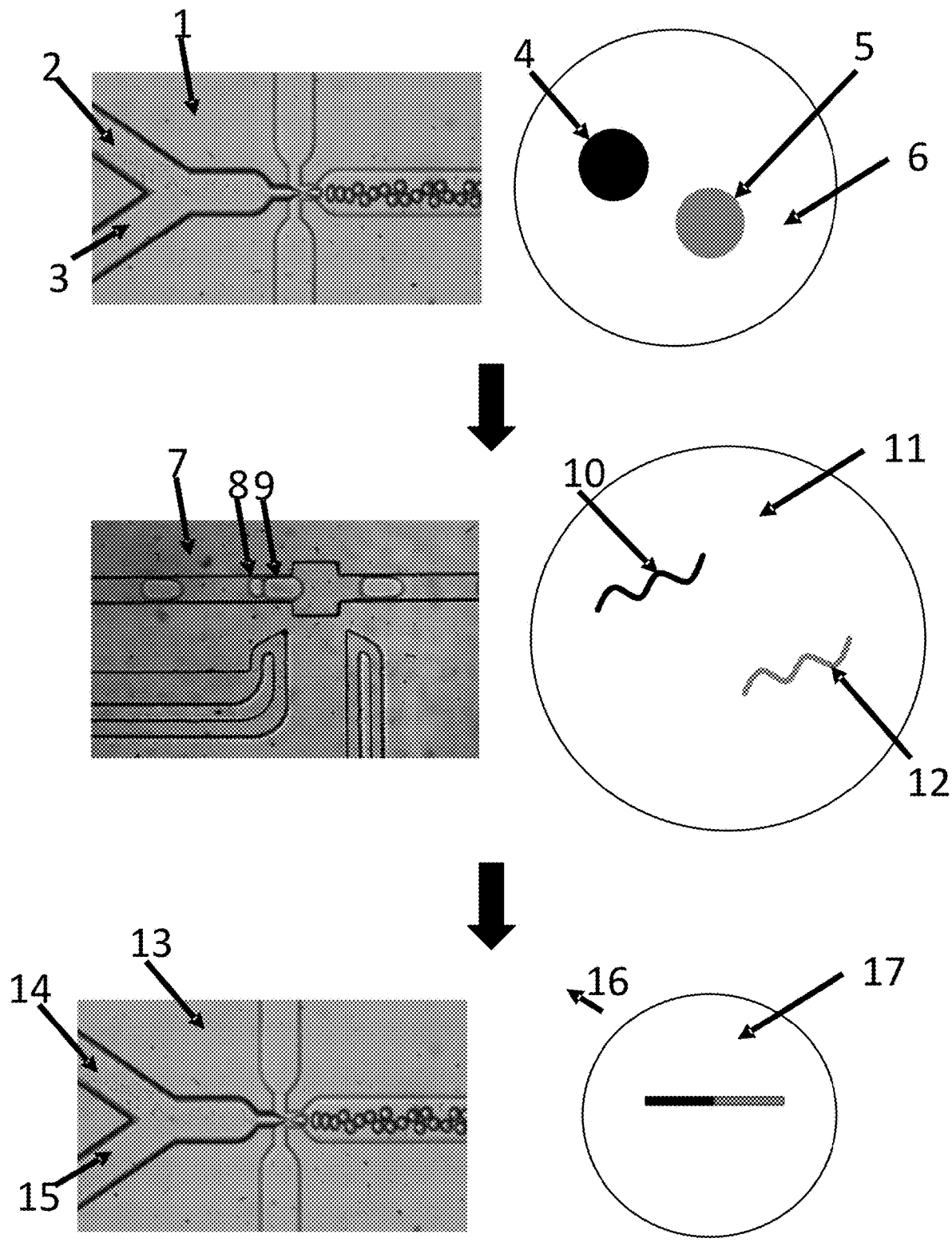
FIG. 4 is a diagrammatic workflow of the invention with at least two different single cells, with one clonal inducer cell and one target cell. 1. Cell mixture encapsulation emulsion microdroplet chip. 2. Clonal inducer cells. 3. Target cells. 4. Clonal inducer cell. 5. Target cell. 6. Cell culture media inside emulsion microdroplet. 7. Emulsion microdroplet fusion chip. 8. Cell mixture emulsion microdroplet. 9. Lysis/RNA capture bead mixture emulsion microdroplet. 10. Transcript traceable back to clonal inducer cell. 11. Emulsion microdroplet for binding transcripts to RNA capture beads. 12. Transcript from target cell, induced by inducer cell. 13. OE-RT-PCR emulsion microdroplet chip. 14. RNA-bound bead/OE-RT-PCR mix input. 15. RNA-bound bead/OE-RT-PCR mix input. 16. Amplicon comprising fusion between cDNA from transcript traceable back to clonal inducer cell and cDNA from transcript from target cell, induced by inducer cell. 17. OE-RT-PCR mix in emulsion microdroplet.
Figure 5:
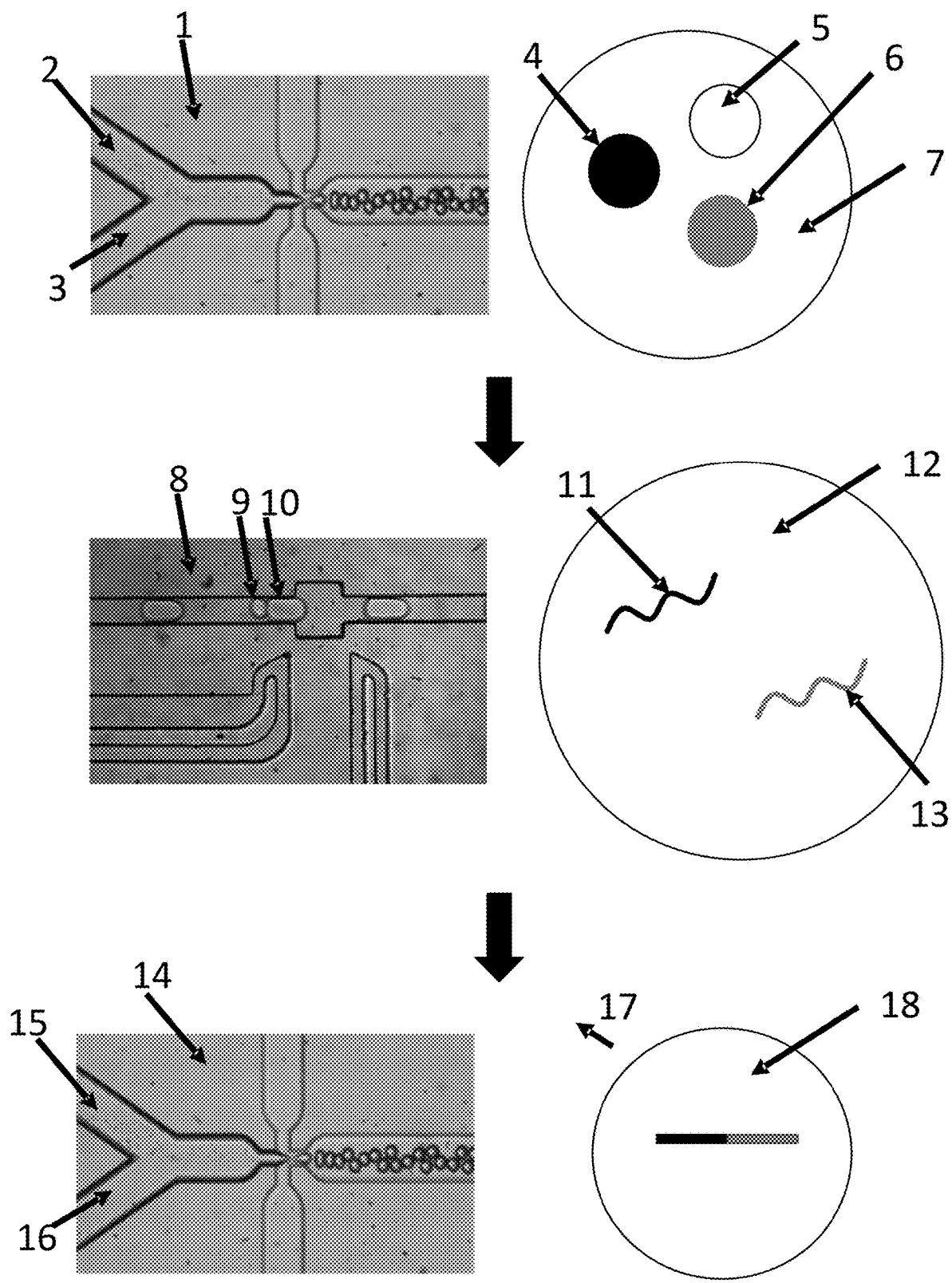
FIG. 5 is a diagrammatic workflow of linking transcripts from at least three different single cells, with three cell types, with a target cell, an inducer cell, and an intermediary cell. 1. Cell mixture encapsulation emulsion microdroplet chip. 2. Clonal inducer cells. 3. Target and intermediary cells. 4. Clonal inducer cell. 5. Intermediary cell. 6. Target cell. 7. Cell culture media inside emulsion microdroplet. 8. Emulsion microdroplet fusion chip. 9. Cell mixture emulsion microdroplet. 10. Lysis/RNA capture bead mixture emulsion microdroplet. 11. Transcript traceable back to clonal inducer cell. 12. Emulsion microdroplet for binding transcripts to RNA capture beads. 13. Transcript from target cell, induced by inducer cell. 14. OE-RT-PCR emulsion microdroplet chip. 15. RNA-bound bead/OE-RT-PCR mix input. 16. RNA-bound bead/OE-RT-PCR mix input. 17. Amplicon comprising fusion between cDNA from transcript traceable back to clonal inducer cell and cDNA from transcript from target cell, induced by inducer cell. 18. OE-RT-PCR mix in emulsion microdroplet.

In some embodiments, two or more polynucleotide targets are hybridized, such that polynucleic acids that differentiate clones are linked to RNA transcripts that indicate functional changes (FIGS. 4-5). The key insight is to fuse transcripts derived from at least two different cell types, for example, antibody target encoding transcripts and antibody-encoding transcripts derived from antibody-producing cells (wherein antibody-producing cells are the inducer cells). The hybridized polynucleic acid molecules can be then sequenced by bulk, or high-throughput, sequencing. Any high-throughput sequencing method known in the art can be employed.

Figure 6:
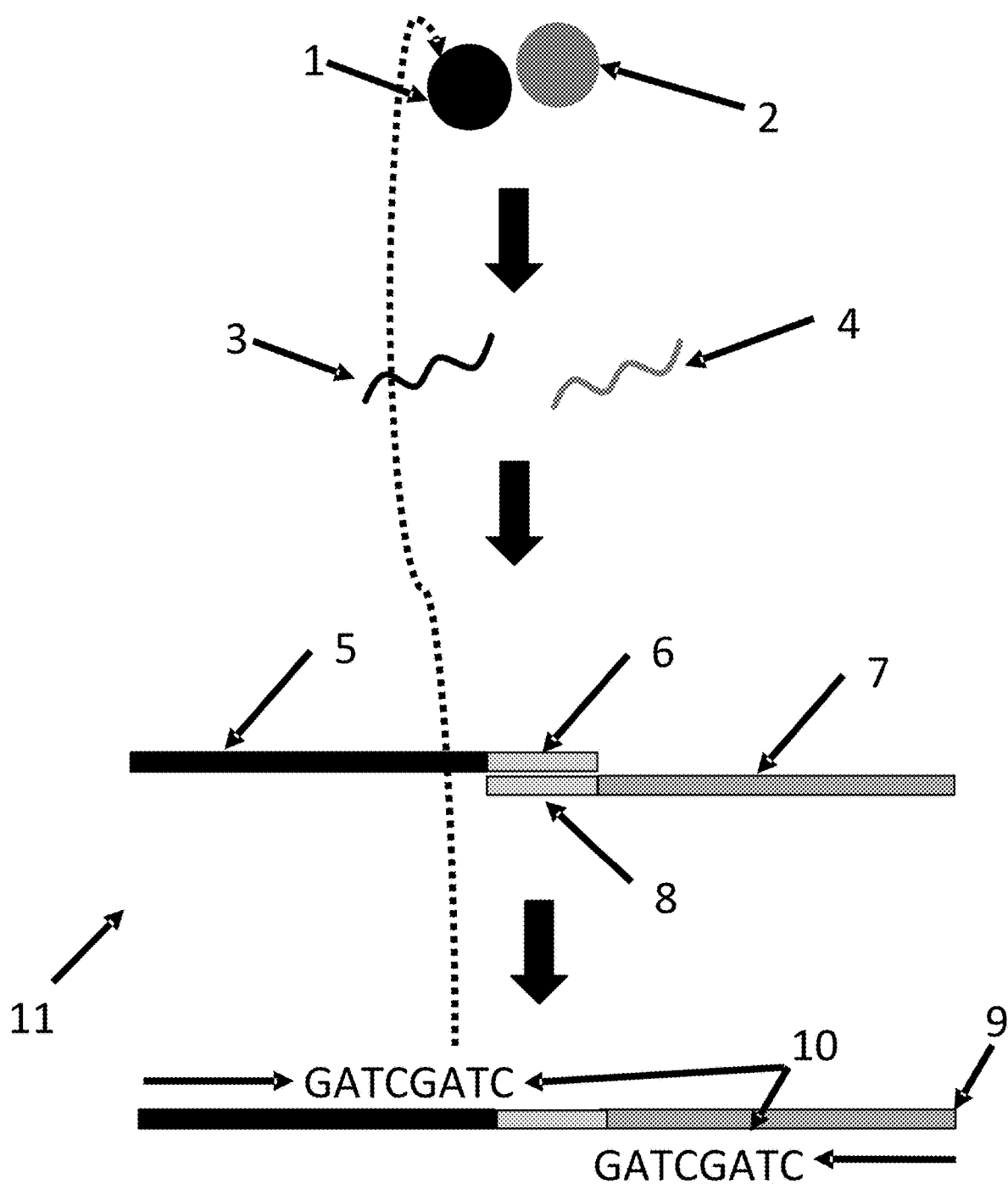
FIG. 6 is a diagrammatic workflow of linking transcripts from at least two different single cells, with a target cell and an inducer cell. 1. Inducer clone cell. 2. Target cell. 3. Inducer clone cell transcript. 4. Target cell transcript (induced phenotype, or indicative of induced transcriptional change). 5. Inducer clone cell transcript cDNA. 6. OE-RT-PCR linker sequence. 7. Target cell transcript (induced phenotype, or indicative of induced transcriptional change) cDNA. 8. OE-RT-PCR linker sequence. 9. OE-RT-PCR major, or linked, amplicon; fusion product of target and inducer cell transcript cDNAs. 10. Deep sequencing analysis of OE-RT-PCR fusion product amplicons. 11. Identification or trace back of OE-RT-PCR fusion product amplicon sequence to original inducer cell clone.
Figure 7:
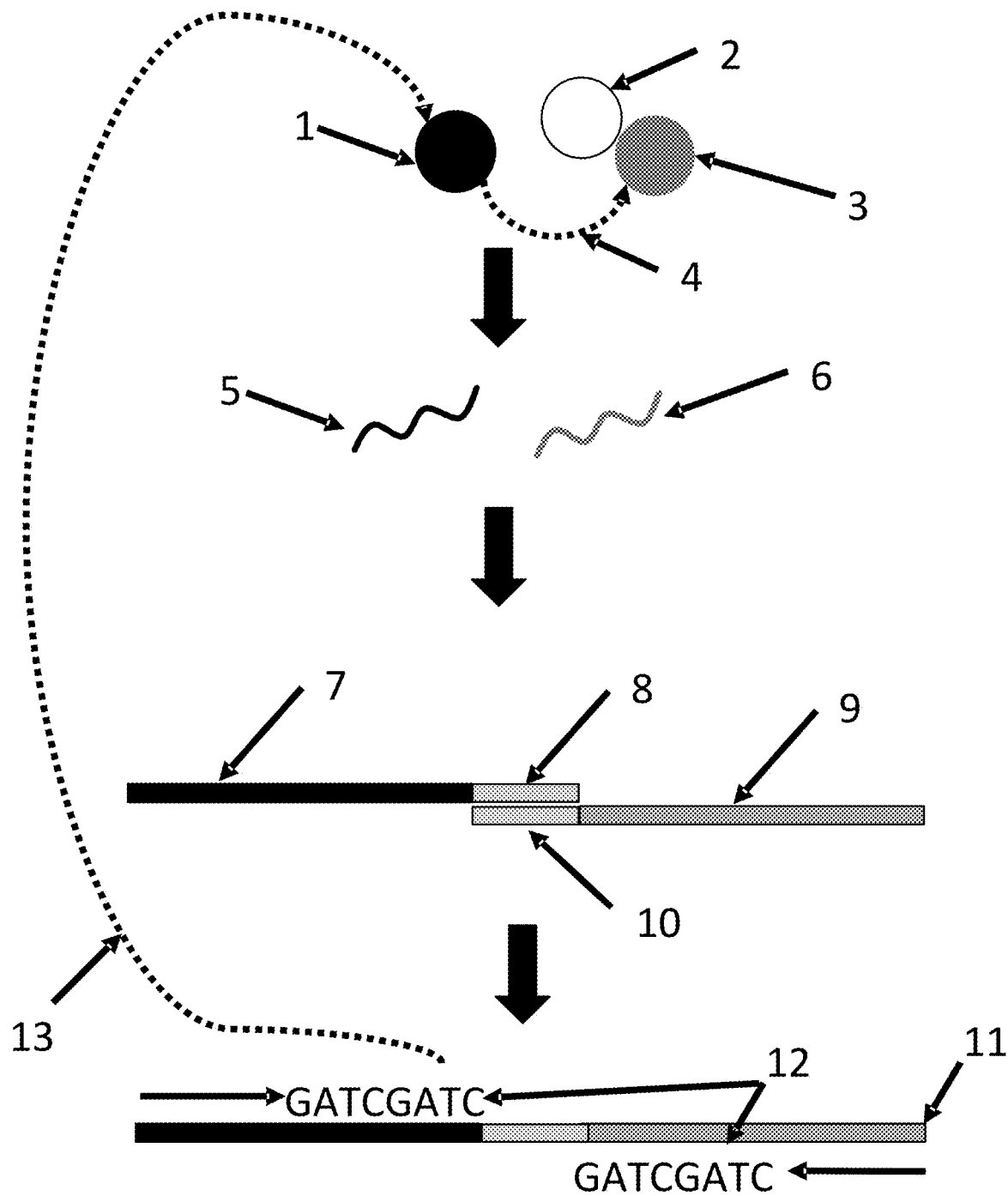
FIG. 7 is a diagrammatic workflow of linking transcripts from at least three different single cells, with a target cell, an inducer cell, and an intermediary cell. 1. Inducer clone cell. 2. Target cell. 3. Intermediary cell. 4. Action (via a molecule, e.g., a secreted antibody) of inducer cell on intermediary cell. 5. Inducer clone cell transcript. 6. Target cell transcript (induced phenotype, or indicative of induced transcriptional change). 7. Inducer clone cell transcript cDNA. 8. OE-RT-PCR linker sequence. 9. Target cell transcript (induced phenotype, or indicative of induced transcriptional change) cDNA. 10. OE-RT-PCR linker sequence. 11. OE-RT-PCR major, or linked, amplicon; fusion product of target and inducer cell transcript cDNAs. 12. Deep sequencing analysis of OE-RT-PCR fusion product amplicons. 13. Identification or trace back of OE-RT-PCR fusion product amplicon sequence to original inducer cell clone.

The bulk sequencing data can be subsequently analyzed algorithmically to determine which clones from the initial clone library demonstrate a functional change in response to the inducer cell stimulus, or stimuli (FIGS. 6-7). Sequencing of hybridized nucleic acid molecules from multiple cell types enables concurrent measurement of at least one transcript from each of at least two cell types, for example, an antibody target producing cell and an antibody-producing cell. Because of the extreme sensitivity of deep sequencing, transcript counts that are only 2-, 5-, or 10-fold different between induced and non-induced cells are detectable. Therefore, the method of the present invention can provide insight into the functional response of single target cells exposed to inducer cells, across millions of single target and inducer cells in parallel, and enables combinatorial functional screens that have never before been possible. In some embodiments, the hybridized polynucleic acids are further used to make libraries of recombinant proteins, which can be subsequently further screened for binding or function.

Provided herein are detailed descriptions of methods of the invention. Also provided herein are detailed descriptions of examples of embodiments of the invention, with particular application to immunology, drug discovery, drug development, and cancer biology.

Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Methods of the Invention

1) Generation of DNA Libraries

Some embodiments of the present invention involves generation of libraries of antibody clones by isolating B cells from mammalian donors, and then fusing the primary cells with myeloma cells, using techniques such as electrofusion, which are well known to those skilled in the art (Smith & Crowe, Microbiol Spectr. 2015 3(1): AID-0027-2014). The resulting cells, known as hybridomas, can be easier to rear in culture than primary cells. A variety of methods have been used to make T and B cell hybridomas, using primary cells from species comprising mice and humans. Using these methods, libraries of tens of thousands, hundreds of thousands, or millions of clones of cells that each express a unique TCR or antibody can be made.

Some embodiments of the present invention relate to methods of generating DNA libraries of a gene by isolating RNA from primary cells, for example, a tumor, a liver, a brain, blood, bone marrow, peripherial blood mononuclear cells, muscle tissue, cerebrospinal fluid, kidney tissue, lung lavage, lung tissue, immortal cell lines, skin tissue, or any other tissue or cell type. Reverse transcriptase can be used to synthesize cDNA from the RNA. For example, RNA is incubated with M-MuLV RT at 42° C. with an oligo-dT primer for one hour. In some embodiments, the oligo-dT primer is fused with a nucleic acid barcode sequence, flanked by universal amplification primers, which enables specific amplification of the barcode and trace back of the barcode to a cDNA sequence. This enables de-multiplexing of complex mixtures of clones. RT-based methods have the advantage of cheaply and quickly generating DNA libraries comprised of tens of thousands, hundreds of thousands, or millions of DNA clones in parallel. To recover a plurality of cDNA clones of interest, the full cDNA library can be subjected to PCR using a reaction comprising gene-specific primers, a thermostable polymerase such as Taq, and thermocycling consisting of denaturation (95° C. for 30 seconds), 30 cycles of amplification (95° C. for 15 seconds, 62° C. for 60 seconds, and 68° C. for 3 minutes), followed by a final extension at 68° C. for 5 minutes.

Some embodiments of the present invention relate to a method of generating DNA libraries of antibodies, TCRs, or any other kind of genetic sequence by DNA synthesis. In some embodiments, DNA sequencing data on TCR or antibody repertoires are obtained using methods known in the art, and then synthetic DNA libraries are engineered from sequences identified through bulk sequencing. In some embodiments, the synthesized DNA libraries comprise TCRs or antibodies known to bind to antigens of interest through methods comprising yeast display, mammalian display, or mammalian cell activation assays. DNA oligonucleotides can be designed such that they comprise libraries of overlapping, complementary sequences that hybridize when incubated together. Libraries of hundreds, thousands, tens of thousands, or hundreds of thousands of synthetic oligonucleotides can be manufactured by microfluidic or array-based methods, for example, by commercial providers such as Twist Bioscience, Agilent Technologies, or LC Biosciences. The libraries of oligonucleotides can be then assembled into DNA sequences of hundreds or thousands of nucleotides, using 5' exonuclease, DNA polymerase, and DNA ligase (e.g., "Gibson Assembly", Gibson et al. Nat Methods. 2009 May; 6(5):343-5). For example, T5 exonuclease, Taq polymerase, and Taq ligase are mixed in a reaction comprising overlapping oligonucleotides, nucleotides, DTT, $MgCl_2$, and buffer, and then incubated at 50° C. for 60 minutes. In some embodiments, Gibson Assembly is used to synthesize circular clones, for example, plasmid expression constructs. If the synthetic DNA is circular, the DNA can be transformed into bacteria to produce nanogram or more quantities of plasmid. Another method that generates linear synthetic DNA comprises mixing overlapping oligonucleotides and performing PCR using a thermostable polymerase. In order to make circular DNA, these linear PCR products can be then subcloned into plasmid expression constructs using methods comprising restriction enzymes and DNA ligase, Gibson Assembly, or blunt end cloning. Any of these DNA synthesis methods can be parallelized through 96-well plate, 384-well plate, microfluidic, or robotic processing systems.

DNA libraries of antibodies, TCRs, or any other target gene can be also generated through isolation and lysis of single cells, followed by nucleic acid amplification. Single B cells can be isolated into 96-well plates, and then heavy and light chain immunoglobulin transcripts can be linked using a method known in the art, for example, multiplexed "overlap extension" RT-PCR (Oleksiewicz EP1921144 B1). In overlap extension RT-PCR, or OE-RT-PCR, for immunoglobulin amplification from single cells, a pool of primers can be designed that bind and amplify all possible heavy chain genes and all possible light chain genes. The heavy chain primers can also comprise subsequences with complementarity to the light chain primers. During OE-RT-PCR, the complementary subsequences can hybridize and a polymerase can generate a fused polynucleic acid from hybridized single stranded heavy and light chain immunoglobulin. In this fashion, the single cell context of the heavy and light chain immunoglobulin can be maintained.

DNA libraries of antibodies, TCRs, or any other target gene can be generated by other methods, for example, those involving OE-RT-PCR and microfluidics from populations of more than ten thousand cells. One exemplary method disclosed in Johnson EP2652155, which is incorporated by reference in its entirety herein, involves use of a droplet microfluidic device. The droplet microfluidic device inputs an oil/surfactant mix, lysis and RNA capture mix, and a cell suspension and outputs single-cell emulsions into standard thermocycling microtubes. The oil/surfactant mix is based on mineral oil or fluorocarbon oil. The lysis and RNA capture mixture contains oligo-dT coated magnetic 1 μm beads that capture messenger RNA (mRNA) transcripts from the single cells. The cell encapsulation device is comprised of three pressure pumps, a microfluidic droplet chip, and imaging apparatus. The microfluidic chip is fabricated from glass and channels are etched to 50 μm×150 μm for most of the chip's length, and narrow to 55 μm at the droplet junction. Droplet size depends on pressure, but typically droplets of ~40 μm are optimally stable and appropriately sized for the single cell emulsions. Droplet generation rates also depend on pressure, but are typically up to 3 kHz and capture 3 million cells per hour. Cell lysis methods comprise surfactant based methods, for example Triton X-100, NP-40, Tween 20, Tween 80, or SDS. The emulsions are incubated at 50° C. for 30 minutes, and then the beads are extracted from the emulsion using a solvent such as ethyl acetate. Next, the mRNA-bound beads are injected back into emulsions for OE-RT-PCR, using microfluidic chips similar to the cell encapsulation chips described above. For example, to generate TCRαβ libraries, independent TCRα and TCRβ minor amplicons are generated in multiplex; these are then fused to generate a single major amplicon comprised of both TCRα and TCRβ. The TCRαβ primer pool includes a universal primer for β constant (Cβ) and α constant (Cα) regions. This abrogates the need for a large pool of J region primers. Additionally, the C region primers are designed to either capture the endogenous C region genotypes or isotypes, or the primers are designed to ignore endogenous C region genotypes or isotypes. The TCRαβ primer pool also includes 43 primers that bind to all possible V segments for TCRαβ and TCRβ. Thus, the primers amplify across the full variable region of each monomer to produce 450 bp minor amplicons. Exemplary primers for TCRβ V gene is provided herein as SEQ ID NO: 17-19, an exemplary primer for TCRβ C gene is provided herein as SEQ ID NO: 20, exemplary primers for TCRα V gene are provided as SEQ ID NO: 21-23 and an exemplar primer for TCRα C gene is provided herein as SED ID NO: 24. The bead emulsions are then subjected to OE-RT-PCR using a reaction comprising an RT, gene-specific primers, a thermostable polymerase such as Taq, and thermocycling consisting of reverse transcription (42° C. for 60 minutes), denaturation (95° C. for 30 seconds), 30 cycles of amplification (95° C. for 15 seconds, 62° C. for 60 seconds, and 68° C. for 3 minutes), followed by a final extension at 68° C. for 5 minutes. Because a plurality of droplets contains only a single mRNA-bound bead, the native TCRαβ pairing of the input T cell is maintained in the TCRαβ linkage library. Similar methods can be used to generate linked heavy and light chain immunoglobulin DNA libraries. For example, immunoglobulin primer sets comprising a polynucleotide of any of SEQ ID NO: 1-8 can be used. SEQ ID NO: 1-3 provide exemplary primer sequences for IGG V gene, SEQ ID NO: 4 provides an exemplary primer sequence for IGG C gene, SEQ ID NO: 5-7 provide exemplary primer sequences for IGK V gene, and SEQ ID NO: 8 provides an exemplary primer sequence for IGK C gene. Primers for the immunoglobulin C regions are either isotype-specific, genotype specific, or are universal primers designed amplify any C region sequence. In some embodiments, the TCR or immunoglobulin subunits are linked with a polynucleic acid sequence encoding a porcine teschovirus-1 (P2A) amino acid sequence. In some embodiments, the TCR or immunoglobulin subunits are linked with a polynucleic acid sequence encoding a Gly-Ser peptide linker. In some embodiments, the TCR or immunoglobulin subunits are linked with a polynucleic acid sequence encoding an Internal Ribosome Entry Site (IRES). In other embodiments, the TCR or immunoglobulin subunits are linked with artificial linker sequences with no significant homology to any known endogenous sequences.

The DNA libraries of linked TCRαβ or heavy and light chain immunoglobulin can be converted to recombinant expression constructs using methods known in the art, for example, the method described in Johnson U.S. Pat. No. 9,422,547 B1, which is incorporated by reference in its entirety herein. The exemplary method described in Johnson U.S. Pat. No. 9,422,547 B1 uses nested outer PCR primers to add adapters with overhangs for Gibson Assembly to the 5' and 3' ends of the amplicon library. Primers for the C regions can be either isotype-specific, genotype specific, or are primers designed amplify any C region sequence. T5 exonuclease and Taq ligase are mixed in a reaction comprising the TCRαβ or immunoglobulin insert, a linearized plasmid backbone with subsequences complementary with the insert, DTT, $MgCl_2$, and buffer, and then incubated at 50° C. for 60 minutes. The plasmid backbone comprises a promoter, a poly(A) signal sequence, and C region sequence not amplified through OE-RT-PCR. The C region matches the isotype or genotype of the linked amplicon, or is designed to fuse the amplicon with a non-native isotype or genotype. The library is then transformed into *E. coli* and spread on LB-ampicillin plates. The plasmid library is then purified with a Maxi prep kit. The purified Maxi prep library contains tens of thousands, hundreds of thousands, or millions of clones. Some workflows require a second round of Gibson Assembly. For example, if the one or both of the full C regions are not amplified in the original OE-RT-PCR, it may be necessary to clone a C region between the TCRαβ or heavy and light chain immunoglobulin. In some embodiments, a promoter, P2A, or IRES sequence is cloned at the same time. The inserted sequences are synthesized by assembling a pool of oligonucleotides using Gibson Assembly or PCR, and then Gibson Assembly can be used to insert the polynucleic acid insert into the plasmid library. This reaction can be performed on tens of thousands, hundreds of thousands, or millions of clones in parallel. The final result is a library of tens of thousands, hundreds of thousands, or millions of TCRαβ or heavy and light chain immunoglobulin clones that express fully functional proteins, which retain the native pairing of the original single cell inputs.

In some embodiments, single cell amplification methods are used to generate single cell cDNA libraries for any transcript, set of transcripts, or full single cell transcriptomes using various methods for nucleic acid barcoding, for example, as described in Johnson U.S. Ser. No. 15/159,674, which is incorporated by reference in its entirety herein.

The exemplary method disclosed in Johnson U.S. Ser. No. 15/159,674 comprises delivering a clonal polynucleic acid barcode with a single cell into a reaction vessel, microfluidic chamber, or an emulsion microdroplet. One method is to affix polynucleic acids that comprise barcodes to solid supports comprising spherical beads with 1 μm, 5 μm, or 10 μm diameter, made of magnetic material to facilitate nucleic acid purification. Oligonucleotides are modified with NH2 and affixed to epoxy silane or isothiocyanate coated glass beads, or oligonucleotides are disulfide modified and attached to mercaptosilanized glass supports. For droplet encapsulation, bead solutions are mixed with cells, and then diluted such that a plurality droplets contain a single cell and a single bead. Because such methods result in a plurality of empty droplets or droplets with only a single bead or only a single cell, in some methods, cells and beads are first encapsulated into droplets in separate streams or separate devices, and then the cell- and bead-containing droplets are fused to generate a plurality of droplets that contain a single cell and a single bead. Depending on the application, a plurality of single cells can be encapsulated with multiple barcoded beads. Such methods enable trace back of individual barcodes to single cells, even if there are multiple barcodes for a plurality of single cells. Other methods comprise biotin-streptavidin and covalent conjugation chemistries. Another method is to affix polynucleic acids that comprise barcodes to antibodies, which are bound to cells prior to delivering the cells to reaction vessels, microfluidic chambers, or emulsion microdroplets. Methods for conjugating antibodies to nucleic acids available in the art can be employed, for example, biotin-streptavidin or covalent conjugation chemistries. Cell lysis methods can comprise surfactant based methods, for example Triton X-100, NP-40, Tween 20, Tween 80, or SDS. In some embodiments, the emulsions are incubated at 50° C. for 30 minutes, and then the beads are extracted from the emulsion using a solvent such as ethyl acetate. Next, the RNA-bound beads are recovered from the emulsion and then amplified in droplets or reaction vessels using the methods described above, with some modifications specific to nucleic acid barcoding. In nucleic acid barcoding, the first strand cDNA can be labeled with the nucleic acid barcode fused to the transcript-specific first strand primer. Universal primers 5' to the nucleic acid barcode can be used in PCR to amplify a plurality of barcoded RT-PCR amplicons. Alternatively, RNA can be primed and amplified separately from the barcode sequence, and then the barcode and cDNA amplicons can be fused in an overlap extension PCR inside of emulsion microdroplets. Alternatively, first strand cDNA barcoding can be effected with RT in the lysis mixture, without the requirement to inject RNA-bound beads for an RT-PCR amplification. In these methods, the cDNA-bound beads can be extracted from the emulsion and the barcoded cDNA can be subjected to "bulk" PCR, i.e., PCR without an emulsion. The final result of any of these methods can be a library of tens of thousands, hundreds of thousands, or millions of barcoded cDNA clones that express fully functional proteins, which enable trace back of cDNAs with the same barcode back to a single originating cell. The cDNAs are not necessarily full length, for example, peptide:MHC complexes do not require full cDNA for functional analysis.

In some embodiments, a target library comprises NY-ESO-1 target sequence (SEQ ID NO: 13), or MART-1 target sequence (SEQ ID NO: 16), engineered into two different mammalian clones.

Once reformatted as circular plasmids, libraries of cDNAs can be introduced into mammalian cells for protein production. For example, TCRαβ expression constructs can be packaged into lentivirus or any other vector known in the art and then used to transduce the Jurkat J.RT3-T3.5 cell line (ATCC) or other cells, which lack TCRβ expression and thus have no cell surface TCR. In one specific embodiment, first, starting with the TCRαβ plasmids Vesicular Stomatitis Virus G (VSV-G) pseudotyped lentiviral particles are generated using the 3rd generation ViraSafe Lentiviral Packaging System (Cell Biolabs) and Lenti-Pac 293Ta cells (GeneCopoeia). Lentiviral copy number can be determined using the Lenti-X qRT-PCR Titration Kit (Clontech) to normalize transduction. In the exemplary embodiment, $10^5$ or $10^6$ J.RT3-T3.5 cells are transduced with a library of lentiviral construct and then selected with Puromycin for 14 days. In the exemplary embodiment, FACS analysis demonstrates 15-30% transduction efficiency. In other specific embodiment, CHO Flp-In (provided commercially by Life Technologies) cells are transfected for targeted genome integration of heavy and light chain immunoglobulin libraries. Whereas lentivirus integrate randomly into a mammalian genome, plasmids engineered for Flp-In will only integrate at an FRT site in a cell's genome. CHO Flp-In cells have been previously engineered to contain an FRT site at a single location in the genome. To engineer a library of antibody-expressing cells, a ratio of 2:1 Flp recombinase vector to antibody plasmid library is used to electroporate four million CHO Flp-In cells in Ingenio buffer (Minis Bio). After two days in growth medium without selection, the growth medium is supplemented with 600 g/mL hygromycin, which selects against cells lacking stable integrants. After three weeks, colonies are counted, such that in a successful experiment, approximately ~1% of the electroporated cells result in stable integrants. CHO Flp-In cells are engineered with secreted or membrane-bound antibodies, depending on the requirements of downstream experiments. Other methods known in the art can be used to engineer protein expression constructs into the genomes of mammalian cells, for example, random integration of retroviruses, CRISPR/Cas9, Transcription Activator-Like Effector Nucleases (TALENs), and zinc finger nucleases. Any of the methods can be employed to obtain a library of cell clones that express thousands, tens of thousands, hundreds of thousands, millions, or hundreds of millions of different transcript and protein sequences of interest. In some embodiments, an example target library comprises NY-ESO-1 target sequence (SEQ ID NO: 13), or MART-1 target sequence (SEQ ID NO: 16), engineered into two different mammalian clones.

2) Preparation of Target Cells, Intermediary Cells, and Inducer Cells for Functional Assays Some aspects of the present invention relate to a method of partitioning single clonal cells with their target cells, or single clonal cells with intermediary cells and target cells. To facilitate high-throughput analysis, partitioning of cells can be achieved by encapsulation into aqueous-in-oil droplets using droplet microfluidic chips. Any microfluidic chips known in the art can be employed. For example, microfluidic chips that can be used for various embodiments of the present invention include, but not limited to those fabricated from glass, plastic, PDMS, or other polymers. One specific embodiment employs a microfluidic chip fabricated from glass, with channels etched to 50 μm×150 μm for most of the chip's length, and which narrow to 55 μm at the droplet generation junction. Fluid is pumped through the microfluidic chips using pressure pumps or syringe pumps. Cells are injected into droplets in two streams. For example, APCs are injected in one stream and TCR-expressing cells are injected in a second stream. Typically, TCR-expressing cells are injected at 10,000-20,000 cells per microliter, and APCs are injected at a slightly lower concentration, for example, 2,000-5,000 cells per microliter, such that most droplets that contain an APC contain only a single APC. The droplets containing the cell mixtures are in the range of 20-200 μm. The ratio of inducer to target cells varies from application to application, but it is desirable for the partitions to contain single inducer cells, enabling detection of functional interaction between a clonal cell and its target. In some embodiments, cells are encapsulated into gels rather than aqueous solutions. For example, agarose gels are used to embed and encapsulate cells of interest. Reaction vessels such as 96-well plates, 384-well plates, or microfluidic chamber chips can be used if the size of the clone library does not exceed 10,000 genetically distinct clones. Flow cytometry or manual pipetting can be used to distribute cells into 96-well plates. Cells can be distributed into microfluidic vessel chips (for example, from vendors such as Fluidigm) using pressure pumps or syringe pumps, and microfluidic microwell valves are used to capture cells into microfluidic chambers. Regardless of whether droplets or reaction vessels are used to partition mixtures of cells, the mixtures of cells can be incubated in a way that enables the inducer cells to induce transcriptional changes in the target cells and/or intermediary cells, for example, RPMI, DMEM, or IMDM, supplemented with 10% fetal calf serum (FCS), at 37° C. in a tissue culture incubator.

In some embodiments, a glass microfluidic chip is used to inject CHO cells into 35 μm radius droplets in RPMI with 10% FCS, with the oil phase comprising fluorocarbon oil and surfactant. Sytox Orange and Calcein-AM (ThermoFisher) are included in the media to stain for dead and live cells, respectively. We then overlay the emulsions with a layer of mineral oil to prevent fluorocarbon oil evaporation but enable gas exchange. The emulsions are then incubated in a microcentrifuge tube in a conventional tissue culture incubator at 37° C., 5% $CO_2$. We then use our fluorescent microscope to assess live/dead staining. In a typical experiment, 49/50 cells are still alive after 16 hours, and 45/50 cells are still alive after 24 hours. After 72 hours, >85% of cells are still intact, but no longer fluoresce sufficiently for live/dead determination.

Target and inducer cells incubated in emulsion microdroplets can be lysed to generate a plurality of polynucleic acids that fuse clonal sequences from the inducer cell with induced transcripts from the target cell. Such protocol can retain proper pairing between inducer clones and target cells. Cell culture media which is optimal for functional studies is not necessarily optimal for cell lysis and enzymatic polynucleic acid amplification. To address this issue, a droplet microfluidic chip design that fuses cell-containing droplets with lysis/bead mix can be used.

In some embodiments, droplet fusion is driven by interfacial forces where two droplets have a larger interfacial area than a single droplet of the same volume. To achieve this situation, the continuous phase separating the two droplets can be removed. For example, when the two droplets have close contact with each other, a thin liquid bridge forms between the two droplets due to molecular attractions between the droplets. The curvature meniscus formed around the bridge creates an imbalance of surface tension which quickly merges the two droplets. Fusion of emulsion microdroplets is either passive (i.e., not requiring outside energy) or active (i.e., requiring outside energy) (as summarized, for example, in Xu *Micro and Nanosystems* 2011 3:131-136). Passive methods can rely on the structure of the microchannel or surface properties of the microchannel. On the other hand, active droplet coalescence can use energy supplied by an outside source, for example, by applying a magnetic, electric, or temperature field.

In one exemplary embodiment, one chip design, manufactured in PDMS, comprises two aqueous input channels and two oil input channels. The aqueous/oil inputs are in two pairs, i.e., one aqueous inlet is paired with one oil inlet. One aqueous/oil inlet pair is approximately 100 µm in width or diameter, and the other is approximately 50 µm in width or diameter. Mixtures of cells in ~40 µm emulsion microdroplets are injected into the 50 µm channel using a pressure pump set at approximately 100 mbar. A mixture of oligo-dT magnetic beads and Tween-20 surfactant in an aqueous binding buffer, in ~80 µm droplets, is injected into the 100 µm channel using a pressure pump set at approximately 100 mbar. The droplets streams merge into a single channel such that they co-flow at periodicities controlled by the pressure or flow rate of the inlet lines. The two oil inlet lines are used to achieve droplet periodicity such that each cell mixture droplet is paired with a single lysis and bead mix droplet. Using a power supply (Mastech) and an inverter (TDK), a 7 V AC electrical current is applied to a 160 µm stretch of widened droplet co-flow channel. The current is applied by injecting a 1 M NaCl solution into a channel unconnected to the droplet co-flow channel, but close enough that the AC current is conducted into 160 µm stretch of widened co-flow channel. The ~80 µm lysis/bead mix droplet slows down slightly and deforms in the widened channel. The ~40 µm cell mixture droplets do not slow down in the widened channel, ensuring that each cell droplet is in contact with a lysis/bead droplet. Simultaneous application of electric current results in fused, diluted droplets, which are then incubated off-chip to bind poly(A) RNA to the oligo-dT beads. A typical experiment in the setting achieves >98% droplet fusion at a throughput of ~500 droplets per second, with 100% cell lysis.

The interaction between a TCR and its cognate peptide:MHC target can induce transcriptional responses in both the TCR-expressing cell (e.g., primary T cell or TCR-engineered Jurkat cell) and the peptide:MHC-expressing cell (e.g., primary APCs or engineered APCs). Depending on which functional cellular interaction is of interest, primer sets can be designed to link peptide:MHC sequence with T cell transcriptional response, or TCR sequence with APC transcriptional response. In some embodiments, it is desirable to investigate the interaction comprehensively, e.g., link peptide:MHC, TCR, T cell response, and APC response. To link peptide:MHC sequence with T cell transcriptional response, APCs can be incubated with TCR-expressing cells in emulsion microdroplets in a combinatorial screen, using the partitioning methods described above. The recombinant APCs can be engineered to express a library of peptide:MHC targets, with a specific barcode indicating each peptide:MHC target in the library. After incubation for 6, 12, 18, 24, 36 hours, or more in emulsion microdroplets, the cell mixture emulsion microdroplets can be fused with lysis/bead emulsion microdroplets using the methods described above. The RNA-bound beads can be then injected into emulsion microdroplets for multiplex OE-RT-PCR. Primers can be introduced into the emulsion microdroplets that amplify at least one T cell activation marker, for example, Interferon Gamma (IFNg), CD69, or Interleukin-2 (IL-2). The primers can be designed to span across introns, such that no amplification from background genomic DNA takes place, and the amplicons are 100 bp-300 bp in size. In some embodiments, one primer of each T cell activation primer pair has a polynucleic acid subsequence with complementarity to one primer of the barcode amplification primer pair. The complementary subsequences hybridize during OE-RT-PCR, so that a plurality of linked amplicons is generated. In this way, peptide:MHC target sequences are linked to functional responses in T cells. In an exemplary embodiment, a target library comprises clones engineered with a polynucleotide of NY-ESO-1 target sequence (SEQ ID NO: 13) and a polynucleotide of MART-1 target sequence (SEQ ID NO: 16), and a primer set that comprises target barcode primers (e.g., SEQ ID NO 14-15), primers for IFNG (SEQ ID NO: 25-26), and primers for IL-2 (SEQ ID NO: 27-28). Sequencing adapters (e.g., Illumina sequencing adapters) can be added to the library of linked amplicons using nested, tailed-end PCR, as described above. The peptide:MHC and T cell activation marker pairings can be identified and quantified by deep sequencing the linked amplicons, for example, obtaining 100,000, one million, or ten million sequences from the library of linked peptide:MHC and T cell activation marker complexes. Bioinformatics can be then used to match the sequenced barcodes with peptide:MHC by searching a database of peptide:MHC barcodes, which was generated using any of the methods above. In some embodiments, it is beneficial to in parallel generate hybridized amplicons that link TCR sequences to peptide:MHC sequences, and TCR sequences with T cell activation markers. For such embodiments, the OE-RT-PCR amplification mixtures can also include primers that link TCRβ polynucleic acids with peptide:MHC barcodes and/or T cell activation markers. The TCR primer set can amplify from the most 5' end of the TCRβ V region across to a universal primer that sits in the Cβ region. The Cβ primer can have a polynucleic acid subsequence with complementarity to one primer from the barcode amplification primer pair, and to one primer from each of the T cell activation marker primer pairs. The TCRβ amplicons can be ~400-500 bp in size. The primer set that includes primers for peptide:MHC barcodes, T cell activation markers, and TCRβ can generate the following amplicons: peptide:MHC linked to T cell activation markers, TCRβ linked to peptide:MHC, and/or TCRβ linked to T cell activation markers. Sequencing adapters (e.g., Illumina adapters) can be added to these amplicons using nested, tailed-end PCR, as described above. The library (e.g., Illumina library) can be then deep sequenced to obtain 100,000, one million, or ten million sequences. Bioinformatics can be then used to process the raw sequences, and then match peptide:MHC to TCRβ, TCRβ to T cell activation markers, and/or peptide:MHC to T cell activation markers. In this way, the combinatorial screen yields a list of cognate pairs of peptide:MHC and TCRs that bind and activate cellular phenotypes of interest. An even more comprehensive mixture can also generate TCRαβ linkage amplicons, such that the interactions between APCs and T cells can be used to identify linked TCRαβ of interest, which are then expressed as full length recombinant TCRαβ, and further analyzed for in vitro and in vivo function.

Other primer mixes can be used if other T cell functional responses are of interest. For example, so-called immune "checkpoint" genes act as co-stimulatory or co-inhibitory regulators of T cell activity. Checkpoint molecules are typically expressed on the surface of T cells or T cell target cells, and interact with other co-stimulatory or co-inhibitory molecules on the surface of the same cell or another cell. Checkpoint molecules and the utility of "checkpoint inhibition" in cancer therapy are known in the art (e.g., Shin *Current Opinion in Immunology* 2015, 33:23-35). These networks of co-stimulatory or co-inhibitory molecules are activated or antagonized by a variety of molecules, including monoclonal antibodies, and such modulatory molecules effect changes in T cell phenotype. Combinatorial screens can be performed on various combinations of activating or antagonizing molecules, or molecules with unknown function, to induce transcriptional changes in target T cells. This can be achieved, for example, by partitioning a library of antibody-secreting CHO cells (inducer cells) with checkpoint-expressing cells (target cells, e.g., T cells). In some embodiments, the checkpoint-expressing cells are non-engineered primary T cells, or primary T cells transduced to express a checkpoint receptor protein. The antibody-secreting CHO cells can comprise a library of antibodies with known activities against checkpoint molecules, or a library of antibodies with unknown function, for example, a library generated from antibody-expressing cells isolated from a mouse immunized with a checkpoint protein. In any scenario, antibody-expressing cells can be isolated into emulsion microdroplet partitions with checkpoint-expressing target cells. Ratios of antibody-expressing cells to target cells in this setting can be 1:1, 1:2, or 1:5, or any ratio in between if the functions of the antibodies are unknown. Optimal ratios of antibody-expressing cells to target cells in this setting are 1:1, 2:1, or 5:1 if the goal is to identify combinations of antibodies that induce expression of checkpoint molecules. After incubation for 6, 12, 18, 24, 36, or more hours in emulsion microdroplets, the cell mixture emulsion microdroplets can be fused with lysis/bead emulsion microdroplets using the methods described above. The RNA-bound beads can be then injected into emulsion microdroplets for multiplex OE-RT-PCR. In this application, primers for OE-RT-PCR can comprise antibody-specific primers and checkpoint-molecule specific primers. The antibody primer pool can include a universal primer for the heavy chain constant (C) region. This abrogates the need for a large pool of J region primers. The primer pool can also include primers that bind to all possible V segments for IgG. The primers can amplify across the full variable region of each Ig monomer, i.e., FR1, CDR1, FR2, CDR2, FR3, CDR3, and FR4 for heavy and light chain Igs. Antibody heavy chain amplicons can be 400-450 bp. At least one checkpoint transcript primer pair can be included, for example, a primer pair for LAG-3, PD-1, TIM-3, CEACAM-1, CD200R, CTLA-4, TIGIT, or BTLA. General proliferation or activation markers can also be included, such as IFNg or IL-2. Some primer pools include primers for all of these transcripts, or subsets of the list. The primer pool can also comprise the full transcriptome of the T cells. The primers can be designed to span across introns, such that background genomic DNA does not contaminate the amplification signal. Amplicons for these transcripts can be between 100-300 bp, 200-500 bp, 300-600 bp or less than 1000 bp. The antibody C region primer can comprise a subsequence with reverse complementarity with a subsequence of one member of the primer pair for each of the checkpoint transcripts. The complementary polynucleic acid subsequences enable OE-RT-PCR to generate major amplicons that link an antibody sequence from a CHO cell with checkpoint sequences from a target cell. Sequencing adapters (e.g., Illumina sequencing adapters) can be added to the library of linked amplicons using nested, tailed-end PCR, as described above. The antibody and T cell checkpoint marker pairings can be identified and quantified by deep sequencing the linked amplicons, for example, obtaining 100,000, one million, or ten million sequences from the library of linked complexes. Bioinformatics can be then used to quantify the checkpoint transcripts linked to each antibody of interest. In some embodiments, it is beneficial to also identify clonality of the reactive T cell clone. For example, if multiple antibody-expressing CHO cells are isolated into emulsion microdroplets with target cells, functional combinations of antibodies can be of interest. In this situation, T cell clones can be identified by including TCRβ primers in the OE-RT-PCR mix. In some embodiments, the T cells can be engineered to express transcripts with barcodes, such that the barcodes are used to identify the T cell clones that are reactive to antibody combinations. In any experimental design, the bulk sequencing data can have utility for identification of functional relationships among co-stimulatory and co-inhibitory checkpoint molecules. For example, activation of OX40 can result in down-regulation of PD-1 or CTLA4, inhibition of PD-1 can result in activation of OX40, and so on. In another example, a mixture of two antibodies activates T cells more effectively than any other mixtures, as evidenced by a large plurality of bulk sequencing data that link the antibody sequences with IFNg and IL-2 proliferation and activation markers. In some embodiments of the invention, transcripts of interest are either up-regulated or down-regulated.

In some embodiments, a primer set that links NK cell activity (intermediary cells) with antibody-expressing cells (inducer cells) can be used. For example, a population of CHO cells is engineered to express a library of secreted antibodies. Another population of CHO cells is engineered to express antigens of interest. Alternatively, tumor cells are used as antigen-expressing cells. In a typical combinatorial screen, a plurality of single cells from a library of tens, hundreds, thousands, hundreds of thousands, or millions of antibody-expressing CHO clones are partitioned with antigen-expressing cells. If the antigen-expressing cells comprise a diverse population of clones, the ratio of antibody-expressing cells to antigen expressing cells can be 1:2, 1:1, 2:1, or any ratio in between. If the antigen-expressing cells comprise cancer cells, the ratio of antibody-expressing cells to cancer cells can be 1:1, 1:5, 1:10, 1:100, or any ratio in between. The mixtures of antibody-expressing cells and antigen-expressing cells can be partitioned into emulsion microdroplets with NK cells. We refer to the NK cells as intermediary cells because the antibody-expressing cells induce changes in NK cell expression via binding of secreted antibody to the target cells, instead of through direct cell-to-cell interactions between the antibody-expressing cells and the target cells. After incubation for 6, 12, 18, 24, 36, or more hours in emulsion microdroplets, the cell mixture emulsion microdroplets can be fused with lysis/bead emulsion microdroplets using the methods described above. The RNA-bound beads can be then injected into emulsion microdroplets for multiplex OE-RT-PCR. In this application, primers for OE-RT-PCR can comprise antibody-specific primers and NK activation primers. Antibody-specific OE-RT-PCR primers are described above. NK transcripts that are up-regulated upon activation can include effectors (IFNg; TNFa), proteases (Granzyme A [Gzma]; Granzyme B [Gzmb]), transcription factors (T Box Transcription Factor 21 [Tbx21/T-bet]; Eomesodermin [Eomes]; PU Box Transcription Factor [PU.1]; Inhibitor of DNA Binding 2 [Id2]), and signaling adaptor proteins (DAP12; Spleen Associated Tyrosine Kinase [Syk]; Zeta-Chain-Associated Protein Kinase 70 [Zap70]). Transcripts of interest can also comprise targets that are down-regulated on NK cell activation. The NK cell activation primer set can comprise at least one NK cell activation transcript target, for example, they can comprise two, five, ten, 100, or 1,000 targets, or the full transcriptome of NK cells. The primers can be designed to span across introns, such that background genomic DNA does not contaminate the amplification signal. Amplicons for the NK activation transcripts can be 100-300 bp, 200-500 bp or less than 1000 bp. The antibody C region primer can comprise a subsequence with reverse complementarity with a subsequence of one member of the primer pair for each of the NK cell activation transcripts. The complementary polynucleic acid subsequences enable OE-RT-PCR to generate major amplicons that link an antibody sequence from a CHO cell with NK cell activation sequences. In some embodiments, an example primer set comprises primers for IGG V gene (e.g., SEQ ID NO:1, SEQ ID NO:2, SEQ ID NO:3, and SEQ ID NO:4), primers for GZMB (e.g., SEQ ID NO:9 and SEQ ID NO:10), and primers for TBX21 (e.g., SEQ ID NO:11 and SEQ ID NO:12). Sequencing adapters (e.g., Illumina sequencing adapters) can be added to the library of linked amplicons using nested, tailed-end PCR, as described above. The antibody and NK cell activation marker pairings can be identified and quantified by deep sequencing the linked amplicons, for example, by obtaining 100,000, one million, or ten million sequences from the library of linked complexes. Bioinformatics can be then used to quantify the NK activation transcripts linked to each antibody of interest. In this way, antibodies that induce NK cells can be identified through a functional assay that involves three cell types: NK cells (intermediary cells), antigen-expressing cells (target cells), and antibody-expressing cells (inducer cells).

In some embodiments, the transcripts induced in the target cells are uncharacterized, or the transcriptional signature of the target response is complex, requiring quantification of hundreds or thousands of transcripts. In those cases, methods that quantify the full transcriptome of gene targets can be used. For example, unique polynucleic barcodes are affixed to solid supports, such as beads, using the methods described above, and are delivered to emulsion microdroplets with cell mixtures. Barcoded polynucleic acids from the beads, also comprising oligo-dT subsequences, can be used to barcode the full transcriptome of a target cell. This can be achieved through OE-RT-PCR or through first strand labeling. Then, OE-RT-PCR or OE-PCR can be used to generate major amplicons comprising polynucleic acid sequences indicative of the inducer clone. For example, peptide:MHC can be linked to the full transcriptome of a TCR-expressing cell, or an antibody sequence from an antibody-expressing cell can be linked the full transcriptome of a T cell. Such methods are also possible where the inducer clone does not directly interact with the target cells, for example, NK cells activated through antibodies binding to tumor cells, as described above. Nested, tailed-end PCR can be used to attach sequencing adapters (e.g., Illumina sequencing adapters) to a plurality of the major amplicons. Then, bulk sequencing can be performed to obtain hundreds of thousands, millions, hundreds of millions, or billions of sequences. Bioinformatic algorithms can be used to identify transcripts in target cells or intermediary cells that are up- or down-regulated in response to inducer cells. Such methods can be used to discover novel biomarkers for functional cellular interactions.

The methods described above are provided as examples, and any variants thereof can be adopted to achieve similar utility. For example, nucleic acid amplification can be effected through padlock probes or ligase chain reaction.

Though most of the protocols described above use RNA sequences for clonal identification, it is also possible to use genomic DNA sequences for clonal identification. For example, a library of inducer clones can be made by directed CRISPR/Cas9 genome editing, or random insertion of a polynucleic acid of interest into a library of inducer clones. In such situations, the genomic DNA sequence of interest can be amplified and linked to transcripts in the target cells. In some applications, changes other than transcriptional changes can be induced in the target cells. For example, inducer cells can induce epigenetic changes in the target cell's genome. In some applications, inducer cells can change protein profiles of target cells. Such changes can be quantified by binding nucleic-acid barcoded antibodies to the target cells, such that the barcoded antibodies can be amplified and linked to polynucleic acid sequences for clonal identification in the inducer cells.

In some embodiments of the invention, a polynucleic acid barcode is delivered to a droplet or vessel that contains a mixture comprising target and inducer cells. This polynucleic acid barcode can be affixed to a solid support, such as a bead, antibody, or cell. The cells can be lysed and RNA from the mixture of cells is fused with polynucleic acid barcode. Transcript cDNAs from target and inducer cells can be then sequenced and traced back to the droplet or vessel using the polynucleic acid barcodes. Thus, in some embodiments, transcript cDNAs from target and inducer cells are never directly fused, but rather the combinations are linked bioinformatically through the polynucleic acid barcodes.

In some embodiments of the invention, cells, cell mixtures, or emulsion microdroplets are labeled with RFIDs, electronically indexed solid supports, light-triggered microtransponders (e.g., Mandecki U.S. 20160175801), quantum dots, colorimetric indexes, fluorescent markers, or other identifying "barcodes" that are not based on polynucleic acids. These identifiers can be used to identify clones, memorialize laboratory protocols used to process mixtures of cells, or indicate the result of a biological assay. Such identifying barcodes can be affixed to or comprise solid supports, such as microchips or beads of less than 50 microns at the widest dimension, affixed to proteins, or engineered into cells as expression constructs responsive to a stimulus. In some embodiments, one population of TCR-expressing clones, for example, CD4+ T cells, is labeled with the same RFID barcode. A second population of TCR-expressing clones, for example, CD8+ T cells, is labeled with a second RFID barcode. Then, these two populations of cells are mixed. In some embodiments of the invention, the population of the RFID-tagged TCR-expressing clones are encapsulated into emulsion microdroplets with a library of peptide:MHC-expressing cells, as described above. The RFID tags can be then used to sort microdroplets into CD4+ and CD8+ emulsions. In this way, the RFID barcode enables further de-multiplexing beyond a nucleic acid barcode or TCR clone. Two, ten, 100, 1,000, 100,000, or millions of different RFID particles can be used. In some embodiments, the identifying index is a fluorescent marker, and cell-containing droplets are sorted with flow cytometry, or FACS. In some embodiments, a biological assay taking place inside emulsion microdroplets results in production of a fluorescent marker, and then cell-containing droplets are sorted with flow cytometry. In some embodiments, a single fluorescent wavelength is used, and cell-containing droplets are sorted as positive or negative based on a fluorescence threshold that indicates a positive readout in the biological assay. Polynucleic acid barcodes can also be affixed to particles with RFIDs, for example, to link RFID with deep sequencing data. The particles with RFIDs can also be soaked in drugs, or coated with antibodies or proteins, which can then be used in functional assays and de-multiplexed with an RFID reader. In some embodiments, the RFID, electronically indexed solid supports, quantum dots, colorimetric indexes, fluorescent markers, or other identifying "barcodes" that are not based on polynucleic acids are used to trace an incubation protocol. For example, there is an interest in incubating TCR-expressing cells with peptide:MHC-expressing cells for 2 hr, 6 hr, 10 hr or more. RFID-tagged solid supports are delivered to the emulsion microdroplets with the cell mixtures. Then, emulsion microdroplets are sorted into three different incubation receptacles. The receptacles are incubated for 2 hr, 6 hr, or 10 hr. During sorting, the RFIDs are read by an RFID reader, and a computer is used to record the RFIDs that are associated with each protocol. The method enables combinatorial screens with multiple protocols run concurrently. Different protocols can comprise different media, incubation temperatures, interacting cells, drugs, proteins, or molecules, temperatures, or incubation times.

In some embodiments of the invention, cells are used to both induce responses in other cells and to compartmentalize polynucleic acids unique to clones, for example, a polynucleic acid barcode or a variable immune receptor. In some embodiments, cell responses are induced by a molecular reagent affixed to a solid support, for example, a bead or a microfluidic chamber. In some embodiments, the molecular reagent and the solid support act as an inducer, rather than a cell. In some embodiments, the molecular reagent is expressed by filamentous phage, or other kind of virus or virus-like particle, rather than a cell or solid support. In some embodiments, the particle acts as an inducer, rather than a cell. In certain embodiments, said molecular reagent is a protein such as a cytokine, or an organic drug substance.

In some embodiments, microbial cells, such as recombinantly engineered yeast are used as inducer cells. For example, yeast display methods can be used for rapid and cheap expression of TCRs and antibody fragments (scFv). In some embodiments, tailed-end PCR is used to add polynucleic acid "adapters" to the heavy and light chain linkage amplicons, for homologous recombination in vivo. The modified DNA libraries can be then electroporated into Saccharomyces cerevisiae cells with a linearized vector (pYD) that contains a GAL1/10 promoter and an Aga2 cell wall tether. The GAL1/10 promoter induces expression of the scFv protein in medium that contains galactose. The Aga2 cell wall tether can be used to shuttle the scFv to the yeast cell surface and tether the scFv to the extracellular space. Transformed cells can be then expanded and induced with galactose. The scFv-expressing yeast library is then used as a library of inducer clones.

3) High-Throughput Functional Analysis

Libraries of clonal cells, prepared by any of the methods above, can be characterized and quantified through bulk sequencing. Prior to performing any kind of functional assays, it can be useful to characterize and quantify the contents of a population of clones. For example, methods that generate populations of clones can comprise several technical steps, which can yield inadequate results from time to time, and thus deep sequencing can be performed as quality control. RNA can be isolated from a population of clonal cells, and then subjected to RT-PCR to make libraries of DNA for bulk sequencing. If the library comprises antibodies or TCRs, RT-PCR can be performed using a pool of V-gene primers on the 5' end of the transcripts, and C-gene primers on the 3' end of the transcripts. In addition to the transcript-specific sequences, the RT-PCR primers can have subsequences that comprise polynucleic acid sequences that enable bulk sequencing (e.g., Illumina sequencing). These polynucleic acid sequences, termed sequencing adapters (e.g., Illumina sequencing adapters), enable hybridization of the library to bulk sequencing flow cells, such that bridge amplification and sequencing by synthesis takes place. Similar methods can be used for barcoded cDNA libraries, or any other RNAs that enable trace back to single cell clones. Sequencing methods offered by commercial providers such as Pacific Biosciences, Oxford Nanopore, and Roche have similar utility as methods offered by Illumina.

In bulk sequencing, read errors can be difficult to distinguish from biological variation, which complicates identification of clones. To reduce the frequency of base call errors, the expected error filtering method know in the art, e.g., methods of Edgar and Flyvbj erg (Bioinformatics 2015 Nov. 1; 31(21):3476-82), can be used. For example, the expected number of errors (E) for a read can be calculated from its Phred scores. Reads with E>1 can be discarded, leaving reads for which the most probable number of base call errors is zero. When greater sensitivity to rare variants is needed, larger values of E may be used. As an additional quality filter, singleton reads (i.e., reads with a sequence found only once) can be discarded, noting that sequencing errors are unlikely to be reproduced by chance so that sequences found two or more times have a high probability of being correct.

Methods described above can be used interchangeably for biological assays that measure activation or inactivation, and for biological assays that measure up-regulation or down-regulation of transcripts. The biological assays can be used to measure both up-regulation and down-regulation of transcripts concurrently.

EXAMPLES

Example 1: Functional Analysis of Fc Variants or Mutants

Therapeutic antibody drugs function by a variety of mechanisms. Two common mechanisms for therapeutic antibody drug function are Antibody-Dependent Cell-mediated Cytotoxicity (ADCC) and Complement Dependent Cytotoxicity (CDC). Both ADCC and CDC are mediated by the Fragment Crystallizable (Fc) region of antibodies. In ADCC, the variable domain of an antibody binds to an antigen exposed on the surface of a cell. If enough antibody molecules bind to the antigen, NK cells bind to the Fc domains via CD16, also known as Fc Receptor (FcR). In the classical pathway for CDC, antibodies bind an antigen on a target cell's surface. Then, the C1 complex of the complement cascade binds to the Fc domain of the antibody. Typically, at least six antibody molecules are required for C1 to bind. Binding of C1 to Fc then recruits remaining components of the classical complement pathway, which form a membrane attack complex that works to rupture the target cell's cell membrane. The four major IgG isotypes (IgG1, IgG2, IgG3, and IgG4) differ in their capacity for mediating ADCC and CDC. IgG3, IgG1, and IgG2 have the highest to lowest ability to activate complement, respectively. IgG4 does not activate complement. IgG1, IgG3, IgG4, and IgG2 have the highest to lowest ability to bind FcR, respectively. Drug developers therefore have interest in finding the optimal Fc for antibody candidates. In certain situations, drug developers fuse high-affinity variable domains to the optimal wild type Fc sequences. In other situations, drug developers mutate wild type Fc sequences to generate libraries of Fc variants, or Fc mutants. Conventionally, drug developers choose optimal Fc variants by high-throughput screens for binders to FcR or C1, followed by functional analysis in 96-well plates. There is a need in the field for high-throughput methods that screen directly for functional Fc variants, which removes the requirement for 96-well plate functional analysis.

To screen functional Fc variants, a library of Fc mutants is generated by methods known in the art (e.g., synthetic generation of polynucleic acids that are then assembled into protein-coding polynucleic acids, site-directed mutagenesis, or error-prone PCR). The library of Fc mutants is expressed recombinantly in Chinese hamster ovary (CHO) cells. The Fc mutants are fused to a membrane tether protein domain. In this way, The Fc mutants are able to bind directly to FcR or C1, and induce cellular functions, while still bound to the cell membrane. The resulting Fc mutant library comprises a population of clones, a plurality of which express a single Fc variant.

A plurality of clones from the library of variant Fc-expressing CHO cells are isolated with NK cells between The ratio between Fc-expressing CHO cells and NK cells ranges between 1:10, and 1:20. NK-92 cells or primary NK cells are used for the experiment. Other kinds of mammalian cell lines, for example CHO, HEK293, or Jurkat, engineered to express CD16 receptors, are also tested, substituting NK cells.

The Fc-expressing CHO cells and NK cells are partitioned into aqueous-in-oil droplets, and then incubated for 2, 4, 6, 12, 18, or 24 hours in a 37° C. tissue culture incubator, such that functional Fc variants expressed by the CHO clones bind to CD16 molecules of the NK cells, which activates the NK cells. These droplets are 20-200 μm in diameter. The droplets are then injected into a second microfluidic chip that fuses the cell-containing droplets with droplets that contain lysis mix and oligo-dT microbeads. The lysis mix contains a surfactant such as SDS, and poly(A) RNA transcripts bind to the oligo-dT microbeads. Overlap extension droplet PCR using primers specific to immunoglobulin and NK cell activation markers, for example, TNFa or IFNg, such that the polynucleotides encoding the activation markers are linked through hybridization to polynucleotides encoding Fc variants. Universal primers are also added to amplify any Fc variant in the library of engineered CHO. The droplet overlap extension RT-PCR is performed by injecting beads into aqueous-in-oil reactors, and incubating in a tube in a conventional thermal cycler. The plurality of polynucleic acids generated by overlap extension RT-PCR are then subjected to bulk sequencing to identify and quantify Fc sequences linked to NK cell activation markers.

NK cell activation markers that can be used for these experiments are endogenous transcripts expressed by the NK cells or transcriptional reporters engineered into NK cells. From this experiment, Fc variants expressed by CHO cells that induce a functional response in NK cells are identified. Similar experiments are performed with neutrophils or other cells that phagocytose cells coated in complement, incubated with the Fc variant library. The medium encapsulated with the cells includes C1 and other components of complement. Neutrophil activation transcripts are linked by droplet overlap extension RT-PCR to Fc variant sequences. The resulting library of linked polynucleic acid molecules can be then subjected to bulk sequencing to identify and quantify Fc sequences linked to neutrophil activation markers.

Similar experiments are also performed with recombinant cells engineered to express CD16 or other receptors, incubated with the Fc variant library.

Variant Fc receptors that show optimal ADCC or CDC function are then fused to an antibody variable domain with affinity toward a therapeutic target of interest. The methods for cloning and purifying monoclonal antibodies are well known to those skilled in the art. These monoclonal antibodies are then further validated for ADCC or CDC by conventional well plate assays. The pharmacokinetic properties of the Fc variant are investigated. In many therapeutic modalities, increased antibody half-life is desired and is increased by mutations in the Fc domain. The Fc-variant fused antibodies are subjected to efficacy analysis using mouse models for cancer, efficacy analysis using opsonization studies or other types of efficacy analysis. This experiment provides highly efficient Fc-variant fused antibodies.

Example 2: Functional Analysis of Memory B cells

Many patients recover from severe disease for reasons currently unknown to science. For example, certain cancer patients respond better than other patients to medical treatments. In another example, certain patients respond better viral pathogens (e.g., Ebola, Zika, or influenza A) than other patients. Other examples include bacterial pathogens and autoimmune disorders. In some cases, patients successfully recover from severe disease because they successfully mount an immune response against the disease, e.g., T cell receptors or immunoglobulins that are present and active in good responding patients but not present in poor responding patients might function by binding to relevant disease targets.

Memory B cells, or Bmems, are particularly useful for the discovery of antibodies that helped an individual recover from serious disease. On initial stimulation by an antigen, naïve follicular B cells differentiate into plasma cells and Bmems. Plasma cells mount the primary humoral immune response to the antigen. Persistent Bmems arise after affinity maturation (mutation and selection with the antigen) in germinal centers. A patient may have millions to billions of different Bmem clones from among which a drug developer may wish to discover an antibody that contributed to recovery from severe disease. Conventionally, screening for reactive Bmems involves incubating a population of Bmems with a fluorescently labeled target of interest, and then flow sorting for binders. Methods for flow sorting are familiar to those skilled in the art, and typically is performed using devices commercially manufactured by suppliers such as BD, Sony, or Beckman Coulter. However, such methods do not take Bmem cellular function into account. Additionally, flow sorting is easiest with a soluble target, whereas many targets are best studied as recombinant proteins embedded in cell membranes. Therefore, there is a need in the field for high-throughput cellular methods that could distinguish reactive from non-reactive Bmems, upon exposure to an antigen of interest.

To identify reactive Bmems, Bmems are extracted from the peripheral blood of a patient that has recovered from Ebola infection by flow cytometry or antibody-coated magnetic beads. The Bmems are then incubated ex vivo with the antigen of interest (e.g., recombinant inducer cells that express a library of domains of the glycoprotein (GP) that comprises surface projections of the lipid envelope of the Ebola virus). The incubation takes place inside aqueous-in-oil microdroplets or in nanoliter wells in a microfluidic device. The B cells are subjected to emulsion overlap extension RT-PCR to generate a library of polynucleic acids that link heavy immunoglobulin sequences to transcripts indicative of Bmem cell activation. The activation transcript can be endogenous transcripts of Bmem cells such as Ki-67 or transcripts of a reporter engineered into the Bmem. From this experiment, antibodies expressed by Bmem cells that respond to the antigen are identified by the activation biomarkers, and that these biomarker transcripts are additionally hybridized to transcripts that discriminate the presence of a GP domain on a cell co-encapsulated with the target Bmem.

Antibody sequences linked to Bmem activation markers are then cloned and purified as monoclonal antibody protein. The methods are performed either on a single antibody sequence, or on a library of antibody sequences. If performed on a library of sequences are cloned and purified, recombinant proteins expressed from the library are then further screened for binding or function in vitro. The methods for cloning, purifying, and screening recombinant antibodies are well known to those skilled in the art. Isolated monoclonal antibodies are then validated for binding and function through conventional well-plate assays or mouse models. This experiments allow identification of antibodies that helped an individual recover from Ebola infection.

Bmem response to antigens is also compared across many individuals, as a method for identifying appropriate polypeptide sequences for development of broadly efficacious vaccines. For example, the immunogenic domains of Ebola GP are discovered, associated with good outcomes in patients who have recovered from infection, and then those domains form the basis of a vaccine that generates a protective antibody response and Bmem population for individuals who receive the vaccine but have never been exposed to Ebola virus.

Similar methods are further used to find antigenic peptides for T cells.

Example 3: Functional Analysis for Discovery of Antibody Targets

Many patients recover from severe disease for reasons currently unknown to science. For example, certain cancer patients respond better than other patients to medical treatments. In another example, certain patients respond better viral pathogens (e.g., Ebola, Zika, or influenza A) than other patients. Other examples include bacterial pathogens and autoimmune disorders. In some cases, patients successfully recover from severe disease because they successfully mount an immune response against the disease, e.g., immunoglobulins that are present and active in good responding patients but not present in poor responding patients might function by binding to relevant disease targets.

However, because of the complexity of many diseases and the complexity of immune systems, it remains difficult to discover the immunoglobulins and their respective targets. This knowledge would be extremely useful to researchers studying the mechanism of disease, the mechanism of disease response, and methods for treating disease. For example, an antibody produced by a cancer patient binds to a tumor through specificity to a glycoprotein target expressed by the tumor and unknown to science. Binding of this antibody to the tumor then induces ADCC and CDC, which leads to complete remission of the cancer. However, it is difficult to find the sequence of the functional antibody as well as the target of the functional antibody. Drug developers may use the antibody as a drug, or develop closely related sequences once the endogenous sequence is known. Drug developers may also use the newly discovered target to immunize mice or screen phage display libraries, and develop novel antibodies with affinity toward the newly discovered target. Conventionally, it is difficult and expensive to obtain the complete complement of glycoprotein targets present in a tumor. Therefore, the field would benefit from a high-throughput method that identifies the antibody and its target, using the glycoprotein targets expressed by the tumor and the immune repertoire sequences expressed by the patient. The method is not limited to cancer, and can be applied to any disease that involves the immune system.

To identify an antibody and its target using the glycoprotein targets expressed by the tumor and the immune repertoire sequences expressed by the patient, B cells are isolated from a cancer patient, for example, peripheral blood, bone marrow, or tumor infiltrating lymphocytes. The cancer patient recently recovered from the cancer, is currently fighting the cancer, or is fighting the cancer and receiving immune modulating therapies. Methods for separating B cells from non-B cells include flow cytometry and antibody-coated magnetic beads. B cells incubated with an antigen, pool of antigens, cells, or tissues of interest (e.g., a tumor or tumor cells) are used for the purpose of activating or expanding B cells of interest to the study. The B cells are subjected to emulsion overlap extension RT-PCR to generate a library of polynucleic acids with natively linked heavy and light chain immunoglobulin pairings. These libraries of immunoglobulins are then used to engineer recombinant antibody-secreting cells, for example, Chinese hamster ovary cells. Methods for engineering cells are familiar to those skilled in the art, and may include electroporation of plasmids, lentiviral transduction, lipid-based transfection or transient transfection of a plasmid. Primary B cells are used to generate antibody-secreting hybridomas.

A library of cell clones secreting antibodies is screened against a library of cell clones expressing putative antibody targets. The antibody targets are encoded by complementary DNA cloned into an expression plasmid. The cDNAs are derived from RNA isolated from a tumor, for example, a tumor that was surgically removed from the patient that provided the sample of B cells, or from a different patient or patients. The tumor is the same tissue of origin as the tumor from the patient that provided the sample of B cells, or from a different tissue of origin as the tumor from the patient that provided the sample of B cells. cDNA derived from tissues unrelated to tumors, or human donors without cancer is used. For some experiments, the library of putative antibody targets generated by engineering recombinant cells with synthetic DNA cloned into an expression plasmid is used.

A plurality of clones from the library of antibody-secreting CHO cells are then isolated with cells that express cDNA from a matched tumor ("target clones"). A plurality of NK cells (intermediary cells) are also isolated with the antibody-expressing clones and the cDNA-expressing clones. A typical ratio of antibody-expressing cells to cDNA-expressing cells to NK cells is 1:1:10, or 1:1:20. NK cells comprise NK-92 cells or primary NK cells. The cells are partitioned into aqueous-in-oil droplets, and then incubated for 2, 4, 6, 12, 18, or 24 hours in a 37° C. tissue culture incubator, such that antibodies secreted from CHO clones bind to the cDNA-expressing cells, which activates the NK cells. These droplets are 20-200 μm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to immunoglobulin and NK cell activation markers, (e.g., endogenous transcripts of NK cells such as TNFa or IFNg, or transcripts of reporters engineered into NK cells), such that the polynucleotides encoding the activation markers are linked through hybridization to polynucleotides encoding immunoglobulin. Immunoglobulin is also linked through hybridization to specific identifying sequences in the putative target cDNA transcript. For example, the cDNA transcripts of the putative targets may contain synthetic polynucleic acid barcodes or unique non-synthetic sequences. Droplet overlap extension RT-PCR is performed by injecting the beads into aqueous-in-oil reactors, and incubating in a tube in a conventional thermal cycler. The plurality of polynucleic acids generated by overlap extension RT-PCR are then subjected to bulk sequencing to identify and quantify antibody sequences linked to NK cell activation markers, and then link these antibody sequences to putative cDNA target transcripts. Heavy chain immunoglobulin is linked to activations markers and light chain immunoglobulin, to form fusion complexes of three, four, or more transcripts such that polynucleic acid sequences sufficient to produce antibody protein are generated. Heavy chain immunoglobulin is linked to activations markers and light chain immunoglobulin, such that only two transcripts are linked, for example, heavy chain immunoglobulin and TNFα. From this experiment, antibodies secreted by antibody-secreting CHO cells that induce a functional response in NK cells are identified, and these antibodies are linked in parallel to putative target cDNA transcripts. In this way, an antibody is paired with its target through high-throughput functional analysis.

Similar experiments are performed with libraries of antibodies that are not derived from human repertoires. For example, antibody sequences randomly or synthetically generated are used. Cells that express such libraries comprise recombinant Chinese hamster ovary cells engineered with synthetically generated antibodies. The library of antibodies is then screened against a library of recombinant cells expressing tumor cDNAs. A single monoclonal antibody is screened against a library of recombinant cells expressing tumor cDNAs.

Similar experiments are performed with recombinant CD16-engineered cells instead of NK cells. Recombinant CD16-engineered cells also express a reporter transcript, which is used as an activation biomarker. Similarly, any cell reactive to antibodies binding to a cell surface is used instead of NK cells.

Antibody sequences linked to NK cell activation markers are then cloned and purified as monoclonal antibody protein. A cDNA target linked to NK cell activation and at least one antibody sequence from an immune repertoire is then used to discover novel antibodies against the cDNA target, for example, through mouse immunization, phage display, or yeast display. The methods for cloning and purifying monoclonal antibodies are well known to those skilled in the art. In parallel, the associated target cDNA is cloned and used to validate the monoclonal antibody by conventional well plate assays or mouse models for cancer.

Example 4: Functional Screen of Therapeutic Antibody Candidates

Therapeutic antibody drugs function by a variety of mechanisms, but those skilled in the art of antibody drug development would appreciate that the ability of an antibody to bind to a given target does not necessarily guarantee that the antibody induces the required biological function. For example, proteins expressed on the surface of immune cells that modulate cancer (e.g., PD-1, OX-40, or LAG3) may be immune activators or immune repressors. A drug developer looks for drugs that agonize or antagonize immune activators or immune repressors. For example, the putative therapeutic mechanism of an anti-OX40 antibody is to act as an agonist. OX40 is expressed on the surface of T cells, and binding of OX40L activates T cells. Activated T cells then can mount an immune response against the tumor, which improves the condition of the patient. In certain therapeutic modalities, activating OX40 occurs by crosslinking several molecules of OX40, which then induces a signal transduction cascade inside of the cell. For example, TRAF2, 3, and 5, and PI3K are activated upon OX40L binding to an OX40-expressing T cell. Certain antibodies that bind to OX40 mimic the functional effect of OX40L, however, other antibodies that bind to OX40 do not mimic the functional effect of OX40L. Though there are many high throughput methods that one skilled in the art uses to identify binders to the target of interest (e.g., phage display, yeast display, hybridoma screening, etc.), methods for identification of antibodies that induce a specific biological functional remain low-throughput, for example, practically limited to no more than 10-100 assays per week per laboratory technician. Therefore, there is a need for high-throughput methods to identify binders that induce a specific biological function. For example, high-throughput methods provided herein are used to identify immune agonists or antagonists, or to identify activation of signal transduction cascades.

To identify binders that induce a specific biological function, a mouse is immunized with a target protein of interest in the field of cancer biology. The target is a protein that is overexpressed on the surface of tumor cells (e.g., CD20, Her2, or EGFR), or a protein expressed on the surface of immune cells that modulate cancer (e.g., PD-1, OX40, or LAG3). Typical wild type mouse strains include BL/6, SJ/L, and Balb/c. The genome of the mouse has been engineered to express fully human or chimeric antibodies, for example, the Medarex or Trianni mice. Before sacrificing the animal, serum is removed and assessed for titer against the target of interest. Lymph nodes are then removed from the mouse. Spleens and bone marrow are removed from the mouse. Single cell suspensions are then generated from the organs, and B cells are separated from non-B cells. Methods for generating single cell suspensions from mouse organs include enzymatic digestion and physical disaggregation. Methods for separating B cells from non-B cells include flow cytometry and antibody-coated magnetic beads.

Specifically, OX40 is used as the immunogen for mouse immunization. Mouse immunization, overlap extension RT-PCR, and CHO cell engineering are used to generate a library of CHO cells that secrete antibody candidates against OX40. These antibodies are pre-enriched for binders against OX40, for example through scFv yeast or phage display. A plurality of clones from the library of antibody-secreting CHO cells are then isolated with OX40 expressing cells, for example, primary T cells or Jurkat cells engineered with OX40. The cells are partitioned into aqueous-in-oil droplets, and then incubated for 2, 4, 6, 12, 18, or 24 hours in a 37° C. tissue culture incubator. These droplets are 20-200 μm in diameter. The droplets are then injected into a second microfluidic chip that fuses the cell-containing droplets with droplets that contain lysis mix and oligo-dT microbeads. Cells are lysed with a surfactant such as SDS, and poly(A) RNA transcripts bind to the oligo-dT microbeads. Overlap extension droplet PCR using primers specific to immunoglobulin and T cell activation markers, (e.g., endogenous transcripts of T cell such as CD69 and IFNg or transcripts of a reporter engineered into target cells), such that the polynucleotides encoding the activation markers are linked through hybridization to polynucleotides encoding immunoglobulin. Droplet overlap extension RT-PCR is performed by injecting the beads into aqueous-in-oil reactors, and incubating in a tube in a conventional thermal cycler. The plurality of polynucleic acids generated by overlap extension RT-PCR are then subjected to bulk sequencing to identify and quantify antibody sequences linked to T cell activation markers. Heavy chain immunoglobulin is linked to activations markers and light chain immunoglobulin, to form fusion complexes of three, four, or more transcripts such that polynucleic acid sequences sufficient to produce antibody protein are generated. Heavy chain immunoglobulin is linked to activations markers and light chain immunoglobulin, such that two transcripts are linked, for example, heavy chain immunoglobulin and CD69. The antibody sequence is linked to the full transcriptome, and then the transcriptome is analyzed bioinformatically to detect sequence changes indicative of changes in cell function. From this experiment, antibodies secreted by antibody-secreting CHO cells that induce a functional response in T cells are identified.

Aantibody sequences linked to T cell activation markers are then cloned and purified as monoclonal antibody protein. The methods for cloning and purifying monoclonal antibodies are well known to those skilled in the art. These monoclonal antibodies are then validated for T cell activation by conventional well plate assays or mouse models for cancer. For example, NOD SCID gamma (NSG) mice are grafted with human immune cell progenitors, which give rise to differentiated human T cells in the mice. NSG mice are provided by commercial vendors such as Jackson Labs. The mice are then grafted with tumor cells, and provided with the candidate monoclonal antibody. The response of the T cells in these conditions is then compared to a variety of controls, for example, NSG mice with differentiated human T cells and tumor cells, but no antibody.

Example 5: Epitope Characterization Using Massively Parallel Functional Analysis Antibodies can be discovered by screening for binders against a complete protein, or a domain of a protein that comprises at least 100 amino acids, for example, through immunization of a mouse or panning with a phage display library. A drug developer is often interested to characterize the specific binding epitope of an antibody of interest. This information is useful for government regulatory filings but also may be useful for choosing antibodies with a desired functional profile, for example, antagonism or agonism of a protein or pathway. However, epitope characterization is conventionally a slow and expensive process. Additionally, conventional methods for epitope characterization do not take cellular function into account, rather, the conventional methods only take binding affinity into account. The field would benefit from a high-throughput epitope screening method that is based on functional analysis.

For a high-throughput epitope screening, an anti-Her2 antibody is generated by immunizing a mouse with the soluble, complete extracellular domain of Her2 and a library of putative Her2 epitopes is generated by engineering recombinant cells with peptides or domains from Her2, representing 10, 50, 100, 150, 200, or 250 amino acids, tethered to the cell membrane with a transmembrane domain. The library of Her2 epitopes comprises a set of overlapping peptides or domains that tile across the complete extracellular domain of the Her2 protein. The mRNA transcript encoding the epitope target also comprises a nucleic acid barcode sequence flanked by universal priming sites. The universal priming sites are used to amplify the nucleic acid barcode, which is used to identify the specific Her2 epitope clone. A plurality of single cells from a library of 5, 10, 50, 100, 150, 200, or 1000 epitope-expressing clones are partitioned into aqueous-in-oil droplets with NK cells and a CHO cell that secretes the anti-Her2 antibody of interest, and then the cell mixtures are incubated for 2, 4, 6, 12, 18, or 24 hours in a 37° C. tissue culture incubator. If the antibody binds to a given epitope, then the antibodies coating the epitope-expressing cell bind to CD16 molecules of the NK cells, which activates the NK cells. These droplets are 20-200 μm in diameter. The droplets are then injected into a second microfluidic chip that fuses the cell-containing droplets with droplets that contain lysis mix and oligo-dT microbeads. Cells are lysed with a surfactant such as SDS, and poly(A) RNA transcripts bind to the oligo-dT microbeads. Overlap extension droplet PCR using primers specific to the epitope clone and NK cell activation markers, for example, TNFa or IFNg, such that the polynucleotides encoding the activation markers are linked through hybridization to polynucleotides encoding the Her2 epitope. The NK cells can be NK-92 cells or primary NK cells or other kinds of mammalian cell lines, for example CHO, HEK293, or Jurkat, engineered to express CD16 receptors, where the artificial reporter substitutes endogenous NK activation markers. Universal primers are also used to amplify an epitope in the library of engineered epitope target-expressing cells. Droplet overlap extension RT-PCR is performed by injecting the beads into aqueous-in-oil reactors, and incubating in a tube in a conventional thermal cycler. The plurality of polynucleic acids generated by overlap extension RT-PCR are then subjected to bulk sequencing to identify and quantify Her2 epitope clone sequences linked to NK cell activation markers. From this experiment, Her2 epitopes that induce a functional response in NK cells are identified. The method can be used for any antibody that functions via ADCC.

A soluble form of the extracellular domain of OX40 is also used as an immunogen for mouse immunization. CHO cell engineering is used to generate a CHO clone that secretes an antibody against OX40. A library of cell-expressed putative OX40 epitopes is generated by engineering primary T cells or Jurkat cells with peptides or domains from OX40, representing 10, 50, 100, 150, 200, or 250 amino acids, tethered to the cell membrane with a transmembrane domain. The library of OX40 epitopes comprises a set of overlapping peptides or domains that tile across the complete extracellular domain of the OX40 protein. The mRNA transcript encoding the epitope target also comprises a nucleic acid barcode sequence flanked by universal priming sites. The universal priming sites are used to amplify the nucleic acid barcode, which is used to identify the OX40 epitope clone. A plurality of single cells from a library of 5, 10, 50, 100, 150, 200, or 1000 epitope-expressing clones are partitioned into aqueous-in-oil droplets with NK cells and a CHO cell that secretes the anti-OX40 antibody of interest, and then the cell mixtures are incubated for 2, 4, 6, 12, 18, or 24 hours in a 37° C. tissue culture incubator. These droplets are 20-200 μm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to the OX40 epitopes and T cell activation markers, for example, CD69 and IFNg, such that the polynucleotides encoding the activation markers are linked through hybridization to polynucleotides encoding an OX40 epitope. When the target cells are engineered to comprise a reporter gene by introduction of a plasmid or genome engineering, the reporter transcripts are used as activation markers. Droplet overlap extension RT-PCR is performed by injecting the beads into aqueous-in-oil reactors, and incubating in a tube in a conventional thermal cycler. The plurality of polynucleic acids generated by overlap extension RT-PCR are then subjected to bulk sequencing to identify and quantify antibody sequences linked to T cell activation markers. In this way, epitopes necessary and/or sufficient for OX40 activation are discovered. The epitope sequence is linked to the full transcriptome, and then the transcriptome is analyzed bioinformatically to detect sequence changes indicative of changes in cell function. From this experiment, the OX40 epitopes that induce a functional response in T cells, in the presence of the anti-OX40 antibody of interest, are identified. The method can be used for any antibody drug that functions via checkpoint inhibition.

Similar methods are used to characterize the functional binding epitopes of an antibody which is known to induce functional transcriptional changes in another type of cell. Candidate antibodies are cloned and purified as monoclonal antibody protein. The methods for cloning and purifying monoclonal antibodies are well known to those skilled in the art. These monoclonal antibodies are then validated for cell activation by conventional well plate assays or mouse models for cancer. For example, NOD SCID gamma (NSG) mice are grafted with human immune cell progenitors, which give rise to differentiated human T cells in the mice. NSG mice are provided by commercial vendors such as Jackson Labs. The mice are then grafted with tumor cells, and provided with the candidate monoclonal antibody. The response of the T cells in these conditions is then compared to a variety of controls, for example, NSG mice with differentiated human T cells and tumor cells, but no antibody.

Newly discovered epitopes that are necessary and sufficient to induce cell function, when paired with a given antibody, are then used to discover new antibodies that comprise similar or better functionality.

Example 6: Discovery of Bispecific Drugs

In many therapeutic situations, it is desirable for a single molecule to bind to two different targets, thereby inducing two different therapeutic mechanisms independently. For example, one component of the drug is an antibody fragment that binds one target, and another component of the drug is an antibody fragment that binds a second target. There are many formats for such bispecific drugs, for example, "bis-scFv", wherein two different scFv sequences, with two different specificities, are fused together with a peptide linker. For example, one scFv binds to and agonizes CD3, and the second scFv binds to EGFR, which is often overexpressed on the surface of certain tumors. Agonism of CD3 activates T cells, which then have tumor killing activity. Bispecific drugs are not limited to antibodies, for example, two TCRs can be fused to generate a bispecific TCR, an antibody can be fused to a TCR, or a recombinant ligand can be fused to an antibody fragment (e.g., OX40L fused to anti-CD3 antibody). A fusion molecule whose individual parts generate individual activities may not necessarily generate both activities when the individual parts are fused. Conventionally, bispecific activities are screened at a throughput of no more than 10-100 candidates per week per laboratory technician. Therefore, there is a need in the field for high-throughput methods that screen for multiple biological functions simultaneously.

To screen multiple biological functions simultaneously, libraries of bispecific drug candidates are subjected to the screening procedures of the present invention. Specifically, NK cell activation screens are performed with two distinct antibody targets in parallel (e.g., CD3 and EpCAM). Furthermore, NK cell activation screens are performed in series with TCR activation screens. Various combination of combinatorial screens is possible with the methods of the present invention.

Example 7: Functional Screen of Therapeutic T Cell Receptor Candidates

Therapeutic TCR drug discovery comprises mining of synthetic TCR repertoires, immunization and TCR recovery from mice, or mining of populations of human lymphocytes. Therapeutic T cell receptor drugs function by a variety of mechanisms, but the ability of TCR to bind to a given target does not necessarily guarantee that the TCR induces the required biological function.

However, it remains difficult to characterize the functional activity of T cell receptors that are known to bind to targets of interest. For example, a TCR is discovered from a library using MHC multimers, for example, MHC tetramers or MHC dextramers. When this TCR is expressed recombinantly in a T cell, the desired therapeutic mechanism of action is for the TCR-engineered T cell to bind to a peptide:MHC target on, for example, a target cell in a disease state, for example, a cancerous cell or a cell infected with a virus. However, proper binding of a TCR to a cognate peptide:MHC does not necessarily guarantee that the T cell will be activated. Therefore, the field would benefit from a method that screens libraries of TCRs for functional activity in the context of a target peptide:MHC of interest. Drug developers may use the TCR as a soluble drug or TCR-engineered T cell, or develop closely related, higher-affinity, or higher-activity, sequences once a functional sequence is known.

To screen a library of TCRs for functional activity, T cells are isolated from a cancer patient, for example, peripheral blood, bone marrow, or TILs. The cancer patient recently recovered from the cancer, is currently fighting the cancer, or is fighting the cancer and receiving immune modulating therapies. T cells are separated from non-T cells using methods known in the art such as flow cytometry and antibody-coated magnetic beads. The T cells are incubated with an antigen expressed in an APC, for the purpose of activating or expanding T cells of interest to the study. Primary T cells are subjected to emulsion overlap extension RT-PCR to generate a library of polynucleic acids with natively linked TCRαβ pairings. These libraries of TCRs are then used to engineer recombinant TCR-expressing cells, for example, Jurkat cells. Alternatively, the TCRαβ library is generated synthetically using molecular biology, instead of being derived from natural TCRαβ sequences expressed by primary T cells. Methods for engineering of recombinant cells can include electroporation of plasmids, lentiviral transduction, and lipid-based transfection. Cells transiently transfected with plasmids that express TCRs, or mRNAs that encode the TCRs of interest, primary T cells that express TCRs, or primary T cells engineered to express recombinant TCRs are used as the TCR-expressing cells.

A plurality of clones from the library of TCR-engineered cells are then isolated with the cells that express a cDNA, or cells from a tissue of interest, or cells expressing a tandem minigene ("target-expressing clones"). cDNAs are cloned into expression vectors that include polynucleotide sequences that encode for MHC expression, for example, HLA A*02:01, HLA A*24:02, or HLA DPB*04:01. This enables peptide target presentation in human antigen presenting cells that do not express the MHC of interest, or non-human antigen presenting cells. The APCs are cell lines, such as HEK293 or CHO cells, or primary cells, such as dendritic cells or B cells.

A plurality of clones from the library of TCR-engineered cells are then isolated with the target-expressing clones. The ratio of TCR-expressing cells to target-expressing cells is 1:1, 10:1, or 1:10. The cells are partitioned into aqueous-in-oil droplets, and then incubated for 2, 4, 6, 12, 18, or 24 hours in a 37° C. tissue culture incubator, such that the TCR-expressing clones bind to the cDNA-expressing cells, which activates the T cells. These droplets are 20-200 μm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to the target barcode or target sequence, and T cell activation markers, for example, CD69 or IFNg, such that the polynucleotides encoding the activation markers are linked through hybridization to polynucleotides that identify the target clone. TCR sequences from the T cells are also linked through hybridization to specific identifying sequences in the target cDNA transcript. The cDNA transcripts of the putative targets may contain synthetic polynucleic acid barcodes or unique non-synthetic sequences. Droplet overlap extension RT-PCR is performed by injecting the RNA-bound beads into aqueous-in-oil reactors, and incubating in a tube in a conventional thermal cycler. The T cell activation markers are endogenous transcripts expressed by the T cells, or transcriptional reporters engineered into T cells. The plurality of polynucleic acids generated by overlap extension RT-PCR are then subjected to bulk sequencing to identify and quantify TCR sequences linked to T cell activation markers, and then link these TCRβ to putative cDNA target transcripts. TCRβ is linked to T cell activations markers and TCRα, to form fusion complexes of three, four, or more transcripts such that polynucleic acid sequences sufficient to produce TCR protein are generated. TCRβ is linked to T cell activation markers and TCRα, such that only two transcripts are linked in a single molecule, for example, TCRβ and CD69. If the activation biomarkers are not activated, fewer overlap extension RT-PCR products will be generated, or no products will be generated, depending on the background expression level of the activation biomarker. From this experiment, cognate pairings between the peptide:MHC of interest and the TCRs from the TCR library that induce a functional response in T cells are identified. In this way, thousands, tens of thousands, hundreds of thousands, or millions of TCRs are discovered through high-throughput functional analysis. Polynucleic acids comprising the peptide:MHC target are linked to the full transcriptome of the T cells, and then the transcriptome is analyzed bioinformatically to detect sequence changes indicative of changes in cell function.

TCR sequences linked to T cell activation markers are then re-engineered into soluble format and purified as protein. The methods for cloning and purifying monoclonal TCRs are well known to those skilled in the art. In parallel, the associated target cDNA is cloned and used to validate the TCR by conventional well plate assays or mouse models for cancer. The TCR is engineered into T cells and used as a therapy, for example, adoptive T cell cancer therapy. The TCR-engineered T cells are validated non-clinically using in vitro methods, such as cell killing assays, for example by quantifying tumor cell killing by the TCR-engineered T cells in vitro. The TCR-engineered T cells are further validated with a mouse model, for example, NSG mice grafted with human lymphocytes, the TCR-engineered T cells, and tumor cells, wherein tumor cell killing is measured in vivo.

Libraries of TCRs not derived from human repertoires or randomly or synthetically generated can be used. When the target sequence is linked to the full transcriptome, the transcriptome is analyzed bioinformatically to detect sequence changes indicative of changes in cell function.

Example 8: Functional Analysis for Discovery of T Cell Receptor Targets

Because of the complexity of many diseases and the complexity of immune systems, it remains difficult to discover natural T cell receptors and their respective targets. This knowledge would be extremely useful to researchers studying the mechanism of disease, the mechanism of disease response, and methods for treating disease. For example, a TCR produced by a cancer patient binds to a tumor through specificity to a peptide:MHC target expressed by the tumor and unknown to science. Binding of the TCR to the tumor then induces cytotoxicity, clone propagation, and stimulation of other immune cells, which leads to complete remission of the cancer. One skilled in the art can appreciate the difficulty of finding the sequence of the functional TCRs well as the peptide:MHC target of the functional TCR. Drug developers may use the TCR as a soluble drug or TCR-engineered T cell, or develop closely related sequences once the endogenous sequence is known. Conventionally, it is difficult and expensive to obtain the complete complement of peptide:MHC targets present in a tumor. Therefore, the field would benefit from a high-throughput method that identifies the TCR and its peptide:MHC target, using the glycoprotein targets expressed by the tumor and the immune repertoire sequences expressed by the patient. The method is not limited to cancer, and can be applied to any disease that involves the immune system.

To identify TCR and its peptide:MHC target, T cells are isolated from a cancer patient, for example, peripheral blood, bone marrow, or TILs. In some embodiments of the invention, the cancer patient recently recovered from the cancer, is currently fighting the cancer, or is fighting the cancer and receiving immune modulating therapies. T cells are separated from non-T cells by methods such as flow cytometry and antibody-coated magnetic beads. The T cells are incubated with an antigen expressed in an APC, a pool of antigens expressed as a library of APC clones, cell lines, or primary tissues of interest (e.g., a tumor or tumor cells), for the purpose of activating or expanding T cells of interest to the study. The T cells are subjected to emulsion overlap extension RT-PCR to generate a library of polynucleic acids with natively linked TCRab pairings. These libraries of TCRs are then used to engineer recombinant TCR-expressing cells, for example, Jurkat cells. Cells are engineered using methods known in the art, such as electroporation of plasmids, lentiviral transduction, and lipid-based transfection. Recombinant cells transiently transfected with plasmids that express TCRs, or mRNAs that encode the TCRs of interest, The TCR-expressing cells are primary T cells that express TCRs, or primary T cells engineered to express recombinant TCRs.

A library of cell clones engineered to express surface TCRs is screened against a library of cell clones expressing putative TCR targets. Targets are encoded by complementary DNA cloned into an expression plasmid or a lentivirus. The cDNAs are derived from RNA isolated from a tumor, for example, a tumor that was surgically removed from the patient that provided the sample of T cells, or from a different patient or patients. The cDNAs are cloned into expression vectors that include polynucleotide sequences that encode for MHC expression, for example, HLA A*02: 01, HLA A*24:02, or HLA DPB*04:01. This enables peptide target presentation in human antigen presenting cells that do not express the MHC of interest, or non-human antigen presenting cells. The APCs are cell lines, such as HEK293 or CHO cells or primary cells, such as dendritic cells or B cells. MHC and the target cDNA are encoded on a single mRNA molecule, which also comprises a nucleic acid barcode sequence flanked by universal priming sites. The universal priming sites are used to amplify the nucleic acid barcode, which is used to identify the cDNA clone. The tumor is the same tissue of origin as the tumor from the patient that provided the sample of T cells, or from a different tissue of origin as the tumor from the patient that provided the sample of T cells. The cDNA is derived from tissues unrelated to tumors, or human donors without cancer. The library of putative TCR targets is generated by engineering recombinant cells with synthetic DNA cloned into an expression plasmid.

A plurality of clones from the library of TCR-engineered cells are then isolated with the cells that express a library of cDNAs ("target-expressing clones"). A typical ratio of TCR-expressing cells to target-expressing cells 1:1, 10:1, or 1:10. The cells are partitioned into aqueous-in-oil droplets, and then incubated for 2, 4, 6, 12, 18, or 24 hours in a 37° C. tissue culture incubator, such that the TCR-expressing clones bind to the cDNA-expressing cells, which activates the T cells. These droplets are 20-200 µm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to the target barcode or target sequence, and T cell activation markers, for example, CD69 or IFNg, such that the polynucleotides encoding the activation markers are linked through hybridization to polynucleotides that identify the target clone. TCR sequences from the T cells are also linked through hybridization to specific identifying sequences in the putative target cDNA transcript. The cDNA transcripts of the putative targets contain synthetic polynucleic acid barcodes or unique non-synthetic sequences. Droplet overlap extension RT-PCR is performed by injecting the RNA-bound beads into aqueous-in-oil reactors, and incubating in a tube in a conventional thermal cycler. The T cell activation markers used in these experiments are endogenous transcripts expressed by the T cells or transcriptional reporters engineered into T cells. The plurality of polynucleic acids generated by overlap extension RT-PCR are then subjected to bulk sequencing to identify and quantify TCR sequences linked to T cell activation markers, and then link these TCRβ to putative cDNA target transcripts. TCRβ is linked to T cell activations markers and TCRα, to form fusion complexes of three, four, or more transcripts such that polynucleic acid sequences sufficient to produce TCR protein are generated. TCRβ is linked to T cell activations markers and TCRα, such that only two transcripts are linked in a single molecule, for example, TCRβ and CD69. From this experiment, cognate pairings between peptide:MHC and TCRs that induce a functional response in T cells are identified, and these TCRs are linked in parallel to putative target cDNA transcripts. In this way, thousands, tens of thousands, hundreds of thousands, or millions of TCRs are paired with their target through high-throughput functional analysis. When polynucleic acids comprising the peptide:MHC target are linked to the full transcriptome of the T cells, the transcriptome is analyzed bioinformatically to detect sequence changes indicative of changes in cell function.

Libraries of TCRs which are not derived from human repertoires or TCR sequences which are randomly or synthetically generated can be used. The library of TCRs is screened against a library of recombinant cells expressing tumor cDNAs. A single monoclonal T cell population is also screened against a library of recombinant cells expressing tumor cDNAs.

TCR sequences linked to T cell activation markers are then re-engineered into soluble format and purified as protein. A cDNA target linked to T cell activation and at least one TCR sequence from an immune repertoire is then used to discover novel TCRs against the cDNA target, for example, through mouse immunization, phage display, or yeast display. The methods for cloning and purifying monoclonal TCRs are well known to those skilled in the art. In parallel, the associated target cDNA is cloned and used to validate the TCR by conventional well plate assays or mouse models for cancer. The TCR is engineered into autologous T cells and used as a therapy, for example, adoptive T cell cancer therapy. The TCR-engineered T cells are validated non-clinically using in vitro methods, such as cell killing assays, for example by quantifying tumor cell killing by the TCR-engineered T cells in vitro. The TCR-engineered T cells are further validated with a mouse model, for example, NSG mice grafted with human lymphocytes, the TCR-engineered T cells, and tumor cells, wherein tumor cell killing is measured in vivo.

Example 9: Functional Analysis of Tumor Infiltrating Lymphocytes

Tumor infiltrating lymphocytes (TILs) are T cells that have infiltrated a tumor in situ, and therefore are considered a rich source of tumor-antigen reactive T cells. TILs are expanded from tumor samples ex vivo, to produce billions of TILs in culture. The TILs are then infused back into the patient as a cellular therapy for combatting cancer. Expansion protocols involve culture for several months with growth factors and cytokines, which sometimes leads to efficacious cells but at other times leads to cells without efficacy. Thus, it would be useful to test the efficacy of TILs prior to infusion into the patient.

To test the efficacy of TILs, TILs are co-cultureed, as the target cells, with cells that express peptide:MHC of clinical relevance, as the inducer cells. TILs are screened against a library of cell clones expressing tumor antigens of interest for quality control. The target cells include peptide:MHC sequence similarity with the therapeutically relevant peptide:MHC target or complementary DNA cloned into an expression plasmid or a lentivirus. The cDNAs are derived from RNA isolated from a tumor, for example, a tumor that was surgically removed from the patient that provided the sample of T cells, or from a different patient or patients. The cDNAs are cloned into expression vectors that include polynucleotide sequences that encode for MHC expression, for example, HLA A*02:01, HLA A*24:02, or HLA DPB*04:01. This enables peptide target presentation in human APCs that do not express the MHC of interest, or non-human APCs. Cell lines, such as HEK293 or CHO cells or primary cells, such as dendritic cells or B cells are used as the APCs. An MHC and a target cDNA are encoded on a single mRNA molecule, which also comprises a nucleic acid barcode sequence flanked by universal priming sites. The universal priming sites are used to amplify the nucleic acid barcode, which is used to identify the cDNA clone. The barcode amplicons are then linked through OE-RT-PCR to induced transcripts or TCRs.

TIL cultures that fail to demonstrate efficacy are not infused back into the patient. Where possible, the TIL cultures may be further cultured under different conditions, for example, in the presence of a stimulatory antigen of clinical relevance to the patient.

Example 10: Functional Analysis of T cells in Response to Drugs

Dysregulation of T cell immunity is a hallmark of many kinds of human disease, including cancer and autoimmunity. Stimulation and suppression of T cell immunity involves a complex interplay among a variety of proteins, for example, LAG-3, OX40, OX40L, PD1, PDL1, CTLA4, CD47, 4-1BB, GITR, ICOS, and many others. One skilled in the art can appreciate that the field of immunology may not yet fully understand the complex interplay that results in stimulation and suppression of T cell immunity. It is likely that there are many components of this complex interplay that are unknown to science. Therefore, there remains a need for high-throughput single cell methods for further characterization of the molecular mechanisms of stimulation and suppression of T cell immunity.

To characterize the molecular mechanisms of stimulation and suppression of T cell immunity, recombinant DNA technology is used to engineer a library of cells that express molecules that are known to modulate immune regulatory pathways, such as antibodies that act as checkpoint inhibitors by antagonizing molecules such as PD-1, or endogenous ligands in immune regulatory pathways, for example, PD-L1, or secreted or membrane-boundimmune regulatory molecules. The library of immune modulatory cells comprises CHO, HEK293, or primary cells. Methods for engineering cells to express recombinant proteins are well known to those skilled in the art, for example, directed genome integration, transient expression via a plasmid, or lentivirus. The library of immune modulatory cells can comprise microbes, for example, engineered bacteria, yeast, or filamentous phage, instead of mammalian cells. The mRNA transcript encoding the immune modulator also comprises a nucleic acid barcode sequence flanked by universal priming sites. The universal priming sites are used to amplify the nucleic acid barcode, which is used to identify the immune modulator clone.

The library of cells expressing recombinant immune modulators is partitioned into aqueous-in-oil droplets with T cells, cells that express checkpoint molecules, or T cells engineered to express checkpoint molecules, and then the cell mixture emulsions are incubated for 2, 4, 6, 12, 18, or 24 hours in a 37° C. tissue culture incubator. These droplets are 20-200 μm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to the immune modulator clone and T cell activation markers, for example, TNFa or IFNg, using methods described above. The T cell activation markers comprise co-stimulatory or co-inhibitory checkpoint molecules, such as LAG-3, OX40, OX40L, PD1, PDL1, TIM3, CTLA4, CD47, 4-1BB, GITR, or ICOS. Primers specific to the immune modulator clone are linked to primers that amplify the full target cell transcriptome as cDNA. Bioinformatics is then used to discover genes that were not previously implicated in immune co-stimulatory or co-inhibitory pathways, or, to further clarify the function of previously characterized immune co-stimulatory or co-inhibitory pathways. Bioinformatics can be used to process the full-transcriptome data to generate transcript expression panels of 10, 100, or 1,000 genes that are upregulated or downregulated as part of co-stimulatory or co-inhibitory pathways. These transcript expression panels are used to test whether non-clinical candidate checkpoint inhibitor drugs have the desired effect on T cells or other target cells. The transcript expression panels are also used to test whether a given cancer patient responds to clinical-stage checkpoint molecules.

The emulsion droplet screen is further combined with FACS. For example, T cells are engineered to express a fluorescent reporter molecule that is induced upon incubation with a co-stimulatory or co-inhibitory drug. Droplets that contain activated reporters and are therefore fluorescent are sorted using FACS. The sorted emulsion droplets that contain reporter-positive cell mixtures are then processed using the methods described above. In some experiments, T cells are engineered to secrete molecules, which bind to target proteins linked to solid surfaces. Said binding is then detected by a method such as fluorescence resonance energy transfer (FRET). Droplets that bind to the target protein are therefore fluorescent and are sorted using FACS. The sorted emulsion droplets that contain FRET-positive cell mixtures are then processed using the methods described above. For the experiment, a FACS machine incorporated into microfluidic chips, or a conventional FACS machine provided by commercial vendors such as BD or Beckman Coulter is used. Similar methods are used for identifying droplets that contain antibody-secreting cells that bind to target proteins, or any other kind of cell that secretes a protein that binds a target protein. This provides a population of droplets that secrete proteins that bind a target protein. This method increases the specificity of the assay and enables to perform large combinatorial screens.

The screen benefits from performing a variety of incubation protocols in parallel. For example, mixtures of cells are incubated for 2, 4, 6, 12, 18, or 24 hours in a 37° C. tissue culture incubator, followed by incubation for 2 hours at 20° C., 25° C., 30° C., 35° C., or 40° C., all in a single experiment. Mixtures of cells expressing recombinant immune modulators mixed with T cells are partitioned, using the methods described above, into emulsion microdroplets. Light-triggered microtransponders, known in the art (e.g., Mandecki U.S. 20160175801), are delivered to the microdroplets with the cell mixtures. Similar methods are employed using "barcodes" encoded by RFID, quantum dots, colorimetric, or other physical means. The light-triggered microtransponders are then used to track delivery of cell mixtures to six chambers, which are then incubated for 2, 4, 6, 12, 18, or 24 hours in a 37° C. incubator. After incubation, each emulsion is then fed back into a microtransponder reader, which tracks delivery of cell mixtures to five chambers, at 20° C., 25° C., 30° C., 35° C., or 40° C. A microcomputer is used to generate a database of microtransponder barcodes and their associated protocols. In this way, six different first incubation protocols are tested combinatorially with five different second incubation protocols, for a total of 30 different combinations. This approach can be used for any kind of combinatorial screen.

Example 11: Functional Validation of Engineered Adoptive Cell Therapies

TCR-engineered T cells and CAR-T cells are a newer class of therapies that are primarily being used for cancer and infectious disease. The engineered cells are either autologous (i.e., derived from the patient) or allogeneic (i.e., derived from an individual other than the patient). All adoptive cell therapies must be characterized functionally prior to infusion into patients. Typically, such assays are limited to in vitro tumor cell killing assays. However, conventional assays fail to clearly identify specific killing of cells expressing therapeutic targets, and any off-target effects, i.e., killing of cells that should not be killed. Methods for functional quality control of adoptive cell therapy could make such therapies safer and more efficacious, for example, by demonstrating superiority of particular T cell transduction methods, or showing the specificity of a TCR or CAR-T in the context of different types of cells being used for engraftment, or different cell donors.

The method of present invention is used to screen cells engineered to express a therapeutic TCR against a library of cell clones expressing TCR targets of interest for quality control. Such targets include, for example, targets that are known to have peptide:MHC sequence similarity with the therapeutically relevant peptide:MHC target. Targets are encoded by complementary DNA cloned into an expression plasmid or a lentivirus. The cDNAs are derived from RNA isolated from a tumor, for example, a tumor that was surgically removed from the patient that provided the sample of T cells, or from a different patient or patients. The cDNAs are cloned into expression vectors that include polynucleotide sequences that encode for MHC expression, for example, HLA A*02:01, HLA A*24:02, or HLA DPB*04:01. This enables peptide target presentation in human antigen presenting cells that do not express the MHC of interest, or non-human antigen presenting cells. Cell lines, such as HEK293 or CHO cells or primary cells, such as dendritic cells or B cells are used as APCs. An MHC and a target cDNA are encoded on a single mRNA molecule, which also comprises a nucleic acid barcode sequence flanked by universal priming sites. The universal priming sites are used to amplify the nucleic acid barcode, which is used to identify the cDNA clone.

Cells engineered to express a therapeutic CAR-T are screened against a library of cell clone expressing antibody targets of interest for quality control. Such targets include, for example, surface protein targets that are known to have sequence similarity with the therapeutically relevant surface protein target. Targets are encoded by complementary DNA cloned into an expression plasmid or a lentivirus. The cDNAs are derived from RNA isolated from a tumor, for example, an autologous tumor that was surgically removed from the patient that provided the sample of T cells, or from a different patient or patients. Cell lines, such as HEK293 or CHO cells or primary cells, such as dendritic cells or B cells are used as the APCs. MHC and the target cDNA are encoded on a single mRNA molecule, which also comprises a nucleic acid barcode sequence flanked by universal priming sites. The universal priming sites are used to amplify the nucleic acid barcode, which is used to identify the cDNA clone.

The ratio between TCR-expressing cells and target-expressing cells is 1:1, 10:1, or 1:10. The cell mixtures are partitioned into aqueous-in-oil droplets, and then incubated for 2, 4, 6, 12, 18, or 24 hours in a 37° C. tissue culture incubator, such that the TCR-expressing or CAR-T cells bind to the cDNA-expressing cells, which activates the T cells. These droplets are 20-200 µm in diameter. The droplets are then injected into a second microfluidic chip that fuses the cell-containing droplets with droplets that contain lysis mix and oligo-dT microbeads. The cells are lysed with a surfactant such as SDS, and poly(A) RNA transcripts bind to the oligo-dT microbeads. Overlap extension droplet PCR using primers specific to the target barcode or target sequence, and T cell activation markers, for example, CD69 or IFNg, such that the polynucleotides encoding the activation markers are linked through hybridization to polynucleotides that identify the target clone. TCR or CAR-T sequences from the T cells are also linked through hybridization to specific identifying sequences in the putative target cDNA transcript. The cDNA transcripts of the putative targets may contain synthetic polynucleic acid barcodes or unique non-synthetic sequences. Droplet overlap extension RT-PCR is performed by injecting the RNA-bound beads into aqueous-in-oil reactors, and incubating in a tube in a conventional thermal cycler. The T cell activation markers are endogenous transcripts expressed by the T cells. The plurality of polynucleic acids generated by overlap extension RT-PCR are then subjected to bulk sequencing to identify and quantify TCR or CAR-T sequences linked to T cell activation markers, and then link these TCRβ to putative cDNA target transcripts. TCRβ is linked to T cell activations markers and TCRα, to form fusion complexes of three, four, or more transcripts such that polynucleic acid sequences sufficient to produce antibody protein are generated. TCRβ is linked to T cell activations markers and TCRα, such that only two transcripts are linked in a single molecule, for example, TCRβ and CD69. From this experiment, cognate pairings between peptide:MHC and TCRs, or CAR-T and surface targets, that induce a functional response in T cells are identified, and these TCRs or CAR-T are linked in parallel to putative target cDNA transcripts. The target sequence is linked to the full transcriptome, and then the transcriptome is analyzed bioinformatically to detect sequence changes indicative of changes in cell function.

The efficacy and specificity of the adoptive TCR-engineered or CAR-T cell therapy are estimated by benchmarking the sequence counts of on-target and off-target activation markers, respectively. The engineered T cell activation assay is used to generate control ranges for manufacturing a clinical therapeutic. The assay is used during non-clinical development of the CAR-T or TCR-engineered adoptive T cell therapy. A transcriptome-wide activation assay can be used to discover transcripts that comprise novel biomarkers for engineered T cell safety or efficacy.

The invention claimed is:

1. A method for functional analysis of biological cells, comprising:
- isolating into a monodisperse emulsion microdroplet a single target cell from a plurality of target cell clones of a first cell type, one or more inducer cells from a plurality of inducer cell clones of a second cell type, and one or more intermediary cells from a plurality of intermediary cell clones of a third cell type;
- incubating isolated cells in the monodisperse emulsion microdroplet, wherein the isolated cells comprise the single target cell, the one or more inducer cells, and the one or more intermediary cells;
- introducing an aqueous solution containing a lysis reagent into said monodisperse emulsion microdroplets, thereby inducing lysis of the isolated cells;
- capturing RNA released from the isolated cells on a solid surface; and
- generating a library of hybridized polynucleic acids that comprise a transcript from the isolated cells, wherein the hybridized polynucleic acids are indicative of transcriptional change in the single intermediary cell after the step of incubating the isolated cells.

2. The method of claim 1, wherein said hybridized polynucleic acids are indicative of transcriptional change in the one or more intermediary cells after the step of incubating the isolated cells.

3. The method of claim 2, wherein said transcriptional change in the one or more intermediary cells comprises increase of transcripts of a gene by less than tenfold.

4. The method of claim 1, wherein the plurality of target cell clones comprise more than 10,000 unique cell clones, wherein each target cell clone of the plurality of target cell clones is genetically distinct from each other.

5. The method of claim 1, wherein the plurality of inducer cell clones comprises more than 10,000 unique cell clones, wherein each inducer cell clone of the plurality of cell clones is genetically distinct from each other.

6. The method of claim 4, wherein genetic diversity of the target cell clones is created by introducing a library of nucleic acid sequences into a population of at least 100,000 cells.

7. The method of claim 5, wherein genetic diversity of the inducer cell clones is created by introducing a library of nucleic acid sequences into a population of at least 100,000 cells.

8. The method of claim 1, wherein RNA capturing is performed using oligonucleotides affixed to beads, wherein each bead has a diameter less than 10 ▢m.

9. The method of claim 1, wherein the hybridized polynucleic acids are generated by overlap extension polymerase chain reaction.

10. The method of claim 1, wherein the hybridized polynucleic acids are generated by first strand synthesis.

11. The method of claim 1, wherein the first cell type is a library of cells that express T cell receptors.

12. The method of claim 1, wherein the first cell type is a library of cells that express antibodies.

13. The method of claim 1, wherein the first cell type is a library of cells that express peptide: MHC.

14. The method of claim 1, wherein the first cell type is a library of cells that express polynucleic acid barcodes.

15. The method of claim 1, wherein cells are isolated into emulsions using microfluidics.

16. A method for functional analysis of a population of cells, comprising deep sequencing of the library of hybridized polynucleic acid of claim 1.

* * * * *

SEQUENCE LISTING

```
Sequence total quantity: 28
SEQ ID NO: 1                moltype = DNA   length = 64
FEATURE                     Location/Qualifiers
misc_feature                1..64
                            note = Description of Artificial Sequence: Synthetic primer
source                      1..64
                            mol_type = other DNA
                            organism = synthetic construct
SEQUENCE: 1
aggtcaagtt ccagcggcgg cggtggcagc ggaggcggcg gatcccagrt gcagctggtg    60
cart                                                                 64

SEQ ID NO: 2                moltype = DNA   length = 64
FEATURE                     Location/Qualifiers
misc_feature                1..64
                            note = Description of Artificial Sequence: Synthetic primer
source                      1..64
                            mol_type = other DNA
                            organism = synthetic construct
SEQUENCE: 2
aggtcaagtt ccagcggcgg cggtggcagc ggaggcggcg gatccsaggt ccagctggtr    60
cagt                                                                 64

SEQ ID NO: 3                moltype = DNA   length = 64
FEATURE                     Location/Qualifiers
misc_feature                1..64
                            note = Description of Artificial Sequence: Synthetic primer
source                      1..64
                            mol_type = other DNA
                            organism = synthetic construct
SEQUENCE: 3
aggtcaagtt ccagcggcgg cggtggcagc ggaggcggcg gatcccagrt caccttgaag    60
gagt                                                                 64

SEQ ID NO: 4                moltype = DNA   length = 20
FEATURE                     Location/Qualifiers
misc_feature                1..20
                            note = Description of Artificial Sequence: Synthetic primer
source                      1..20
                            mol_type = other DNA
                            organism = synthetic construct
SEQUENCE: 4
ccryggcttt gtcttggcat                                                20

SEQ ID NO: 5                moltype = DNA   length = 61
FEATURE                     Location/Qualifiers
misc_feature                1..61
                            note = Description of Artificial Sequence: Synthetic primer
source                      1..61
                            mol_type = other DNA
                            organism = synthetic construct
SEQUENCE: 5
aggtcaagtt ccagcggcgg cggtggcagc ggaggcggcg gtcagrtgca gctggtgcar    60
t                                                                    61

SEQ ID NO: 6                moltype = DNA   length = 61
FEATURE                     Location/Qualifiers
misc_feature                1..61
                            note = Description of Artificial Sequence: Synthetic primer
source                      1..61
                            mol_type = other DNA
                            organism = synthetic construct
SEQUENCE: 6
aggtcaagtt ccagcggcgg cggtggcagc ggaggcggcg gtsaggtcca gctggtrcag    60
t                                                                    61

SEQ ID NO: 7                moltype = DNA   length = 61
FEATURE                     Location/Qualifiers
misc_feature                1..61
                            note = Description of Artificial Sequence: Synthetic primer
source                      1..61
                            mol_type = other DNA
                            organism = synthetic construct
SEQUENCE: 7
aggtcaagtt ccagcggcgg cggtggcagc ggaggcggcg gtcagrtcac cttgaaggag    60
t                                                                    61

SEQ ID NO: 8                moltype = DNA   length = 54
```

```
FEATURE             Location/Qualifiers
misc_feature        1..54
                    note = Description of Artificial Sequence: Synthetic primer
source              1..54
                    mol_type = other DNA
                    organism = synthetic construct
SEQUENCE: 8
gccgccgctg gaacttgacc tagaggatcc gccgacagat ggtgcagcca cagt      54

SEQ ID NO: 9        moltype = DNA  length = 63
FEATURE             Location/Qualifiers
misc_feature        1..63
                    note = Description of Artificial Sequence: Synthetic primer
source              1..63
                    mol_type = other DNA
                    organism = synthetic construct
SEQUENCE: 9
aggtcaagtt ccagcggcgg cggtggcagc ggaggcggcg gtccctggga aaacactcac  60
aca                                                               63

SEQ ID NO: 10       moltype = DNA  length = 22
FEATURE             Location/Qualifiers
misc_feature        1..22
                    note = Description of Artificial Sequence: Synthetic primer
source              1..22
                    mol_type = other DNA
                    organism = synthetic construct
SEQUENCE: 10
gcacaactca atggtactgt cg                                          22

SEQ ID NO: 11       moltype = DNA  length = 61
FEATURE             Location/Qualifiers
misc_feature        1..61
                    note = Description of Artificial Sequence: Synthetic primer
source              1..61
                    mol_type = other DNA
                    organism = synthetic construct
SEQUENCE: 11
aggtcaagtt ccagcggcgg cggtggcagc ggaggcggcg gtggttgcgg agacatgctg  60
a                                                                 61

SEQ ID NO: 12       moltype = DNA  length = 19
FEATURE             Location/Qualifiers
misc_feature        1..19
                    note = Description of Artificial Sequence: Synthetic primer
source              1..19
                    mol_type = other DNA
                    organism = synthetic construct
SEQUENCE: 12
gtaggcgtag gctccaagg                                              19

SEQ ID NO: 13       moltype = DNA  length = 10404
FEATURE             Location/Qualifiers
misc_feature        1..10404
                    note = Description of Artificial Sequence: Synthetic
                    polynucleotide
source              1..10404
                    mol_type = other DNA
                    organism = synthetic construct
SEQUENCE: 13
gagtaattca tacaaaagga ctcgcccctg ccttggggaa tcccagggac cgtcgttaaa   60
ctcccactaa cgtagaaccc agagatcgct gcgttcccgc cccctcaccc gcccgctctc  120
gtcatcactg aggtggagaa gagcatgcgt gaggctccgg tgcccgtcag tgggcagagc  180
gcacatcgcc cacagtcccc gagaagttgg gggaggggtc ggcaattga accggtgcct   240
agagaaggtg gcgcgggta aactgggaaa gtgatgtcgt gtactggctc cgccttttc   300
ccgagggtgg gggagaaccg tatataagtg cagtagtcgc cgtgaacgtt ctttttcgca  360
acgggtttgc cgccagaaca caggtaagtg ccgtgtgtgg ttcccgcggg cctggcctca  420
ttacgggtta tggcccttgc gtgccttgaa ttacttccac gccccttggct gcagtacgtg  480
attcttgatc ccgagcttcg ggttggaagt gggtgggaga gttcgaggcc ttgcgcttaa  540
ggagcccctt cgcctcgtgc ttgagttgag gcctggcttg ggcgctgggg ccgccgcgtg  600
cgaatctggt ggcaccttcg cgcctgtctc gctgctttcg ataagtctct agccatttaa  660
aattttttgat gacctgctgc gacgcttttt ttctggcaag atagtcttgt aaatgcgggc  720
caagatctgc acactggtat ttcggttttt ggggccgcgg gcggcgacgg ggcccgtgcg  780
tcccagcgca catgttcggc gaggcggggc ctgagcgag aatcggacgg                840
gggtagtctc aagctggccg gcctgctctg tgcctggcc tcgcgccgcc gtgtatcgcc   900
ccgccctggg cggcaaggct ggccggtcg gcaccagttg cgtgagcgga agatggccg    960
cttcccggcc ctgctgcagg gagctcaaaa tggaggacgc ggcgctcggg agagcggcg  1020
ggtgagtcac ccacacaaag gaaaagggcc tttccgtcct cagccgtcgc ttcatgtgac 1080
tccacggagt accgggcgcc gtccaggcac ctcgattagt tctcgagctt ttggagtacg 1140
```

```
tcgtctttag gttgggggga ggggttttat gcgatggagt ttccccacac tgagtgggtg   1200
gagactgaag ttaggccagc ttggcacttg atgtaattct ccttggaatt tgcccttttt   1260
gagtttggat cttggttcat tctcaagcct cagacagtgg ttcaaagttt ttttcttcca   1320
tttcaggtgt cgtgaactag aagctttatt gcggtagttt atcacagtta aattgctaac   1380
gcagtcagtg cttctgacac aacagtctcg gccgccacca tgcaggccga aggccgggc   1440
acaggggtt cgacgggcga tgctgatggc ccaggaggcc ctggcattcc tgatggccca   1500
ggggcaatg ctggcggccc aggagaggcg ggtgccacgg gcggcagagg tccccggggc   1560
gcaggggcag caagggcctc ggggccggga ggaggcgccc cgcggggtcc gcatggcggc   1620
gcggcttcag ggctgaatgg atgctgcaga tgcggggcca ggggccgga gagccgcctg   1680
cttgagttct acctcgccat gccttcgcg cacaccatgg aagcagagct ggcccgcagg   1740
agcctggccc aggatgcccc accgcttccc gtgccagggg tgcttctgaa ggagttcact   1800
gtgtccggca acatactgac tatccgactg actgctgcag accaccgcca actgcagctc   1860
tccatcagct cctgtctcca gcagctttcc ctgttgatgt ggatcacgca gtgctttctg   1920
cccgtgtttt tggctcagcc tccctcaggg cagaggcgct aatctgagga gatggggtc   1980
ctgggcccca gggtgtgcag ccactgactt ggggactgct ggtggggtag ggatgaggga   2040
gggagggca ttgtgatgta cagggctgct ctgtgagatc aagggtctct taagggtggg   2100
agctgggca gggactacga gagcagccag atgggctgaa agtggaactc aaggggtttc   2160
tggcacctac ctacctgctt cccgctgggg ggtggggagt tggcccagag tcttaagatt   2220
ggggcagggt ggagaggtgg gctcttcctg cttcccactc atcttatagc tttctttccc   2280
cagatccgaa ttggagatcc aaaccaaggc gcgccatacc ggtcgccacc atggccgtca   2340
tggcgcccg aaccctcgtc ctgctactct cgggggctct ggccctgacc cagacctggg   2400
cgggctctca ctccatgagg tatttcttca catccgtctc ccggcccggc cgcggggacg   2460
cccgcttcat cgcagtgggc tacgtggacg acacgcagtt cgtgcggttc gacagcgacg   2520
ccgcgagcca gaggatggag ccgcgggcgc cgtggataga gcaggagggt ccggagtatt   2580
gggacgggga gacacggaaa gtgaaggccc actcacagac tcaccgagtg gacctgggga   2640
ccctgcgcgg ctactacaac cagagcgagg ccggttctca caccgtccag aggatgtatg   2700
gctgcgacgt ggggtcggac tggcgcttcc tccgcgggta ccaccagtac gcctacgacg   2760
gcaaggatta catcgccctg aaagaggacc tgcgctcttg gaccgcggcg gacatggcag   2820
ctcagaccac caagcacaag tgggaggcgg cccatgtggc ggagcagttg agagcctacc   2880
tggagggcac gtgcgtggag tggctccgca gatacctgga gaacgggaag gagacgctgc   2940
agcgcacgga cgcccccaaa acgcatatga ctcaccacgc tgtctctgac catgaagcca   3000
ccctgaggtg ctgggccctg agcttctacc ctgcggagat cacactgacc tggcagcggg   3060
atggggagga ccagacccag gacacggagc tcgtggagac caggcctgca ggggatggaa   3120
ccttccagaa gtgggcggct gtggtggtgc cttctggaca ggagcagaga tacacctgcc   3180
atgtgcagca tgagggtttg cccaagcccc tcaccctgag atgggagccg tcttcccagc   3240
ccaccatccc catcgtgggc atcattgctg gcctggttct ctttggagct gtgatcactg   3300
gagctgtggt cgctgctgtg atgtggagga ggaagagctc agatagaaaa ggagggagct   3360
actctcaggc tgcaagcagt gacagtgccc agggctctga tgtgtctctc acagcttgta   3420
aagtgtgagc ggccgcgatc ccgaaaaaaa aaaaaaaaaa aaaaaaaaaa aaaaaaaaaa   3480
aaaaaaaaaa aaagactggt tccaattgac aagctaatac gactcactat agggtaatac   3540
gactcactat aggggatgt cagaatgcca tttgccccct ctccctcccc ccccctaac   3600
gttactggcc gaagccgctt ggaataaggc cggtgtgcgt ttgtctatat gttatttttcc   3660
accatattgc cgtcttttgg caatgtgagg gcccggaaac ctggccctgt cttcttgacg   3720
agcattccta ggggtctttc ccctctcgcc aaaggaatgc aaggtctgtt gaatgtcgtg   3780
aaggaagcag ttcctctgga agcttcttga agacaaacaa cgtctgtagc gacccttgc   3840
aggcagcgga accccccacc tggcgacagg tgcctctgcg gccaaaagcc acgtgtataa   3900
gatacacctg caaaggcggc acaacccag tgccacgttg tgagttggat agttgtggaa   3960
agagtcaaat ggctctcctc aagcgtattc aacaaggggc tgaaggatgc ccagaagta   4020
ccccattgta tgggatctga tctggggcct cggtgcacat gctttacatg tgtttagtcg   4080
aggttaaaaa aacgtctagg ccccccgaac cacggggacg tggttttcct ttgaaaaaca   4140
cgatgataag cttgccacaa cccacaagga gacgacctt catgaccgag tacaagccca   4200
cggtgcgcct cgccaccgc gacgacgtcc cccgggccgc acgcaccctc gccgccgcgt   4260
tcgccgacta ccccgccacg cgccacaccg tcgacccgga ccgccacatc gagcgggtca   4320
ccgagctgca agaactcttc ctcacgcgcg tcgggctcga catcggcaag gtgtgggtcg   4380
cggacgacgg cgccgcggtg gcggtctgga ccacgcggaa gagcgtcgaa gcgggggcga   4440
tgttcgccga tcggcccg cgcatggccg agttgagcgg ttcccggctg gccgcgcagc   4500
aacagatgaa aggcctcctg gcgccgcacc ggcccaagga gcccgcgtgg ttcctggcca   4560
ccgtcggcgt ctcgcccgac caccagggca agggtctggg cagcgccgtc gtgctccccg   4620
gagtggaggc ggccgagcgc gccggggtgc ccgccttcct ggagacctcc gcgccccgca   4680
acctccccct ctacgagcgg ctcggcttca cgtcaccgc cgacgtcgag gtgcccgaag   4740
gaccgcgcac ctggtgcatg acccgcaagc ccggtgccta gacgcgtctg gaacaatcaa   4800
cctctgatt acaaaatttg tgaaagattg actggtattc ttaactatgt tgctcctttt   4860
acgctatgtg gatacgctgc tttaatgcct ttgtatcatg ctattgcttc ccgtatggct   4920
ttcattttct cctccttgta taaatcctgg ttgctgtctc tttatgagga gttgtgcccc   4980
gttgtcaggc aacgtggcgt ggtgtgcact gtgtttgctg acgcaacccc cactggttgg   5040
ggcattgcca ccacctgtca gctccttcc gggactttcg ctttcccct ccctattgcc   5100
acggcggaac tcatcgccgc ctgccttgcc cgctgctgga caggggctcg gctgttggc   5160
actgacaatt ccgtggtgtt gtcggggaag ctgacgtcct ttcatggct gtcgcctgt   5220
gttgccacct ggattctgcg cgggacgtcc ttctgctacg tccccttcgg cctcaatcca   5280
gcggaccttc cttcccgcgg cctgctgccg gctctgcggc ctcttccgcg tcttcgcctt   5340
cgccctcaga cgagtcggat ctccctttgg gccgcctccc cgcctggaat taattctgca   5400
gtcgagacct agaaaacat ggagcaatca caagtagcaa tacagcagct accaatgctg   5460
attgtgcctg gctagaagca caagaggagg aggaggtggg ttttccagtc acacctcagg   5520
acctttaaga ccaatgactt acaaggcagc tgtagatctt agccacttt taaaagaaaa   5580
gaggggactg gaagggctaa ttcactccca acgaagacaa gatctgcttt ttgcctgtac   5640
tgggtctctc tggttagacc agatctgagc ctgggagctc tctggctaac tagggaaccc   5700
actgcttaag cctcaataaa gcttgccttg agtgcttcaa gtagtgtgtg cccgtctgtt   5760
gtgtgactct ggtaactaga gatccctcag acccttttag tcagtgtgga aaatctctag   5820
cagtagtagt tcatgtcatc ttattattca gtatttataa cttgcaaaga aatgaatatc   5880
```

```
agagagtgag aggctagcgt tttaccgtcg acctctagct agagcttggc gtaatcatgg    5940
tcatagctgt ttcctgtgtg aaattgttat ccgctcacaa ttccacacaa catacgagcc    6000
ggaagcataa agtgtaaagc ctggggtgcc taatgagtga gctaactcac attaattgcg    6060
ttgcgctcac tgcccgcttt ccagtcggga aacctgtcgt gccagctgca ttaatgaatc    6120
ggccaacgcg cggggagagg cggtttgcgt attgggcgct cttccgcttc ctcgctcact    6180
gactcgctgc gctcggtcgt tcggctgcgg cgagcggtat cagctcactc aaaggcggta    6240
atacggttat ccacagaatc aggggataac gcaggaaaga acatgtgagc aaaaggccag    6300
caaaaggcca ggaaccgtaa aaaggccgcg ttgctggcgt ttttccatag gctccgcccc    6360
cctgacgagc atcacaaaaa tcgacgctca agtcagaggt ggcgaaaccc gacaggacta    6420
taaagatacc aggcgtttcc ccctggaagc tccctcgtgc gctctcctgt tccgaccctg    6480
ccgcttaccg gatacctgtc cgcctttctc ccttcgggaa gcgtggcgct ttctcatagc    6540
tcacgctgta ggtatctcag ttcggtgtag gtcgttcgct ccaagctggg ctgtgtgcac    6600
gaaccccccg ttcagcccga ccgctgcgcc ttatccggta actatcgtct tgagtccaac    6660
ccggtaagac acgacttatc gccactggca gcagccactg gtaacaggat tagcagagcg    6720
aggtatgtag gcggtgctac agagttcttg aagtggtggc ctaactacgg ctacactaga    6780
agaacagtat ttggtatctg cgctctgctg aagccagtta ccttcggaaa aagagttggt    6840
agctcttgat ccggcaaaca aaccaccgct ggtagcggtt ttttgtttg caagcagcag    6900
attacgcgca gaaaaaaagg atctcaagaa gatcctttga tcttttctac ggggtctgac    6960
gctcagtgga acgaaaactc acgttaaggg attttggtca tgagattatc aaaaaggatc    7020
ttcacctaga tccttttaaa ttaaaaatga agttttaaat caatctaaag tatatatgag    7080
taaacttggt ctgacagtta ccaatgctta atcagtgagg cacctatctc agcgatctgt    7140
ctatttcgtt catccatagt tgcctgactc cccgtcgtgt agataactac gatacgggag    7200
ggcttaccat ctggccccag tgctgcaatg ataccgcgag acccacgctc accggctcca    7260
gatttatcag caataaacca gccagccgga agggccgagc gcagaagtgg tcctgcaact    7320
ttatccgcct ccatccagtc tattaattgt tgccgggaag ctagagtaag tagttcgcca    7380
gttaatagtt tgcgcaacgt tgttgccatt gctacaggca tcgtggtgtc acgctcgtcg    7440
tttggtatgg cttcattcag ctccggttcc caacgatcaa ggcgagttac atgatccccc    7500
atgttgtgca aaaaagcggt tagctccttc ggtcctccga tcgttgtcag aagtaagttg    7560
gccgcagtgt tatcactcat ggttatggca gcactgcata attctcttac tgtcatgcca    7620
tccgtaagat gcttttctgt gactggtgag tactcaacca agtcattctg agaatagtgt    7680
atgcggcgac cgagttgctc ttgcccggcg tcaatacggg ataataccgc gccacatagc    7740
agaactttaa aagtgctcat cattggaaaa cgttcttcgg ggcgaaaact ctcaaggatc    7800
ttaccgctgt tgagatccag ttcgatgtaa cccactcgtg cacccaactg atcttcagca    7860
tcttttactt tcaccagcgt ttctgggtga gcaaaaacag gaaggcaaaa tgccgcaaaa    7920
aagggaataa gggcgacacg gaaatgttga atactcatac tcttcctttt tcaatattat    7980
tgaagcattt atcagggtta ttgtctcatg agcggataca tatttgaatg tatttagaaa    8040
aataaacaaa taggggttcc gcgcacattt ccccgaaaag tgccacctga cgtcgacgga    8100
tcgggagatc aacttgttta ttgcagctta taatggttac aaataaagca atagcatcac    8160
aaatttcaca aataaagcat ttttttcact gcattctagt tgtggtttgt ccaaactcat    8220
caatgtatct tatcatgtct ggatcaactg gataactcaa gctaaccaaa atcatcccaa    8280
acttcccacc ccatacccta ttaccactgc caattaccct gtggcgcaat taaccctcac    8340
taaagggaac aaaagctgga gctgcaagct taatgtagtc ttatgcaata ctcttgtagt    8400
cttgcaacat ggtaacgatg agttagcaac atgccttaca aggagagaaa aagcaccgtg    8460
catgccgatt ggtggaagta aggtggtacg atcgtgcctt attaggaagg caacagacgg    8520
gtctgacatg gattggacga accactgaat tgccgcattg cagagatatt gtatttaagt    8580
gcctagctcg atacataaac gggtctctct ggttagacca gatctgagcc tgggagctct    8640
ctggctaact agggaaccca tgcttaagc tcaataaag cttgccttga gtgcttcaag    8700
tagtgtgtgc ccgtctgttg tgtgactctg gtaactagag atccctcaga cccttttagt    8760
cagtgtggaa aatctctagc agtggcgccc gaacagggac ttgaaagcga aagggaaacc    8820
agaggagctc tctcgacgca ggactcggct tgctgaagcg cgcacggcaa gaggcgaggg    8880
gcggcgactg gtgagtacgc caaaaatttt gactagcgga ggctagaagg agagagatgg    8940
gtgcgagagc gtcagtatta agcggggag aattagatcg cgatgggaaa aaattccggtt    9000
aaggccaggg ggaaagaaaa aatataaatt aaaacatata gtatgggcaa gcagggagct    9060
agaacgattc gcagttaatc ctggcctgtt agaaacatca gaaggctgta gacaaatact    9120
gggacagcta caaccatccc ttcagacagg atcagaagaa cttagatcat tatataaatc    9180
agtagcaacc ctctattgtg tgcatcaaag gatagagata aaagacacca aggaagcttt    9240
agacaagata gaggaagagc aaaacaaaag taagaccacc gcacagcaag cggccggccg    9300
ctgatcttca gacctggagg aggagatatg agggacaatt aattggagaa gtgaattata    9360
taaatataaa gtagtaaaaa ttgaaccatt aggagtagca cccaccaagg caaagagaag    9420
agtggtgcag agagaaaaaa gagcagtggg aataggagct ttgttccttg ggttctttggg    9480
agcagcagga agcactatgg gcgcagcgtc aatgacgctg acggtacagg ccagacaatt    9540
attgtctggt atagtgcagc agcagaacaa tttgctgagg gctattgagg cgcaacagca    9600
tctgttgcaa ctcacagtct ggggcatcaa gcagctccag caagaatcc tggctgtgga    9660
aagatacccta aaggatcaac agctcctggg gatttggggt tgctctggaa aactcatttg    9720
caccactgct gtgccttgga atgctagttg gagtaataaa tctctggaac agatttggaa    9780
tcacacgacc tggatggagt gggacagaga aattaacaat tacacaagct taatacactc    9840
cttaattgaa gaatcgcaaa accagcaaga aaagaatgaa caagaattat tggaattaga    9900
taaatgggca agtttgtgga attggtttaa cataacaaat tggctgtgt atataaaatt    9960
attcataatg atagtaggag gcttggtagg tttaagaata gtttttgctg tactttctat   10020
agtgaataga gttaggcagg gatattcacc attatcgttt cagacccacc tcccaacccc   10080
gaggggaccc gacaggcccg aaggaataga agaagaaggt ggagagagag acagagacag   10140
atccattcga ttagtgaacg gatctcgacg gtatcgcctt aaaagaaaaa ggggggattg   10200
gggggtacag tgcagggaa agaatagtag acataatagc aacagacata caaactaaag   10260
aattacaaaa acaaattaca aaattcaaa attttcgggt ttattacagg gacagcagag   10320
atccagttta tctaatacga ctcactatag ggagagagag agaattaccc tcactaaagg   10380
gaggagaagc atgaattctt gggg                                          10404
SEQ ID NO: 14        moltype = DNA  length = 47
FEATURE              Location/Qualifiers
```

```
misc_feature            1..47
                        note = Description of Artificial Sequence: Synthetic primer
source                  1..47
                        mol_type = other DNA
                        organism = synthetic construct
SEQUENCE: 14
tcggctagct attcccatgg cgcgccgact ggttccaatt gacaagc                   47

SEQ ID NO: 15           moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 15
gcaaatggca ttctgacatc c                                               21

SEQ ID NO: 16           moltype = DNA  length = 10861
FEATURE                 Location/Qualifiers
misc_feature            1..10861
                        note = Description of Artificial Sequence: Synthetic
                         polynucleotide
source                  1..10861
                        mol_type = other DNA
                        organism = synthetic construct
SEQUENCE: 16
gagtaattca tacaaaagga ctcgcccctg ccttggggaa tcccagggac cgtcgttaaa     60
ctcccactaa cgtagaaccc agagatcgct gcgttcccgc cccctcaccc gcccgctctc    120
gtcatcactg aggtggagaa gagcatgcgt gaggctccag tgcccgtcag tgggcagagc    180
gcacatcgcc cacagtcccc gagaagttgg ggggagggt cggcaattga accggtgcct    240
agagaaggtg gcgcggggta aactgggaaa gtgatgtcgt gtactggctc cgccttttc    300
ccgagggtgg gggagaaccg tatataagtg cagtagtcgc cgtgaacgtt cttttcgca    360
acgggtttgc cgccagaaca caggtaagtc ccgtgtgtgt ttcccgcggg cctgcctct    420
ttacgggtta tggcccttgc gtgccttgaa ttacttccac gccccttgct gcagtacgtg    480
attcttgatc ccgagcttcg ggttggaagt gggtgggaga gttcgaggcc ttgcgcttaa    540
ggagcccctt cgcctcgtgc ttgagttgag gcctggcttg ggcgctgggg ccgccgcgtg    600
cgaatctggt ggcaccttcg cgcctgtctc gctgctttcg ataagtctct agccatttaa    660
aattttgat gacctgctgc gacgcttttt tctggcaag atagtcttgt aaatgcgggc    720
caagatctgc acactggtat ttcggttttt ggggccgcgg gcggcgacgg ggcccgtgcg    780
tcccagcgca catgttcggc gaggcggggc ctgcagcgc ggccaccgag aatcggacgg    840
gggtagtctc aagctggccg gcctgctctg gtgcctggcc tcgcgccgcc gtgtatcgcc    900
ccgccctggg cggcaaggct ggcccggtcg gcaccagttg cgtgagcgga aagatggccg    960
cttcccggcc ctgctgcagg gagctcaaaa tggaggacgc ggcgctcggg agagcggggc    1020
ggtgagtcac ccacacaaag gaaaagggcc tttccgtcct cagccgtcgc ttcatgtgac    1080
tccacggagt accgggcgcc gtccaggcac ctcgattagt tctcgagctt ttggagtacg    1140
tcgtctttag gttgggggga ggggttttat gcgatgagt ttccccacac tgagtgggtg    1200
gagactgaag ttaggccagc ttggcacttg atgtaattct ccttggaatt tgccctttt    1260
gagtttggat cttggttcat tctcaagcct cagacagtgg ttcaaagttt ttttcttcca    1320
tttcaggtgt cgtgaactag aagctttatt gcggtagttt atcacagtta aattgctaac    1380
gcagtcagtg cttctgacac aacagtctcg gccgccacca gcagacagag gactctcatt    1440
aaggaaggtg tcctgtgccc tgaccctaca agatgccaag agaagatgct cacttcatct    1500
atggttaccc caagaagggg cacggccact cttacaccac ggctgaagag gccgctggga    1560
tcggcatcct gacagtgatc ctgggagtct tactgctcat cggctgttgg tattgtgaaa    1620
gacgaaatgg atacagagcc ttgatggata aaagtcttca tgttggcact caatgtgcct    1680
taacaagaag atgccacaa gaagggtttg atcatcggga cagcaaagtg tctcttcaag    1740
agaaaaactg tgaacctgtg gttcccaatg ctccacctgc ttatgagaaa ctctctgcag    1800
aacagtcacc accaccttat tcaccttaag agccagcgag acacctgaga catgctgaaa    1860
ttatttctct cacactttg cttgaattta atacagacat ctaatgttct ccctttggaat    1920
ggtgtaggaa aaatgcaagc catctctaat aataagtcag tgttaaaatt ttagtaggtc    1980
cgctagcagt actaatcatg tgaggaaatg atgagaaata ttaaattggg aaaactccat    2040
caataaatgt tgcaatgcat gatactatct gtgccagagg taatgttagt aaatccatgg    2100
tgttattttc tgagagacag aattcaagtg ggtattctgg ggccatccaa tttctcttta    2160
cttgaaattt ggctaataac aaactagtca ggttttcgaa ccttgaccga catgaactgt    2220
acacagaatt gttccagtac tatggagtgc tcacaaagga tacttttaca ggttaagaca    2280
aagggttgac tggcctattt atctgatcaa gaacatgtca gcaatgtctc tttgtgctct    2340
aaaattctat tatactacaa taatatattg taaagatcct atagctcttt ttttttgaga    2400
tggagtttcg cttttgttgt ctcgagagat gggggtcctg ggcccaggg tgtgcagcca    2460
ctgacttggg gactgctggt ggggtaggga tgaggaggga aggggcattg tgatgtacag    2520
ggctgctctg tgagatcaag ggtctcttaa gggtggggagc tggggcaggg actacgagag    2580
cagccagatg ggctgaaagt ggaactcaag gggtttctgg cacctaccta cctgcttccc    2640
gctgggggt ggggagttgg cccagagtct taagattggg gcagggtgga gaggtgggct    2700
cttcctgctt cccactcatc ttatagcttt ctttccccag atccgaattg gagatccaaa    2760
ccaaggcgcg ccatacggt cgccaccatg cgccccgaac cctcgtccg                2820
ctactctcgg gggctctggc cctgaccag acctggcgg gctctcactc catgaggtat    2880
ttcttcacat ccgtgtcccg gcccggccgc gggagcccc gcttcatcgc agtgggctac    2940
gtggacgaca cgcagttcgt gcggttcgac agcgacgccg cgagcagag gatggagccg    3000
cgggcgccgg ggatagagca ggagggtccg gagtattggg acgggagac acggaaagtg    3060
aaggcccact cacagactca ccgagtggac ctggggaccc tgcgcggcta ctacaaccag    3120
```

```
agcgaggccg gttctcacac cgtccagagg atgtatggct gcgacgtggg gtcggactgg   3180
cgcttcctcc gcgggtacca ccagtacgcc tacgacggca aggattacat cgccctgaaa   3240
gaggacctgc gctcttggac cgcggcggac atggcagctc agaccaccaa gcacaagtgg   3300
gaggcggccc atgtggcgga gcagttgaga gcctacctgg agggcacgtg cgtggagtgg   3360
ctccgcagat acctggagaa cgggaaggag acgctgcagc cccaaaaacg              3420
catatgactc accacgctgt ctctgaccat gaagccaccc tgaggtgctg ggccctgagc   3480
ttctaccctg cggagatcac actgacctgg cagcgggatg ggaggacca gacccaggac    3540
acggagctcg tggagaccag gcctgcaggg gatggaacct tccagaagtg ggcggctgtg   3600
gtggtgcctt ctggacagga gcagagatac acctgccatg tgcagcatga gggtttgcct   3660
aagcccctca ccctgagatg ggagccgtct tcccagccca ccatcccat cgtgggcatc    3720
attgctggcc tggttctctt tggagctgtg atcactggag ctgtggtcgc tgctgtgatg   3780
tggaggagga agagctcaga tagaaaagga gggagctact ctcaggctgc aagcagtgac   3840
agtgcccagg gctctgatgt gtctctcaca gcttgtaaag tgtgagcggc cgcgatcccg   3900
aaaaaaaaaa aaaaaaaaaa aaaaaaaaaa aaaaaaaaaa aaaaaaaaaa gactggttcc   3960
aattgacaag ctaatacgac tcactgatcg aatcggtatg tcactatagg gggatgtcag   4020
aatgccattt gcccctctc cctccccccc cctaacgtt actggccgaa gccgcttgga     4080
ataaggccgg tgtgcgtttg tctatatgtt attttccacc atattgccgt cttttggcaa   4140
tgtgagggcc cggaaacctg gccctgtctt cttgacgagc attcctaggg gtcttttccc   4200
tctcgccaaa ggaatgcaag gtctgttgaa tgtcgtgaag gaagcagttc ctctggaagc   4260
ttcttgaaga caaacaacgt ctgtagcgac cctttgcagg cagcggaacc ccccacctgg   4320
cgacaggtgc ctctgcggcc aaaagccacg tgtataagat acacctgcaa aggcggcaca   4380
accccagtgc cacgttgtga gttgatagt tgtggaaaga gtcaaatggc tctcctcaag    4440
cgtattcaac aaggggctga aggatgccca gaaggtaccc cattgtatgg gatctgatct   4500
ggggcctcgg tgcacatgct ttacatgtgt ttagtcgagg ttaaaaaaac gtctaggccc   4560
cccgaaccac ggggacgtgg ttttcctttg aaaaacacga tgataagctt gccacaaccc   4620
acaaggagac gaccttccat gaccagctac aagcccagtg tgcgcctcgc caccgcgac    4680
gacgtccccc gggccgtacg caccctcgcc gccgcgttcg ccgactaccc cgccacgcgc   4740
cacaccgtcg acccggaccg ccacatcgag cgggtcaccg agctgcaaga actcttcctc   4800
acgcgcgtcg ggctcgacat cggcaaggtg tgggtcgcgg acgacggcgc cgcggtggcg   4860
gtctgtacca cgccggagag cgtcgaagcg ggggcggtgt tcgccgagat cggccccgcc   4920
atggccgagt tgagcggttc ccggctggcc gcgcagcaac agatggaagg cctcctggcc   4980
ccgcaccggc ccaaggagcc cgccgtggtt ctggccaccg tcggcgtctc gcccgaccac   5040
cagggcaagg gtctgggcag cgccgtcgtg ctccccggag tggaggcggc cgagcgcgcc   5100
ggggtgcccg ccttcctgga gacctccgcg ccccgcaacc tcccccttcta cgagcggtcc   5160
ggcttcaccg tcaccgccga cgtcgaggtg cccgaaggac cgcgcacctg gtgcatgacc   5220
cgcaagcccg gtgcctagac gcgtctgaa caatcaacct ctggattaca aaatttgtga    5280
aagattgact ggtattctta actatgttgc tccttttacg ctatgtggat acgctgcttt   5340
aatgcctttg tatcatgcta ttgcttcccg tatggctttc attttctcct ccttgtataa   5400
atcctggttg ctgtctcttt atgaggagtt gtggcccgtt gtcaggcaac gtggcgtggt   5460
gtgcactgtg tttgctgacg caaccccccac tggttgggc attgccacca cctgtcagct   5520
cctttccggg actttcgctt tccccctccc tattgccacg cgggaactca tcgccgcctg   5580
ccttgcccgc tgctggacag gggctcggct gttgggcact gacaattccg tggtgttgtc   5640
ggggaagctg acgtccttc catggctgct cgcctgtgtt gccacctgga ttctgcgcgg   5700
gacgtccttc tgctacgtcc cttcggccct caatccagcg gaccttcctt cccgcggcct   5760
gctgccggct ctgcggcctc ttccgcgtct tcgccttcgc cctcagacga tcggatctc    5820
cctttgggcc gcctccccgc ctggaattaa ttctgcagtc gagacctaga aaacatgga    5880
gcaatcacaa gtagcaatac agcagctat aatgctgatt gtgcctggct agaagcacaa    5940
gaggaggagg aggtgggttt tccagtcaca cctcaggacc tttaagacca atgacttaca   6000
aggcagctgt agatcttagc cacttttaa aagaaaagag gggactggaa gggctaattc    6060
actcccaacg aagacaagat ctgctttttg cctgtactgg gtctctctgg ttagaccaga   6120
tctgagcctg ggagctctct ggctaactag ggaacccact gcttaagcct caataaagct   6180
tgccttgagt gcttcaagta gtgtgtgccc gtctgttgtg tgactctggt aactagagat   6240
ccctcagacc cttttagtca gtgtggaaaa tctctagcag tagtagttca tgtcatctta   6300
ttattcagta tttataactt gcaaagaaat gaatatcaga gagtgagagg ctagcgtttt   6360
accgtcgacc tctagctaga gcttggcgta atcatggtca tagctgtttc ctgtgtgaaa   6420
ttgttatccg ctcacaattc cacacaacat acgagccgga agcataaagt gtaaagcctg   6480
gggtgcctaa tgagtgagct aactcacatt aattgcgttg cgctcactgc ccgctttcca   6540
gtcgggaaac ctgtcgtgcc agctgcatta tgaatcggc caacgcgcgg ggagaggcgg    6600
tttcgcgtatt gggcgctctt ccgcttcctc gctcactgac tcgctgcgct cggtcgttcg   6660
gctgcggcga gcggtatcag ctcactcaaa ggcggtaata cggttatcca cagaatcagg   6720
ggataacgca ggaaagaaca tgtgagcaaa aggccagcaa aaggccagga accgtaaaaa   6780
ggccgcgttg ctggcgtttt tccataggct ccgcccccct gacgagcatc acaaaaatcg   6840
acgctcaagt cagaggtggc gaaacccgac aggactataa agataccagg cgtttccccc   6900
tggaagctcc ctcgtgcgct ctcctgttcc gaccctgccg cttaccggat acctgtccgc   6960
ctttctccct tcgggaagcg tggcgctttc tcatagctca cgctgtaggt atctcagttc   7020
ggtgtaggtc gttcgctcca agctgggctg tgtgcacgaa ccccccgttc agcccgaccg   7080
ctgcgcctta tccggtaact atcgtcttga gtccaacccg gtaagacacg acttatcgcc   7140
actggcagca gccactggta acaggattag cagagcgagg tatgtaggcg gtgctacaga   7200
gttcttgaag tggtggccta actacggcta cactagaaga cagatttg gtatctgcgc     7260
tctgctgaag ccagttacct tcggaaaaag agttggtagc tcttgatccg gcaaacaaac   7320
caccgctggt agcggttttt tgttcgcaa gcagcagatt acgcgcagaa aaaaaggatc    7380
tcaagaagat cctttgatct tttctacggg gtctgacgct cagtggaacg aaaactcacg   7440
ttaagggatt ttggtcatga gattatcaaa aaggatcttc acctagatcc ttttaaatta   7500
aaaatgaagt tttaaatcaa tctaaagtat atatgagtaaa acttggtctg acagttacca   7560
atgcttaatc agtgaggcac ctatctcagc gatctgtcta tttcgttcat ccatagttgc   7620
ctgactcccc gtcgtgtaga taactacgat acgggagggc ttaccatctg gccccagtgc   7680
tgcaatgata ccgcgagacc cacgctcacc ggctccagat ttatcagcaa taaaccagcc   7740
agccggaagg gccgagcgca gaagtggtcc tgcaacttta tccgcctcca tccagtctat   7800
taattgttgc cgggaagcta gagtaagtag ttcgccagtt aatagtttgc gcaacgttgt   7860
```

```
tgccattgct acaggcatcg tggtgtcacg ctcgtcgttt ggtatggctt cattcagctc  7920
cggttcccaa cgatcaaggc gagttacatg atccccatg ttgtgcaaaa aagcggttag   7980
ctccttcggt cctccgatcg ttgtcagaag taagttggcc gcagtgttat cactcatggt  8040
tatggcagca ctgcataatt ctcttactgt catgccatcc gtaagatgct tttctgtgac  8100
tggtgagtac tcaaccaagt cattctgaga atagtgtatg cggcgaccga gttgctcttg  8160
cccggcgtca atacgggata ataccgcgcc acatagcaga actttaaaag tgctcatcat  8220
tggaaaacgt tcttcggggc gaaaactctc aaggatctta ccgctgttga gatccagttc  8280
gatgtaaccc actcgtgcac ccaactgatc ttcagcatct tttactttca ccagcgtttc  8340
tgggtgagca aaaacaggaa ggcaaaatgc cgcaaaaaag ggaataaggg cgacacggaa  8400
atgttgaata ctcatactct tccttttca atattattga agcatttatc agggttattg   8460
tctcatgagc ggatacatat ttgaatgtat ttagaaaaat aaacaaatag gggttccgcg  8520
cacatttccc cgaaaagtgc cacctgacgt cgacggatcg ggagatcaac ttgtttattg  8580
cagcttataa tggttacaaa taaagcaata gcatcacaaa tttcacaaat aaagcatttt  8640
tttcactgca ttctagttgt ggtttgtcca aactcatcaa tgtatcttat catgtctgga  8700
tcaactggat aactcaagct aaccaaaatc atcccaaact tcccacccca taccctatta  8760
ccactgccaa ttccctgtg gcgcaattaa ccctcactaa agggaacaaa agctggagct   8820
gcaagcttaa tgtagtctta tgcaatactc ttgtagtctt gcaacatggt aacgatgagt  8880
tagcaacatg ccttacaagg agagaaaaag caccgtgcat gccgattggt ggaagtaagg  8940
tggtacgatc gtgccttatt aggaaggcaa cagacgggtc tgacatggat tggacgaacc  9000
actgaattgc cgcattgcag agatattgta tttaagtgcc tagctcgata cataaacggg  9060
tctctctggt tagaccagat ctgagcctgg gagctctctg gctaactagg gaacccactg  9120
cttaagcctc aataaagctt gccttgagtg cttcaagtag tgtgtgcccg tctgttgtgt  9180
gactctggta actagagatc cctcagaccc ttttagtcag tgtggaaaat ctctagcagt  9240
ggcgcccgaa cagggacttg aaagcgaaag gaaaccaga ggagctctct cgacgcagga   9300
ctcggcttgc tgaagcgcgc acggcaagag gcgaggggcg cgactggtg agtacgccaa   9360
aaattttgac tagcggaggc tagaaggaga gagatgggtg cgagagcgtc agtattaagc  9420
gggggagaat tagatcgcga tgggaaaaaa ttcggttaag gccagggggga aagaaaaat   9480
ataaattaaa acatatagta tgggcaagca gggagctaga acgattcgca gttaatcctg  9540
gcctgttaga acatcagaa ggctgtagac aaatactggg acagctacaa ccatcccttc   9600
agacaggatc agaagaactt agatcattat ataatacagt gcaaccctc tattgtgtgc   9660
atcaaaggat agatataaa gacaccaagg aagctttaga caagatagag gaagagcaaa   9720
acaaaagtaa gaccaccgca cagcaagcgg ccggccgctg atcttcagac ctggaggagg  9780
agatatgagg gacaattaat tggagaagtg aattatataa atataagta gtaaaaattg   9840
aaccattagg agtagcaccc accaaggcaa agagaagagt ggtgcagaga gaaaaagag   9900
cagtggggaat aggagctttg ttccttgggt tcttgggagc agcaggaagc actatgggcg  9960
cagcgtcaat gacgctgacg gtacaggcca gacaattatt gtctggtata gtgcagcagc  10020
agaacaattt gctgagggct attgaggcgc aacagcatct gttgcaactc acagtctggg  10080
gcatcaagca gctccaggca agaatcctgg ctgtggaaag ataccctaaag gatcaacagc  10140
tcctggggat ttgggggttgc tctggaaaac tcatttgcac cactgctgtg ccttggaatg  10200
ctagttggag taataaatct ctggaacaga tttggaatca cacgacctgg atggagtggg  10260
acagagaaat taacaattac acaagcttaa tacactcctt aattgaagaa tcgcaaaacc  10320
agcaagaaaa gaatgaacaa gaattattgg aattagataa atgggcaagt ttgtggaatt  10380
ggtttaacat aacaaattgg ctgtggtata taaaattatt cataatgata ctaggaggct  10440
tggtaggttt aagaatagtt tttgctgtac tttctatagt gaatagagtt aggcaggat   10500
attcaccatt atcgtttcag acccacctcc caaccccgag ggacccgac aggcccgaag   10560
gaatagaaga agaaggtgga gagagagaca gagacagatc cattcgatta gtgaacggat   10620
ctcgacgtta tcgcctttaa aagaaaaggg gggattgggg ggtacagtgc aggggaaaga  10680
atagtagaca taataqcaac agacatacaa actaaagaat tacaaaaaca aattacaaaa  10740
attcaaaatt ttcggggttta ttacagggac agcagagatc cagtttatct aatacgactc  10800
actatagggga gagagagaga attcccctca ctaaagggag gagaagcatg aattcttggg  10860
g                                                                  10861
```

```
SEQ ID NO: 17        moltype = DNA  length = 49
FEATURE              Location/Qualifiers
misc_feature         1..49
                     note = Description of Artificial Sequence: Synthetic primer
source               1..49
                     mol_type = other DNA
                     organism = synthetic construct
SEQUENCE: 17
tcggctagct attcccatgg cgcgccgatg ctgaagtcrc mcagactcc                49

SEQ ID NO: 18        moltype = DNA  length = 46
FEATURE              Location/Qualifiers
misc_feature         1..46
                     note = Description of Artificial Sequence: Synthetic primer
source               1..46
                     mol_type = other DNA
                     organism = synthetic construct
SEQUENCE: 18
tcggctagct attcccatgg cgcgccgatg cwgmtgttwc ccagac                   46

SEQ ID NO: 19        moltype = DNA  length = 49
FEATURE              Location/Qualifiers
misc_feature         1..49
                     note = Description of Artificial Sequence: Synthetic primer
source               1..49
                     mol_type = other DNA
                     organism = synthetic construct
```

```
SEQUENCE: 19
tcggctagct attcccatgg cgcgccgaca ctgragtyac scagacacc            49

SEQ ID NO: 20             moltype = DNA   length = 25
FEATURE                   Location/Qualifiers
misc_feature              1..25
                          note = Description of Artificial Sequence: Synthetic primer
source                    1..25
                          mol_type = other DNA
                          organism = synthetic construct
SEQUENCE: 20
caggcayacc agtgtggcct tttgg                                      25

SEQ ID NO: 21             moltype = DNA   length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 21
ggactggttg taaaacgacg gccagtggac aaarcmttga scagcc                46

SEQ ID NO: 22             moltype = DNA   length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 22
ggactggttg taaaacgacg gccagtaagg accaagtgtt tcagcc                46

SEQ ID NO: 23             moltype = DNA   length = 46
FEATURE                   Location/Qualifiers
misc_feature              1..46
                          note = Description of Artificial Sequence: Synthetic primer
source                    1..46
                          mol_type = other DNA
                          organism = synthetic construct
SEQUENCE: 23
ggactggttg taaaacgacg gccagtgctc agtcagtgrc ycagcc                46

SEQ ID NO: 24             moltype = DNA   length = 51
FEATURE                   Location/Qualifiers
misc_feature              1..51
                          note = Description of Artificial Sequence: Synthetic primer
source                    1..51
                          mol_type = other DNA
                          organism = synthetic construct
SEQUENCE: 24
ggcgcgccat gggaatagct agccgacaga cagacttgtc actggattta g          51

SEQ ID NO: 25             moltype = DNA   length = 51
FEATURE                   Location/Qualifiers
misc_feature              1..51
                          note = Description of Artificial Sequence: Synthetic primer
source                    1..51
                          mol_type = other DNA
                          organism = synthetic construct
SEQUENCE: 25
aatgatacgg cgaccaccga gatctacacg ggttctcttg gctgttactg c          51

SEQ ID NO: 26             moltype = DNA   length = 51
FEATURE                   Location/Qualifiers
misc_feature              1..51
                          note = Description of Artificial Sequence: Synthetic primer
source                    1..51
                          mol_type = other DNA
                          organism = synthetic construct
SEQUENCE: 26
ggcgcgccat gggaatagct agccgaggat gctctggtca tctttaaagt t          51

SEQ ID NO: 27             moltype = DNA   length = 51
FEATURE                   Location/Qualifiers
misc_feature              1..51
                          note = Description of Artificial Sequence: Synthetic primer
source                    1..51
                          mol_type = other DNA
```

```
                        organism = synthetic construct
SEQUENCE: 27
aatgatacgg cgaccaccga gatctacaca tgcccaagaa ggccacagaa c            51

SEQ ID NO: 28           moltype = DNA   length = 50
FEATURE                 Location/Qualifiers
misc_feature            1..50
                        note = Description of Artificial Sequence: Synthetic primer
source                  1..50
                        mol_type = other DNA
                        organism = synthetic construct
SEQUENCE: 28
ggcgcgccat gggaatagct agccgataca atggttgctg tctcatcagc             50
```